(12) United States Patent
Kwiek et al.

(10) Patent No.: US 10,966,981 B2
(45) Date of Patent: Apr. 6, 2021

(54) FATTY ACID SYNTHASE INHIBITORS

(71) Applicants: Duke University, Durham, NC (US); Ohio State Innovation Foundation, Columbus, OH (US)

(72) Inventors: Jesse Kwiek, Worthington, OH (US); Timothy Haystead, Chapel Hill, NC (US); Philip Hughes, Chapel Hill, NC (US); Yazan Alwarawrah, Durham, NC (US)

(73) Assignees: Duke University, Durham, NC (US); Ohio State Innovation Foundation, Columbus, OH (US)

( * ) Notice: Subject to any disclaimer, the term of this patent is extended or adjusted under 35 U.S.C. 154(b) by 244 days.

(21) Appl. No.: 16/094,872

(22) PCT Filed: Apr. 20, 2017

(86) PCT No.: PCT/US2017/028584
§ 371 (c)(1),
(2) Date: Oct. 18, 2018

(87) PCT Pub. No.: WO2017/184844
PCT Pub. Date: Oct. 26, 2017

(65) Prior Publication Data
US 2019/0314376 A1    Oct. 17, 2019

Related U.S. Application Data

(60) Provisional application No. 62/325,887, filed on Apr. 21, 2016.

(51) Int. Cl.
| | | |
|---|---|---|
| *A61K 31/517* | (2006.01) | |
| *A61K 31/519* | (2006.01) | |
| *A61P 31/18* | (2006.01) | |
| *A61K 31/555* | (2006.01) | |

(52) U.S. Cl.
CPC .......... *A61K 31/519* (2013.01); *A61K 31/555* (2013.01); *A61P 31/18* (2018.01)

(58) Field of Classification Search
CPC .................................................. A61K 31/517
USPC ..................................................... 514/260.1
See application file for complete search history.

(56) References Cited

U.S. PATENT DOCUMENTS

| | | |
|---|---|---|
| 6,559,179 B1 | 5/2003 | Gaitanopoulos et al. |
| 2004/0138238 A1 | 7/2004 | Dhanoa et al. |
| 2005/0222175 A1 | 10/2005 | Dhanoa et al. |
| 2012/0277424 A1 | 11/2012 | Sim et al. |

OTHER PUBLICATIONS

PubChem, CID 16230362 (Create Date: Jul. 30, 2007) (URL: https://pubchem.ncbi.nlm.nih.gov/compound/16230362).

Adachi, A. et al., "Production of acquired immunodeficiency syndrome-associated retrovirus in human and nonhuman cells transfected with an infectious molecular clone" J. Virol. 59, 284 (1986).

Alo, P. et al. "Expression of fatty acid synthase (FAS) as a predictor of recurrence in stage I breast carcinoma patients." Cancer 77, 474-482, (1996).

Alwarawrah, Y. et al., "Fasnall, a selective FASN inhibitor, shows potent anti-tumor activity in the MMTV-Neu model of HER2+ breast cancer." Cell Chemical Biology, Jun. 2016, vol. 23, No. 6, pp. 678-688, Supplemental Information.

Ameer, F. et al. "De novo lipogenesis in health and disease." Metabolism: Clinical and Experimental 63, 895-902, (2014).

Aragones, G. et al., "Toll-like receptor-2 deficiency enhances non-alcoholic steatohepatitis." BMC Gastroenterol. 10, 92, (2010).

Bandyopadhyay, S. et al. "Mechanism of apoptosis induced by the inhibition of fatty acid synthase in breast cancer cells." Cancer Res. 66, 5934-5940, (2006).

Bligh, E.; Dyer, W. "A Rapid Method of Total Lipid Extraction and Purification" Can. J. Biochem. Physiol. 37, 911, (1959).

Brusselmans, K. et al. "The Lipogenic Switch in Cancer," In Mitochondria and Cancer (Springer New York), pp. 39-59, (2009).

Bryant, M.; Ratner, L. "Myristoylation-dependent replication and assembly of human immunodeficiency virus 1." Proc Natl Acad Sci. USA. 87:523-527, 1990.

Bushman, F. et al., "Host Cell Factors in HIV Replication: Meta-Analysis of Genome-Wide Studies. " PLoS Pathog. 5, e1000437, (2009).

Carlson, D. et al. "Fluorescence linked enzyme chemoproteomic strategy for discovery of a potent and selective DAPK1 and ZIPK inhibitor." ACS Chemical Biology 8, 2715-2723, (2013).

Chakravarthy, M. et al. ""New" hepatic fat activates PPARalpha to maintain glucose, lipid, and cholesterol homeostasis." Cell Metab. 1:309-322m 2005.

Chirala, S. et al. Fatty acid synthesis is essential in embryonic development: fatty acid synthase null mutants and most of the heterozygotes die in utero. Proc. Natl. Acad. Sci. USA., 100:6358-6363, 2003.

Chu, G. "Cellular responses to cisplatin. The roles of DNA-binding proteins and DNA repair." The Journal of Biological Chemistry, 269, 787-790, 1994.

Dorr, P. et al., "Maraviroc (UK-427,857), a potent, orally bioavailable, and selective small-molecule inhibitor of chemokine receptor CCR5 with broad-spectrum anti-human immunodeficiency virus type 1 activity." Antimicrob. Agents Chemother. 49, 4721-32, (2005).

Edmonds, T. et al., "Replication competent molecular clones of HIV-1 expressing Renilla luciferase facilitate the analysis of antibody inhibition in PBMC." Virology 408, 1, (2010).

(Continued)

*Primary Examiner* — Raymond J Henley, III
(74) *Attorney, Agent, or Firm* — Womble Bond Dickinson (US) LLP

(57) ABSTRACT

The present disclosure relates to a method for inhibiting Fatty Acid Synthase (FASN) with a FASN inhibitor, methods for treating cancer and viral infections with a FASN inhibitor, and compounds and compositions inhibiting FASN.

26 Claims, 28 Drawing Sheets
Specification includes a Sequence Listing.

(56) References Cited

OTHER PUBLICATIONS

Etienne, M. et al. "Pharmacokinetics of low-dose carboplatin and applicability of a method of calculation for estimating individual drug clearance." Annals of Oncology: Official Journal of the European Society for Medical Oncology /ESMO 14, 643-647, (2003).
Fadden, P. et al., "Application of chemoproteomics to drug discovery: identification of a clinical candidate targeting hsp90." Chem. Biol. 17, 686, (2010).
Felder, E. et al. "The generation of purinome-targeted libraries as a means to diversify ATP-mimetic chemical classes for lead finding." Molecular Diversity 16, 27-51, (2012).
Funabashi, H. et al., "Binding site of cerulenin in fatty acid synthetase." J. Biochem. 105, 751, (1989).
Graves, P. et al., "Discovery of novel targets of quinoline drugs in the human purine binding proteome." Mol. Pharmacol. 62, 1364, (2002).
Greseth M.D., Traktman P. "De novo fatty acid biosynthesis contributes significantly to establishment of a bioenergetically favorable environment for vaccinia virus infection." PLoS Pathog. 10:e1004021, 2014.
Hardwicke, M. et al. "A human fatty acid synthase inhibitor binds beta-ketoacyl reductase in the keto-substrate site." Nature Chemical Biology 10, 774-779, (2014).
Harland, S. et al. "Pharmacokinetics of cis-diammine-1,1-cyclobutane dicarboxylate platinum(II) in patients with normal and impaired renal function." Cancer Res. 44, 1693-1697, (1984).
Haystead, C. et al., "γ-Phosphate-linked ATP-Sepharose for the affinity purification of protein kinases." Eur. J. Biochem. 214, 459-67 (1993).
Haystead, T. "The purinome, a complex mix of drug and toxicity targets." Current Topics in Medicinal Chemistry 6, 1117-1127, (2006).
Haystead, T. et al. "Both insulin and epidermal growth factor stimulate lipogenesis and acetyl-CoA carboxylase activity in isolated adipocytes. Importance of homogenization procedure in avoiding artefacts in acetyl-CoA carboxylase assay." The Biochemical Journal 234, 279-284, (1986).
Haystead, T. et al. "Effects of the tumour promoter okadaic acid on intracellular protein phosphorylation and metabolism." Nature 337, 78-81, (1989).
Heaton, N. et al., "Dengue virus nonstructural protein 3 redistributes fatty acid synthase to sites of viral replication and increases cellular fatty acid synthesis." Proc. Natl. Acad. Sci. USA 107, 17345, (2010).
Howe, M. et al. Identification of an alloHowe, M. et al. "Identification of an allosteric small-molecule inhibitor selective for the inducible form of heat shock protein 70." Chemistry & Biology 21, 1648-1659, (2014).
Huang et al. "Hepatitis C virus replication is modulated by the interaction of nonstructural protein NS5B and fatty acid synthase." J. Virol. 87:4994-5004, 2013.
Hughes, P. et al. "A highly selective Hsp90 affinity chromatography resin with a cleavable linker." Bioorganic & Medicinal Chemistry 20, 3298-3305, (2012).
Iwanaga, T. et al. "Dynamic protein palmitoylation in cellular signaling." Progress in Lipid Research 48, 117-127, (2009).
Kaluzny, M. et al. "Rapid separation of lipid classes in high yield and purity using bonded phase columns." Journal of Lipid Research 26, 135-140, (1985).
Knapp, M. et al. "Targeting cancer: the challenges and successes of structure-based drug design against the human purinome." Current Topics in Medicinal Chemistry 6, 1129-1159, (2006).
Knox, R. et al. "Mechanism of cytotoxicity of anticancer platinum drugs: evidence that cis-diamminedichloroplatinum(II) and cis-diammine-(1,1-cyclobutanedicarboxylato)platinum(II) differ only in the kinetics of their interaction with DNA." Cancer Res. 46, 1972-1979, (1986).
Kridel, S. et al., "Orlistat is a novel inhibitor of fatty acid synthase with antitumor activity." Cancer Res. 64, 2070-2075, (2004).

Kuhajda, F. et al. "Synthesis and antitumor activity of an inhibitor of fatty acid synthase." Proceedings of the National Academy of Sciences USA, 97, 3450-3454, (2000).
Kuhajda, F., "Fatty-acid synthase and human cancer: new perspectives on its role in tumor biology." Nutrition. 2000; 16:202-208.
Landis-Piwowar, K. et al. "A novel prodrug of the green tea polyphenol (-)-epigallocatechin-3-gallate as a potential anticancer agent." Cancer Res. 67, 4303-4310, (2007).
Li, H. et al. "Myristoylation is required for human immunodeficiency virus type 1 Gag-Gag multimerization in mammalian cells." J. Virol. 81:12899-12910, 2007.
Li, Y. et al., "Fatty Acid Synthase Expression Is Induced by the Epstein-Barr Virus Immediate-Early Protein BRLF1 and Is Required for Lytic Viral Gene Expression." J. Virol. 78, 4197-4206, (2004).
Lindwasser, O. W., Resh, M. D. "Myristoylation as a target for inhibiting Hiv assembly: unsaturated fatty acids block viral budding." Proc. Natl. Acad. Sci. USA. 99:13037-13042, 2002.
Liu, H. et al., Biochemistry, molecular biology, and pharmacology of fatty acid synthase, an emerging therapeutic targe and diagnosis/ prognosis marker. Int J Biochem Mol Biol. Jul. 18, 2010;1(1):69-89.
Lorizate, M. et al., "Comparative lipidomics analysis of HIV-1 particles and their producer cell membrane in different cell lines." Cell Microbiol. 15, 292-304, (2013).
Maier, T. et al. "The crystal structure of a mammalian fatty acid synthase." Science 321, 1315-1322, (2008).
Martin, M. et al. "Carboplatin: an active drug in metastatic breast cancer." Journal of Clinical Oncology: Official Journal of the American Society of Clinical Oncology 10, 433-437, (1992).
Martin-Acebes, M. et al., "West Nile Virus Replication Requires Fatty Acid Synthesis but Is Independent on Phosphatidylinositol-4-Phosphate Lipids." PLoS ONE 6, e24970, (2011).
Menendez, J. et al., "Fatty acid synthase and the lipogenic phenotype in cancer pathogenesis." Nat. Rev. Cancer 7, 763-77, (2007).
Miyaguchi, Y. et al. "Simple method for isolation of glyceraldehyde 3-phosphate dehydrogenase and the improvement of myofibril gel properties." Animal Science Journal = Nihon Chikusan Galdcaiho 82, 136-143, (2011).
Muller, W. et al. "Single-step induction of mammary adenocarcinoma in transgenic mice bearing the activated c-neuoncogene." Cell 54, 105-115, (1988).
Muratsubaki, H. et al. Rapid purification of yeast cytoplasmic fumarate reductase by affinity chromatography on blue sepharose CL-6B. Prep. Biochem. 24, 289-296, (1994).
Murray, J. et al. "Targeting the purinome." Methods Mol. Biol. 575, 47-92, (2009).
Oliveras, G. et al. "Novel anti-fatty acid synthase compounds with anti-cancer activity in HER2+ breast cancer." Annals of the New York Academy of Sciences 1210, 86-92, (2010).
Ono, A. et al., "Plasma membrane rafts play a critical role in HIV-1 assembly and release." Proc. Natl. Acad. Sci. USA 8, 13925-13930, (2001).
Oslob, J. et al. "Imidazopyridine-Based Fatty Acid Synthase Inhibitors That Show Anti-HCV Activity and in Vivo Target Modulation." ACS Medicinal Chemistry Letters 4, 113-117, (2013).
Pal, R. et al. "Processing of the structural proteins of human immunodeficiency virus type 1 in the presence of monensin and cerulenin." Proc. Natl. Acad. Sci. USA. 85:9283-9286, 1988.
Pizer, E. et al. "Malonyl-coenzyme-A is a potential mediator of cytotoxicity induced by fatty-acid synthase inhibition in human breast cancer cells and xenografts." Cancer Res. 60, 213-218, (2000).
Puig, T. et al. "Novel Inhibitors of Fatty Acid Synthase with Anticancer Activity." Clinical Cancer Research: An Official Journal of the American Association for Cancer Research 15, 7608-7615, (2009).
Puig, T. et al. "A novel inhibitor of fatty acid synthase shows activity against HER2+ breast cancer xenografts and is active in anti-HER2 drug-resistant cell lines." Breast Cancer Research 13, R131, (2011).
Resh, M., "Fatty acylation of proteins: new insights into membrane targeting of myristoylated and palmitoylated proteins." Biochim. Biophys. Acta 1451, 1-16, (1999).

(56) References Cited

OTHER PUBLICATIONS

Richardson, R. et al. "Novel antagonists of the thioesterase domain of human fatty acid synthase." Molecular Cancer Therapeutics 6, 2120-2126, (2007).

Richardson, R. et al., "Synthesis of Novel β-Lactone Inhibitors of Fatty Acid Synthase." J. Med Chem. 51, 5285-5296, (2008).

Russell, E. et al., "The Genetic Bottleneck in Vertical Transmission of Subtype C HIV-1 Is Not Driven by Selection of Especially Neutralization-Resistant Virus from the Maternal Viral Population." J. Virol. 85, 8253-62, (2011).

Safi, R. et al. "Copper signaling axis as a target for prostate cancer therapeutics." Cancer Res. 74, 5819-5831, (2014).

Schneider, J. et al. "Macrophage fatty-acid synthase deficiency decreases diet-induced atherosclerosis." J. Biol. Chem. 285:23398-23409, 2010.

Smith, S., "The animal fatty acid synthase: one gene, one polypeptide, seven enzymes." FASEB J. 8, 1248-1259, (1994).

Sul, H. et al., "Nutritional and Hormonal Regulation of Enzymes in Fat Synthesis: Studies of Fatty Acid Synthase and Mitochondrial Glycerol-3-Phosphate Acyltransferase Gene Transcription." Ann. Rev. Nutr. 18, 331-351, (1998).

Swinnen, J. et al. "Increased lipogenesis in cancer cells: new players, novel targets." Current Opinion in Clinical Nutrition and Metabolic Care 9, 358-365, (2006).

Thupari, J. et al. "C75 increases peripheral energy utilization and fatty acid oxidation in diet-induced obesity." Proceedings of the National Academy of Sciences of the United States of America 99, 9498-9502, (2002).

Turrado, C. et al. "New synthetic inhibitors of fatty acid synthase with anticancer activity." Journal of Medicinal Chemistry 55, 5013-5023, (2012).

Vazquez, M. et al. "Discovery of GSK837149A, an inhibitor of human fatty acid synthase targeting the beta-ketoacyl reductase reaction." The FEBS Journal 275, 1556-1567, (2008).

Wakil, S. "Fatty acid synthase, a proficient multifunctional enzyme." Biochemistry 28:4523-4530, (1989).

Wilsky, S. et al., "Inhibition of fatty acid synthase by amentoflavone reduces coxsackievirus B3 replication." Arch. Virol. 157, 259-69, (2012).

Yang, Y. et al. "Activation of fatty acid synthesis during neoplastic transformation: role of mitogen-activated protein kinase and phosphatidylinositol 3-kinase." Experimental Cell Research 279, 80-90, (2002).

Yang, W. et al. "Fatty acid synthase is up-regulated during hepatitis C virus infection and regulates hepatitis C virus entry and production." Hepatology 48:1396-1403, 2008.

Yoshii, Y. et al., "Fatty acid synthase is a key target in multiple essential tumor functions of prostate cancer: uptake of radiolabeled acetate as a predictor of the targeted therapy outcome." PLoS ONE 8(5), e64570, (2013).

FIG. 6 de novo fatty acid synthesis. Many tumors are dependent on de novo fatty acid synthesis as a source of long chain fatty acids to maintain growth and interdicting at key steps in this pathway may have therapeutic benefit. FASN up-regulation is correlated with tumor aggressiveness. FASN is upregulated in numerous cancers, including breast cancer, melanoma, and hepatocellular carcinoma (Menendez et al., 2007). Like many essential metabolic pathways under complex homeostatic regulation, the consequences and adaptive responses of acute or chronic inhibition of essential enzymes such as FASN in vivo are not fully understood. Owing to its low level expression and its association with both cancer and enveloped virus replication, FASN is an attractive therapeutic target. Cellular FASN expression is highly regulated, and in response to physiological stresses such as starvation, lactation or pathological states, its expression can change dramatically (Sul et al., 1998). Although studies in mice indicate that FASN is required for embryonic development (Chirala et al., 2003), liver or macrophage-specific FASN knockout mice are viable (Chakravathy et al., 2005; Schneider et al., 2010).

FATTY ACID SYNTHASE INHIBITORS

CROSS-REFERENCE TO RELATED APPLICATIONS

This application is a national phase of International App. No. PCT/US2017/028584, filed Apr. 20, 2017, which International Application was published by the International Bureau in English on Oct. 26, 2017, and claims priority to U.S. Provisional Application No. 62/325,887, filed Apr. 21, 2016, the entirety of each of which is hereby incorporated by reference.

SEQUENCE LISTING

The instant application contains a Sequence Listing which has been submitted via EFS-Web and is hereby incorporated by reference in its entirety. Said ASCII copy, created on Oct. 15, 2018, is named SeqList 1180_ST25.txt, and is 915 bytes in size.

STATEMENT REGARDING FEDERALLY SPONSORED RESEARCH OR DEVELOPMENT

This invention was made with Government Support under Grant Nos. AI090644 and 1R01-AI089526-04 awarded by the National Institutes of Health. The Government has certain rights in the invention.

FIELD OF THE INVENTION

The present disclosure provides a potent and selective fatty acid synthase (FASN) inhibitor, HS-106. Further disclosed is that HS-106 has potent anti-tumor activity in various breast cancer cell lines. Further disclosed is that FASN is a novel host antiviral target, and that HS-106 inhibits HIV replication with minimal host cell toxicity.

BACKGROUND OF THE INVENTION

Fatty acid synthase 1 (FASN) catalyzes the final steps leading to the synthesis of long chain tatty acids in vive. FASN is a 270 kDa, multifunctional, cytosolic enzyme that uses NADPH to condense acetyl-CoA and malonyl-CoA into palmitate (Liu et al., 2010). FASN is considered an attractive target for cancer therapy due to the selective dependence of many tumors on de novo fatty acid synthesis. Many tumors are dependent on In humans, de novo fatty acid synthesis is active in a limited number of tissues such as liver, adipose, cycling endometrium and lactating mammary gland. This contrasts with the other bodily tissues which largely meet their fatty acid requirements from dietary sources (Brusselmans and Swinnen, 2009) (Iwanaga et al., 2009) (Swinnen et al., 2006). However, some pathological conditions promote cells to become dependent on de novo fatty acid synthesis including solid tumors, leukemic cells and host cells of certain viruses (Ameer et al., 2014).

FASN catalyzes the complete synthesis of palmitate from acetyl-CoA and malonyl-CoA into long-chain saturated fatty acids (FAs). FASN is a multifunctional enzyme that synthesizes FA chains two-carbons at a time, each donated from malonyl-CoA. The active form of FASN is composed of a homo-dimer where each monomer has seven different catalytic domains. These domains include the acyl carrier (ACP) protein which is responsible substrate channeling from one domain to another, the ketoacyl synthetase domain (KAS) which catalyze the condensation step, the ketoacyl reductase (KR) and enoyl reductase (ER) which both are responsible for saturating the acyl chain, the dehydratase (DH) domain which is responsible for removing a water molecule from the acyl chain between the two reduction steps, Malonylacetyl transferase (MAT) domain which catalyze the transfer of both malony-CoA and acetyl CoA, and the thioesterase domain (TE), which clips the palmitate off the enzyme after reaching the desired acyl-chain length (Maier et al., 2008). Palmitic acid (16:0) can be metabolized further by Q-oxidation into myristic acid (14:0), or other long chain FAs (Liu et al., 2010). Long chain FAs are essential components of lipid bilayers, store energy liberated by β-oxidation, and FAs can be covalently attached to proteins as a means to control protein subcellular localization (Wakil, 1989).

The human purinome consists of ~1,500 proteins that bind and use purines such as ATP, NADH, and NADPH (Fadden et al., 2010). Almost all synthetic processes within the cell, including transcription, protein folding, and metabolite synthesis, require purine-utilizing proteins. By virtue of their purine binding pockets, purinome proteins are highly druggable, and many existing drugs target purine-using enzymes (e.g. methotrexate, warfarin, statins, protein kinase inhibitors, antiretrovirals) (Haystead, 2006). FASN has seven sequential catalytic activities and uses two co-factors, NADPH and co-enzyme A, to transfer two carbon units to a growing FA chain (Wakil, 1989) until the final product, palmitic acid (16:0) is released. Three of the FASN enzymatic activities (ketoacyl reductase, enoyl reductase and malonyl/acetyl transferase) use purine-containing co-factors in the form of NADPH, acetyl CoA and malonyl CoA. Importantly, inhibitors targeting purine-utilizing enzymes are generally not lipophilic and have formed the basis of many drugs in clinical use from reverse transcriptase inhibitors to the newer cutting edge inhibitors targeting protein kinases or heat shock proteins (Felder et al., 2012; Haystead, 2006; Knapp et al., 2006; Murray and Bussiere, 2009). In the last two decades, FASN has been considered a potential therapeutic target for the treatment of metabolic syndrome and numerous malignancies (Puig et al., 2011; Yoshii et al., 2013).

One of the common themes amongst current FASN inhibitors is a mechanism of action favoring competition with substrate intermediates over cofactor binding. Even in the case of GSK2194069, despite acting on f-ketoacyl reductase step, the triazolone is only competitive with trans-1-decalone binding and uncompetitive with NADPH (Hardwicke et al., 2014). Inhibitors targeting the FASN co-factor domain therefore remain largely unexplored. Targeting of the substrate domains may in part explain the toxicities and lack of efficacy in vive of the majority of FASN inhibitors, since in order to act competitively the molecules are lipid like in nature. A second concern relates to the broader physiological consequences of selectively inhibiting FASN in vivo, either acutely or chronically. The de novo fatty acid synthesis pathway is highly regulated at several steps and therefore highly prone to compensatory adaptive responses that would potentially mitigate the efficacy of any selective FASN inhibitor in vivo. Likely compensations could include increased over expression of FASN itself, increased uptake of exogenous dietary lipids, alteration in expression of enzymes regulating malonyl CoA levels, such as acetyl CoA carboxylase or malonyl CoA decarboxylase or even switching of the cell to a glycolytic phenotype.

In breast cancer, the level of FASN expression is correlated with tumor progression, where high FASN expression leads to more tumor aggressiveness and poor prognostic outcome (Alo et al., 1996). Inhibiting FASN activity in vitro by pharmacological means or the message level siRNA has been shown to stop cancer cell growth and induce apoptosis. As a consequence, many research groups have tried to exploit FASN as a target for cancer by developing inhibitors including C75, C93, epigallocatechin gallate (EGCG), G28UCM, orlistat, GSK2194069 and GSK837149A (Kuhajda et al., 2000) (Thupari et al., 2002) McFadden et al., 2005; Orita et al., 2007; Ueda et al., 2009; Zhou et al., 2007). (Tian, 2006; Wang and Tian, 2001 (Landis-Piwowar et al., 2007; Oliveras et al., 2010; Puig et al., 2009; Turrado et al., 2012) (Puig et al., 2011) (Hardwicke et al., 2014; Vazquez et al., 2008). Despite these efforts, however, the majority of FASN inhibitors have failed to even advance to animal efficacy studies largely due selectivity issues in viva resulting in unexpected toxicities. Current anti-FASN scaffolds include C75 (Kuhadja, 2000) and Cerulenin (Funabashi et al., 1989), which are lipid-like and contain reactive epoxides, or are based on natural products such as Epigallocatechin gallate (EECG). These scaffolds are not in clinical use because they are either unselective (Liu et al., 2010) or with low bioavailability (Kridel et al., 2004). The only FASN inhibitor advanced to clinical trial for the treatment of advanced solid tumors to date is the FASN inhibitor TVB-2640. This molecule is based on a potent imidazopyridine scaffold and also has anti-hepatitis C virus (HCV) activity (Oslob et al., 2013). Therefore, a need remains for additional selective FASN inhibitors for the treatment of cancers.

Viruses repurpose host cellular machinery to produce progeny. The development of CCR5-based antiviral therapy and the results of several siRNA-based screens that identified host proteins required for HIV replication highlight both the utility and the potential to drug host proteins (Dorr et al., 2005, Bushman et al., 2009). HIV-1 relies on host systems to replicate, and intracellular host proteins represent an underdeveloped pool of therapeutic targets that do not evolve as rapidly as viral proteins. Drugging host proteins could have several advantages over viral targets, including a high barrier to drug resistance (human proteins evolve at slower rates than viral proteins), and the potential to develop a pan-antiviral drug (if several viruses require the same host pathway). The challenge is to identify a pathway that is dispensable to the host but critical for viral replication. Therefore, a need exists for identification of such pathways and their inhibitors for the development of new antiviral drugs.

SUMMARY OF THE INVENTION

Herein is disclosed that the anti-neoplastic activity of HS-106 is due to the induction of apoptosis resulting from CPT-1 inhibition, ceramide accumulation, and changes in lipid raft composition, all of which can be rescued by ACC inhibition rather than exogenous palmitate supplementation, which is deviated into neutral lipids instead of phospholipids.

Accordingly, in one aspect the invention relates to a method of inhibiting Fatty Acid Synthase (FASN) with a FASN inhibitor that binds to the FASN purine-binding cofactor domain, the method comprising contacting cells that express FASN with an inhibitor that binds to the FASN purine-binding cofactor domain.

In another aspect, the invention relates to a method of promoting apoptosis in a cancer cell dependent on FASN activity, the method comprising contacting the cells with an inhibitor that binds to the FASN purine-binding cofactor domain.

In another aspect, the invention relates to method of treating cancer in a subject, the method comprising administering to the subject in need thereof, a therapeutically effective amount of a FASN inhibitor that binds to the FASN purine-binding cofactor domain.

In another aspect, the invention relates to method of inhibiting viral replication in cells dependent on FASN expression, the method comprising contacting the cells with an inhibitor that binds to the FASN purine-binding cofactor domain.

In another aspect, the invention relates to method of treating a viral infection in a subject, the method comprising administering to the subject in need thereof, a therapeutically effective amount of a FASN inhibitor that binds to the FASN purine-binding cofactor domain.

In another aspect, the invention relates to pharmaceutical composition comprising (N-(1-benzylpyrrolidin-3-yl)-5,6-dimethylthieno[2,3-d]pyrimidin-4-amine, or a pharmaceutically acceptable salt thereof, and a pharmaceutically acceptable carrier.

In another aspect, the invention relates to the compound (R)—(N-(1-benzylpyrrolidin-3-yl)-5,6-dimethylthieno[2,3-d]pyrimidin-4-amine or a pharmaceutically acceptable salt thereof.

In another aspect, the invention relates to the compound (S)—(N-(1-benzylpyrrolidin-3-yl)-5,6-dimethylthieno[2,3-d]pyrimidin-4-amine or a pharmaceutically acceptable salt thereof.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

The foregoing aspects and other features of the disclosure are explained in the following description, taken in connection with the accompanying drawings, herein:

FIG. 6 is a tabular view of the quantified lipids with more than two-fold change. The quantified lipids with more than two fold change and p-value <0.01 were examined and identified with endogenous standards or given putative identifications based on retention time, accurate mass, and fragmentation where available (e.g. diacylglycerols, Ceramides, and glycerophospholipids).

DETAILED DESCRIPTION OF THE INVENTION

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

As used herein, the terms "HS-106" and "Fasnall" are interchangeable, both referring to the compound N-(1-benzylpyrrolidin-3-yl)-5,6-dimethylthieno[2,3-d]pyrimidin-4-amine.

Unless otherwise defined, all technical terms used herein have the same meaning as commonly understood by one of ordinary skill in the art to which this disclosure belongs.

Identification of FASN Inhibitors

Figure 1:
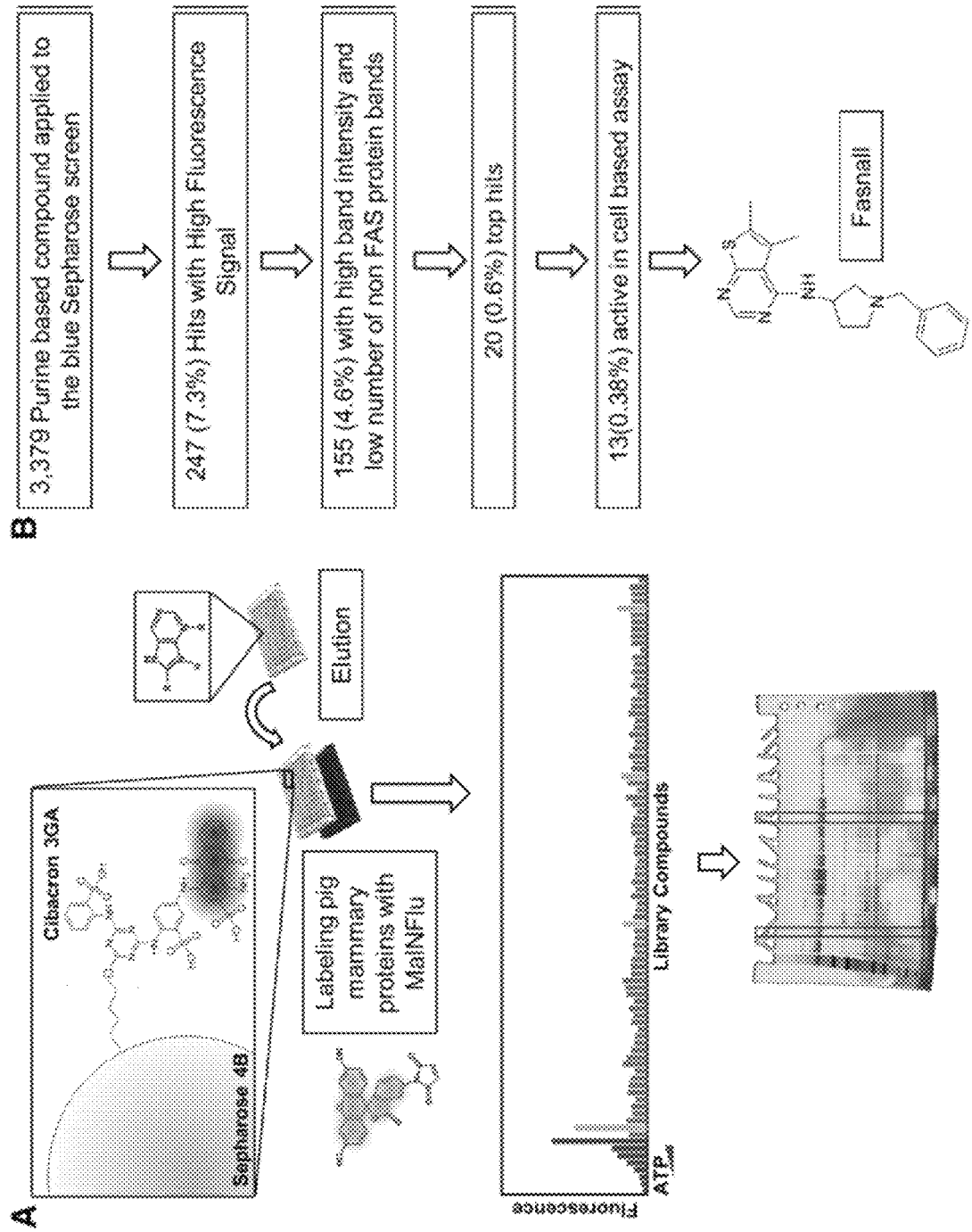
FIG. 1 is a cartoon illustration of the discovery of the FASN inhibitor HS-106. The ability of cibacron blue sepharose to bind FASN was utilized in screening for compounds that can bind FASN, fluorescein labeled FASN was used to quantify the ability of the compounds to elute FASN from the resin then the eluents with high fluorescence is run on SDS-PAGE were the eluted proteins was identified by mass spectrometry. (A). Cibacron blue Sepharose was incubated with porcine lactating mammary gland extracts (a rich source of FASN), washed, and bound proteins were labeled with fluorescein. A small molecule library of druggable molecules with structural similarity to any purine or known purine analog scaffold was assembled and tested for the ability of each molecule to compete fluorescein labeled proteins off cibacron blue resin, proteins from the eluents that had high fluorescence intensity were separated by SDS-PAGE and silver stained then proteins were identified by MS. (B). The screen of 3,379 purine-based compounds identified 247 hits with high fluorescent signal. Of the 247 hits, 155 were selected by virtue of both a high FASN-intensity and a low number of non-FASN protein bands. The 20 most selective compounds were tested for anti-FASN activity in a $^3$H glucose incorporation assay and the molecule with the highest activity (HS-106) was selected for further profiling.
Figure 9:
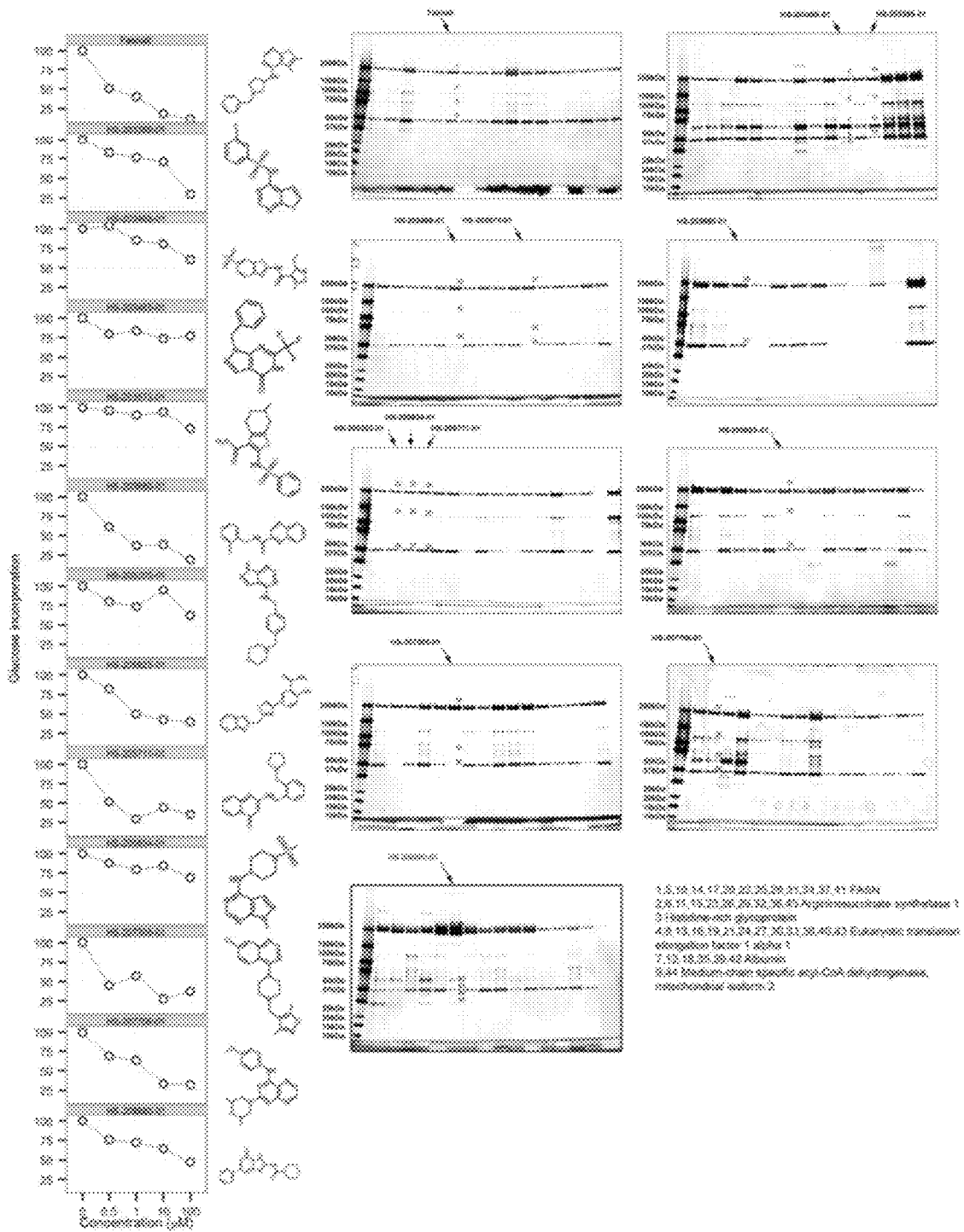
FIG. 9 illustrates the top screening hits and their activity in glucose incorporation into lipids and elution profile. From the 155 hits with highest FAS band intensity and low number of non-FAS bands, 20 molecules were selected and only 13 selected for purchase. These molecules were tested for their ability to inhibit the incorporation of tritiated glucose into lipids.
Figure 10:
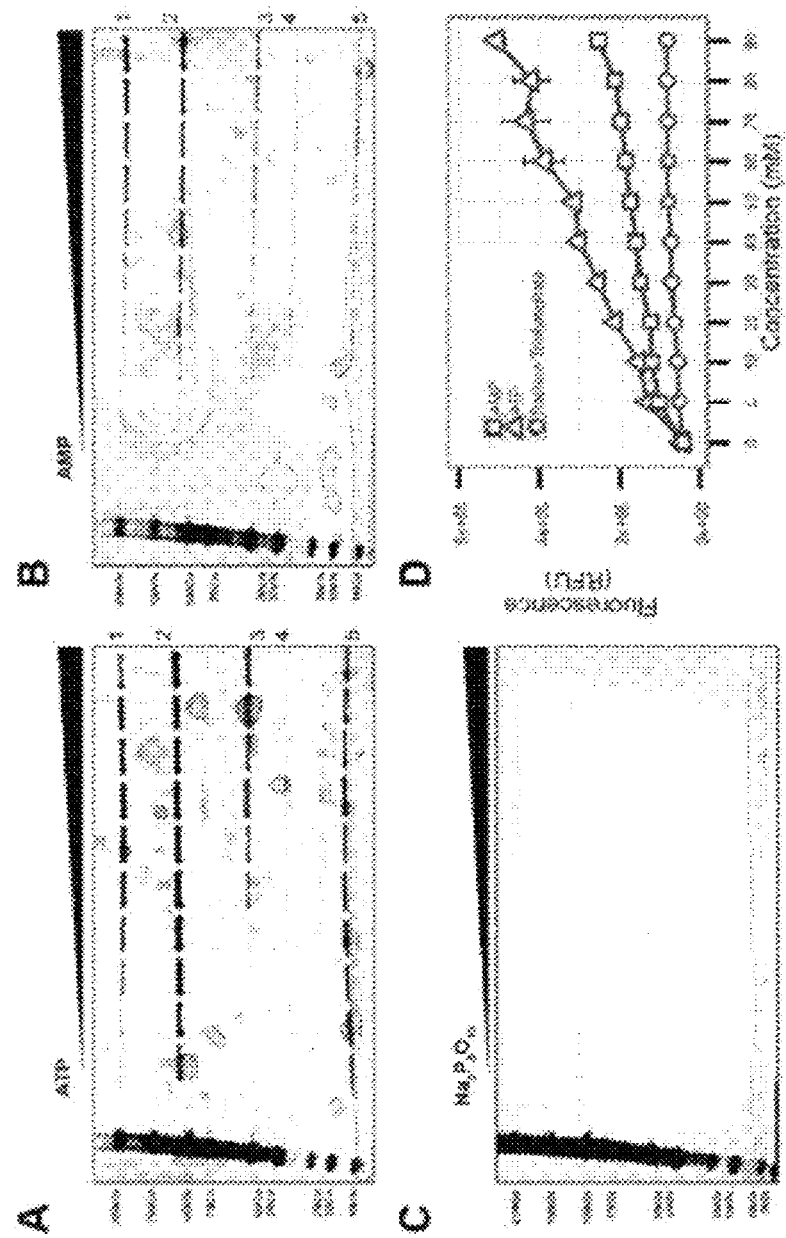
FIG. 10 illustrates the elution of fluorescein labeled proteins. Labeled proteins can be eluted from Cibacron Blue Sepharose with Adenine Nucleotides. Lactating pig mammary gland homogenate where applied to blue Sepharose resin then washed with buffer and labeled with the Thiol-Reactive probe Fluorescein-5-maleimide. Then, the resin was washed with 5 mM NAD solution to remove dehydrogenases and excess Fluorescein. The bonded proteins were eluted with different Adenine Nucleotides. (A, B and C) the eluted proteins separated by SDS-PAGE and stained with silver. These proteins were identified with mass spectrometry: 1-Fatty acid synthase 2-ATP citrate Lyase 3-Eukaryotic translation elongation factor 1 alpha 1.4-L-lactate dehydrogenase. 5-Nucleoside diphosphate kinase B. (D) Fluorescence of the eluted proteins, showing a concentration dependent increase in the fluorescence signal.

To specifically identify inhibitors of FASN targeting its nucleotide binding pockets Cibacron blue Sepharose was utilized. This medium has been used previously to purify NAD and NADP binding proteins from crude tissues extracts (Miyaguchi et al., 2011; Muratsubaki et al., 1994). FASN enriched extract from lactating pig mammary gland was bound to the resin and labeled with cysteine reactive fluorescein. Having established that labeled FASN could be competitively released from the resin with adenine nucleotides (FIG. 10), a subsequent screen of the bound enzyme against a single concentration of an in-house small molecule library comprising compounds with structural similarity to any purine or known purine analog scaffold (Carlson et al., 2013) was performed. Of the 3,379 compounds screened, 247 were found to yield a fluorescent signal at 488 $nm_{ex}$/522 $nm_{em}$ (FIG. 1). One hundred and fifty-five of the molecules selectively eluted FASN from the resin, and 20 potential lead compounds were progressed according to their FASN selectivity (assessed with SDS-PAGE, silver staining and mass spectrometry). These twenty compounds were reduced to 13 based on the absence of any obvious chemical liabilities. Next, the molecules were tested for their ability to inhibit FASN activity in a HepG2 cell based assay that measured the incorporation of $^3$H glucose into lipids (FIG. 1B and FIG. 9).

Figures 2A, 2B, 2C, 2D:
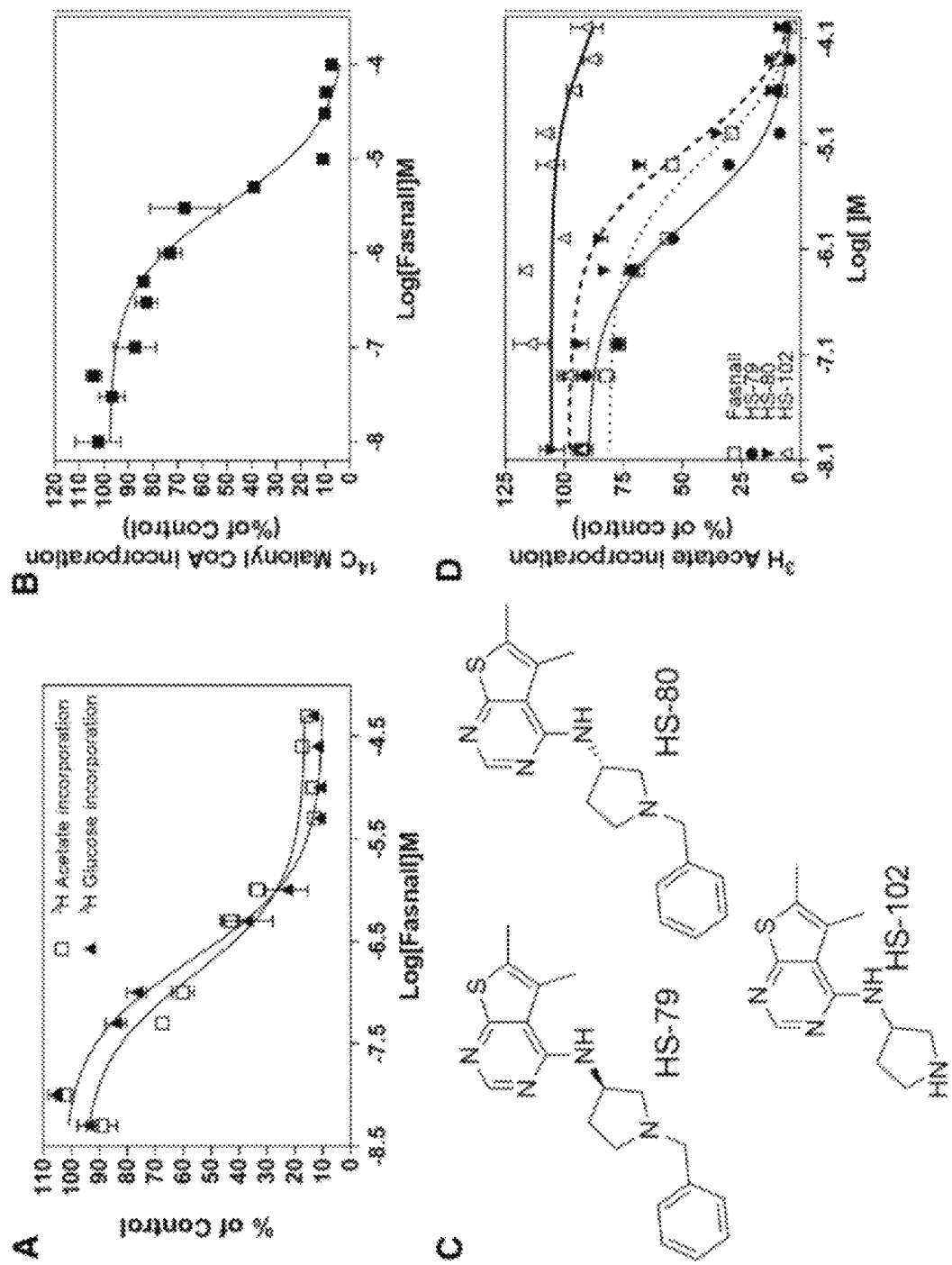
FIG. 2 as a graphic illustration of the structures and activities of HS-106 and related compounds. (A). HS-106 inhibited the incorporation of both tritiated acetate ($IC_{50}$ 147 nM) and tritiated glucose ($IC_{50}$ 213 nM) into lipids in HepG2. (B). HS-106 inhibited the human purified FAS activity of $^{14}$C Malonyl CoA incorporation into lipids with an $IC_{50}$ 3.71 μM. (C). Structures of analog HS-102 and enantiomers of HS-106 (HS-79 and HS-80). (D). HS-106 and its enantiomers, HS-79 and HS-80, inhibit the incorporation of tritiated acetate into lipids.
Figure 2E:
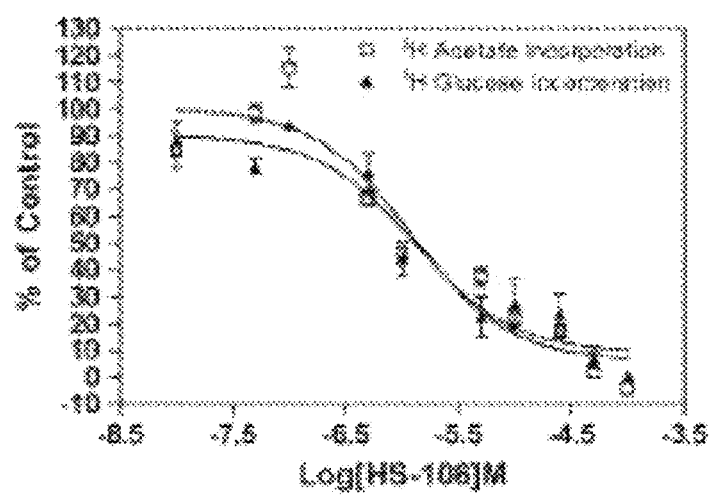
Figure 3:
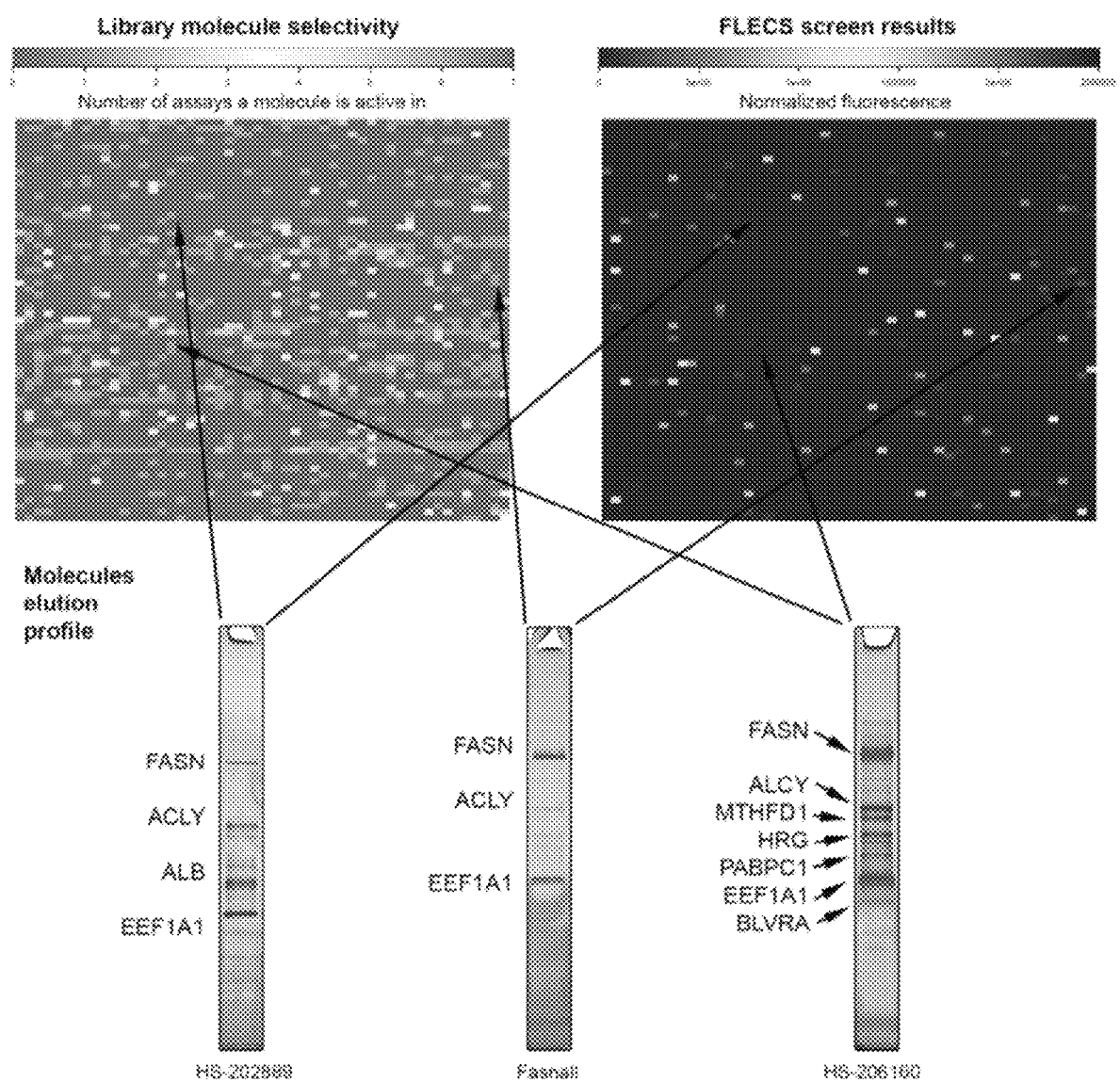
FIG. 3 is a graphical illustration of the selectivity of HS-106 and library compounds. Individual compounds were assayed for their ability to elute proteins from Cibacron blue resin. Blue-red color spectrum indicates protein concentration, as measure by fluorescence (see FLECS methods). SDS-PAGE and mass spectrometry analysis showed that HS-106 selectively elutes FASN compared with strong (HS-206160) and weak (HS-202889) hits. Bottom (red graph). Compound library was screened for inhibitory activity against the following enzymes: ACC, ZipK, AMPKα, AMPKγ, TRAP1, HSP70, NS5, and IRAK2; HS-106 was a potent inhibitor of FASN (only).

Of the 13 molecules tested, HS-106 was the most potent inhibitor. In more detailed cell based assays, HS-106 potently blocked both acetate and glucose incorporation into total lipids, with $IC_{50}$ values of 147 nM and 213 nM, respectively in HepG2 cells and about 1.50 µM with Acetate and glucose (1.66 µM) as a tracers in the HER2+ BT474 breast cancer cell line (FIGS. 2A and 2E). Subsequently, direct inhibition of FASN was confirmed using the purified human enzyme isolated from the BT474 cell line ($IC_{50}$=3.71 µM, FIG. 2B). To confirm selectivity of HS-106, data derived from prior screens against the house library (Carlson et al., 2013; FIG. 3) was analyzed. None of the previously screened proteins (ACC, Hsp90, Hsp70, TRAP-1, DAP kinase 3 (ZIPK), IRAK 2, AMPK alpha and gamma subunits, NEK9, dengue nonstructural protein 5 (NS5) malarial kinase PfPK9, and HSF-1) were targeted by HS-106.

HS-106 Antineoplastic Activity

In liver and breast tumor cells, HS-106 was able to inhibit both acetate and glucose incorporation into lipids. The sensitivity of breast cancer cell lines to inhibition of glucose incorporation into lipids by HS-106 was shown to vary based on the expression level of FASN as well as other enzymes directly involved in fatty acid synthesis. Consistent with a dependency of aggressive breast cancer cell lines on oxidative metabolism, HS-106 inhibited cell proliferation in triple negative, ER positive and Her2 positive breast tumor cells lines. In contrast, anti-proliferative activity of HS-106 was lower in the non-tumorigenic cell line MCF10A, which also has lower dependence on FASN activity (Yang et al., 2002). Global lipidomic studies with HS-106 showed selective inhibition of FASN profoundly alters cellular lipid profiles, sharply increasing ceramides, diacylglycerols and unsaturated fatty acids as well increasing exogenous palmitate uptake and neutral lipid formation. Whereas uptake of the latter lipids may represent compensatory responses to maintain cellular growth rates, the induction of ceramides promotes growth arrest and cell death. Consistent with this mechanism of action HS-106 showed potent anti-tumor activity in the MMTV Neu model of HER2+ breast cancer, particularly when combined with Carboplatin.

Mechanistic Evaluation of Apoptosis by FASN Inhibition

Lipidomics data analysis combined with the rescue experiments provided insights into the mechanism by which FASN inhibition may induce tumor cell apoptosis. HS-106 treatment was found to induce an increase in ceramides, diacylglycerols and saturated fatty acids. Ceramide accumulation is consistent with an inhibition of CPT-1 and induction of sphingomyelinase activity. Accumulation of ceramide reflects an increase in malonyl CoA concentration which inhibits CPT-1 activity (Pizer et al., 2000) while induction of sphingomyelinase indicates a translocation of sphingomyelin to the inner leaflet of the plasma membrane. There are two main pathways by which diacylglycerols can be formed; by de novo synthesis from glycerol and fatty acids, which increases when there are large quantities of these precursors; and from the lipolysis of PIP2. While not wishing to be bound by theory, but based on the present characterization of HS-106, the former pathway would be favored since inhibition of the fatty acid synthesis pathway in general leads to the glucose being diverted into the synthesis of glycerol (Haystead et al., 1989). When combined with the uptake of fatty acids from the media and the inhibition of CPT-1, these conditions favor an increase in diacylglycerols abundance. The palmitate uptake experiment confirms the previous finding by showing the partitioning of palmitate into neutral lipids rather than phospholipids, which explains the inability of palmitate to completely rescue HS-106 induced apoptosis in contrast to inhibiting ACC by TOFA which stops malonyl CoA accumulation and prevents CPT-1 inhibition. Collectively these data therefore suggest a mechanism by which FASN inhibition can induce anti-proliferative activity in vive in spite of the fatty acids provided from circulation.

This ability of HS-106 to induce apoptosis was confirmed by Annexin V assay. When combining this assay results with the accumulation of Ceramides, HS-106 inhibition of de novo fatty acid synthesis and the uptake of different types of polyunsaturated fatty acids from the media induces changes in the plasma membrane composition that leads to the translocation of phosphatidylserine and phosphatidylcholine from the inside of the membrane to the outside while sphingomyelin is internalized. This event is noteworthy due to its effect on lipid raft structures which can alter the representation of receptor tyrosine kinases on the cell surface, especially HER2 in the case of BT474 cells.

In Vivo Evaluation of HS-106

In contrast to most FASN inhibitors, HS-106 is well tolerated in mice and does not induce any overt weight loss or any change in feeding behavior. Even on a conservative twice weekly dosing regimen, HS-106 reduced tumor size in both the MMTV Neu and C3Tag models, and had a profound effect on median survival. Moreover, combining HS-106 with Carboplatin synergistically reduced tumor volumes and impacted survival over the first 40 days of combination treatment. Although, overall survival was not extended beyond HS-106 alone, the dramatic early response to the combination has clinical relevance. Normally, Carboplatin treatment is restricted to 21 days in patients due to its toxicity and tendency to develop resistant tumors when used over the longer term. The disclosed pharmacokinetic study shows that there is room to increase HS-106 dosing to improve its performance in vivo. The compound is rapidly cleared from plasma and tissues which indicates that it's possible to increase the dosing schedule from twice weekly to at least a daily regimen. HS-106 may therefore enable significant reduction of the Carboplatin dose. This may increase the combined drugs' efficacy while reducing the toxicity of the latter compound.

Evaluation of Purine-Binding Proteins Regulated by HIV-1

Figure 21:
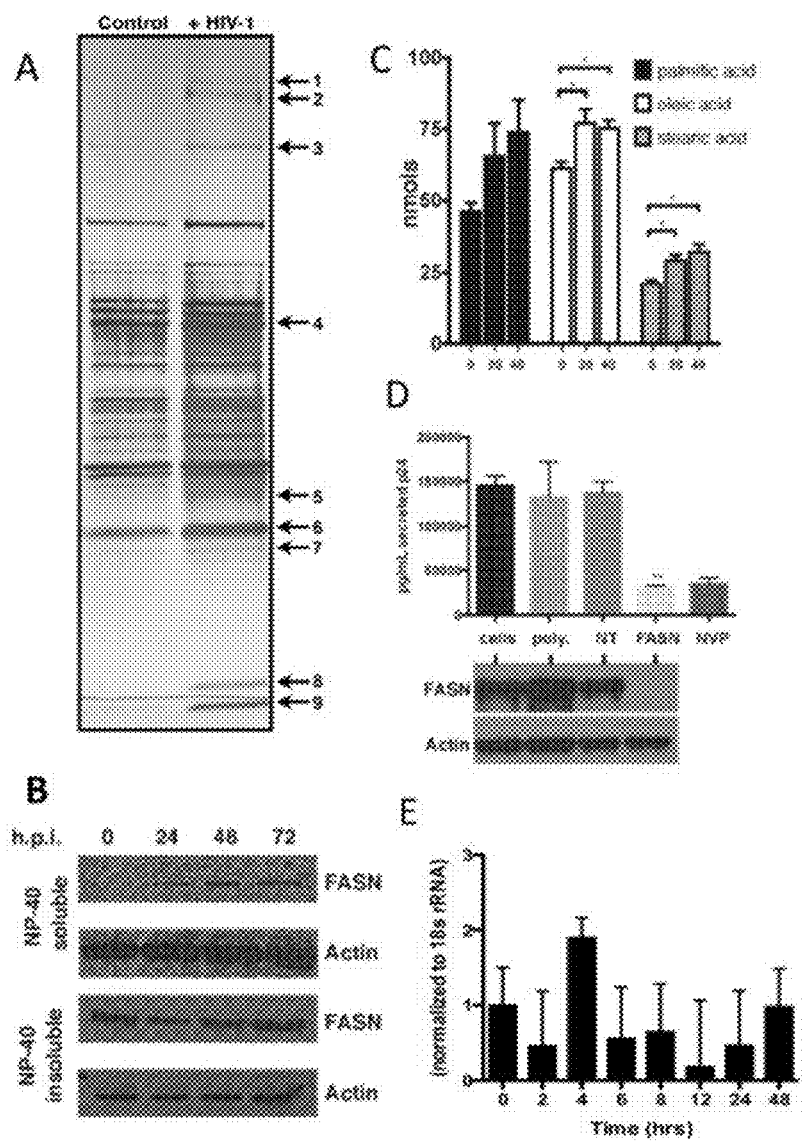
FIG. 21 illustrates that HIV replication regulates FASN and that FASN activity is required for HIV replication. (A) TZM-bl cells were HIV-infected and the TZM-bl purinome was captured 48-hours post-infection. Proteins that remained bound to the resin after a high ionic wash were competed off the resin with 25 mM ATP. Proteins were resolved by one-dimensional SDS-PAGE, visualized with silver stain, and identified with MALDI-TOF sequencing as the following: I. Ubiquitin carboxyl terminal hydrolase (Q9Y4E8), 2. ATP-dependent RNA helicase DHX8 (Q14562), 3. Fatty acid synthase (P49327), 4. HSP90-beta (P08238), 5. GDP-L-fucose synthetase (Q13630), 6. L-lactate dehydrogenase (P07195) and pyridoxal kinase (O00764), 7. Argininosuccinate synthase (P00966), 8. Nucleoside diphosphate kinase-A (P15531) and, 9. Nucleoside diphosphate kinase-B (P22392). (B) Western blot analysis of FASN protein shows HIV-induced protein redistribution to a NP40-soluble fractions (h.p.i.=hours post infection). (C) HIV-induced fatty acid production in TZM-bl cells, (D) siRNA-based knockdown of FASN significantly reduces HIV p24 secretion (compared to a non-targeting control). * Indicates p<0.05, ** indicates p<0.0001 (student's t-test). Poly=polymer control, NT=non-targeting siRNA (control), NVP=40 nM nevirapine. (E) FASN mRNA levels, normalized to 18S rRNA levels, following infection with HIV-1NL43 for the indicated number of hours. Normalized mRNA levels at 4 h post infection are not significantly different than normalized mRNA levels at time 0, p=0.2, student's t-test. Data are representative of two independent experiments.

The disclosed protein affinity media, using the purine-binding pocket to capture the entire purinome enabling it to be screened against chemical libraries en masse (Graves et al, 2002), was utilized to define purine-binding proteins regulated by HIV-1 infection. HeLa-derived TZM-bl cells were HIV-infected, and 48 hours later lysed, and incubated with the purinome-affinity media. After competing bound proteins off the resin with ATP, it was noted that HIV-infection increased the recovery of several human proteins to the purinome-binding resin, including fatty acid synthase (FASN), heat-shock protein 90 (HSP90), and others (FIG. 21A). Although all of the proteins identified are potential therapeutic targets, owing to its specialized, well-defined cellular function (de novo fatty acid synthesis) and limited cellular expression, FASN was focused on. Other targets such as ATP-dependent RNA helicase and nucleoside diphosphate kinase have either broader or less well defined functions in cells, and therefore may be more of a challenge in terms of future drug development. Heat shock protein 90 (Hsp90) is a validated cancer target with a role in HIV replication. To validate the mass spectrometry data, FASN expression was assayed in TZM-bl cells 24, 28, or 72 hours post HIV infection. Western blotting with FASN-specific antibodies confirmed that HIV increased FASN levels in the detergent soluble fraction of cellular lysates as soon as 12 hours post infection (FIG. 21B). To determine if HIV-infection regulates FASN activity, intracellular fatty acid (FA) levels were quantified in TZM-bl cells with or without HIV infection. Forty-eight hours post infection, HIV, in a dose dependent manner, increased intracellular palmitic, oleic, and stearic acid levels (FIG. 21C). These in vitro results complement a previous report that demonstrated HIV-positive patients have elevated serum FASN levels compared to HIV-negative individuals; specifically, a study of 191 people living with HIV-1 showed that people living with HIV-1 not taking antiretroviral therapy (ART) had elevated serum FASN levels compared to both HIV-negative people and people living with HIV-1 on ART (Aragones et al., 2010). Thus, this result is consistent with previous in vitro and in vivo studies that correlated HIV-1 infection with increased FASN levels.

In TZM-bl cells. FASN mRNA levels, normalized to 18S rRNA, did not change following HIV-1 infection, suggesting FASN regulation in TZM-bl cells occurs post-transcriptionally (FIG. 21E). Western blotting with a FASN-specific antibody confirmed that HIV-1 infection increases FASN levels as early as 24 h post infection (FIG. 21B).

Figure 25:
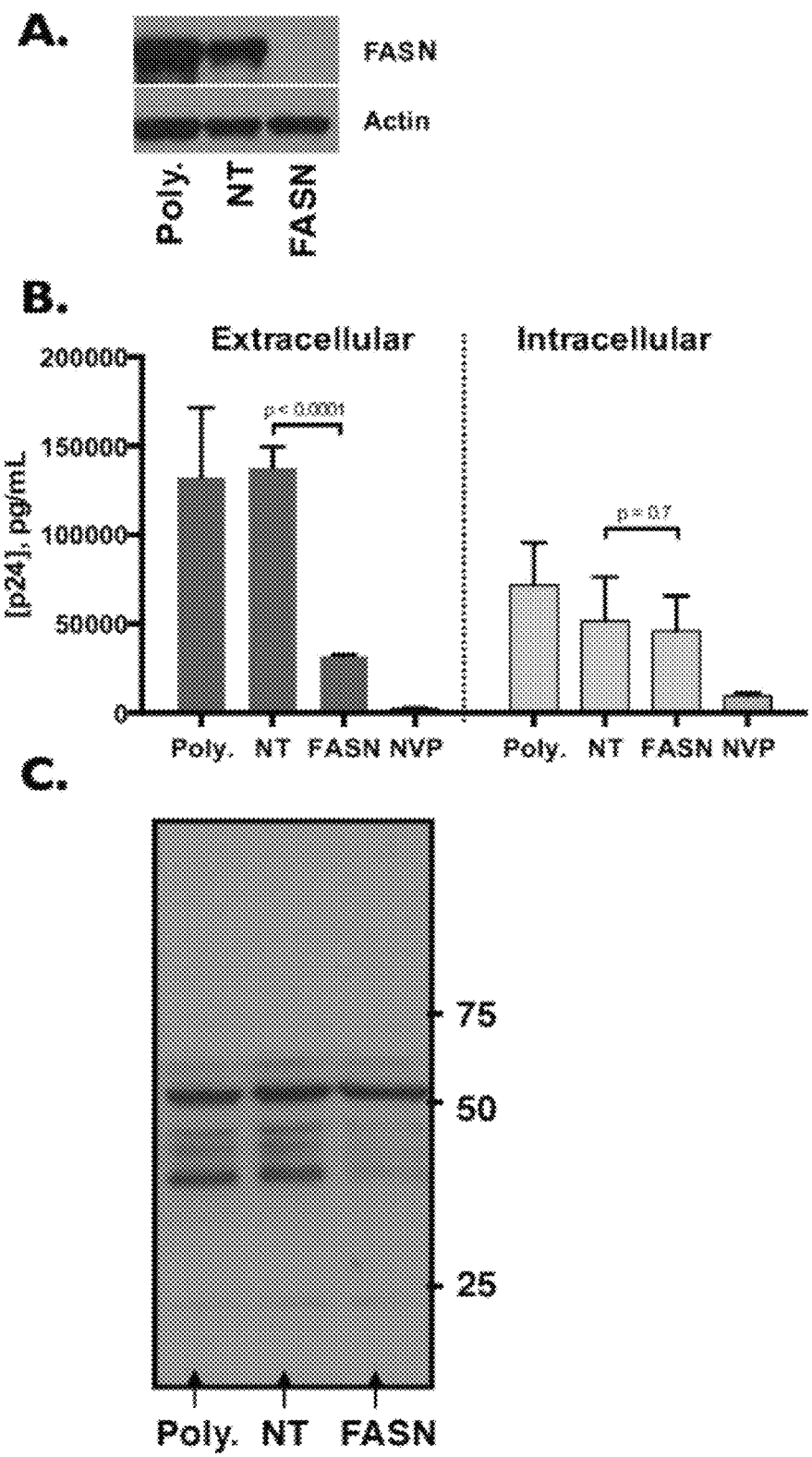
FIG. 25 demonstrates that FASN knockdown reduces HIV-1 particle production without affecting intracellular Gag production. (A) FASN immunoblot confirms reduction in endogenous FASN levels in TZM-bl cells. (B) Extracellular (left) and intracellular (right) p24 levels following siRNA-mediated FASN knockdown in TZM-bl cells infected with HIV-1 for 48 h. Bars represent mean p24±SD, quantified using a commercial ELISA, n=3, p-values generated with student's t-test. (C) anti-Gag western blot of lysates from HIV-infected cells with or without FASN knockdown. Molecular weight markers (kD) indicated in right margin. Poly=polymer (transfection) control, NT=nontargeting siRNA (siRNA control), FASN=FASN-targeted siRNAs, NVP=0.4 µM nevirapine.

To determine if productive HIV replication requires FASN activity. TZM-bl cells were treated with FASN-specific siRNA, which compared to control (non-targeted, NT) siRNA, reduced HIV p24 production by 77% (FIG. 21D). Despite this decrease in culture supernatant p24 levels, siRNA-mediated FASN knockdown did not significantly reduce intracellular p24 levels, measured by ELISA (FIG. 25B), suggesting that HIV-1 replication uses FASN activity during a late step in HIV-1 replication (e.g. protein trafficking, virion assembly, or virion release from the cell). Anti-Gag western blot of HIV-infected, FASN-knockdown cells indicates similar levels of intracellular p55 and p24 (FIG. 25C).

Figure 27:
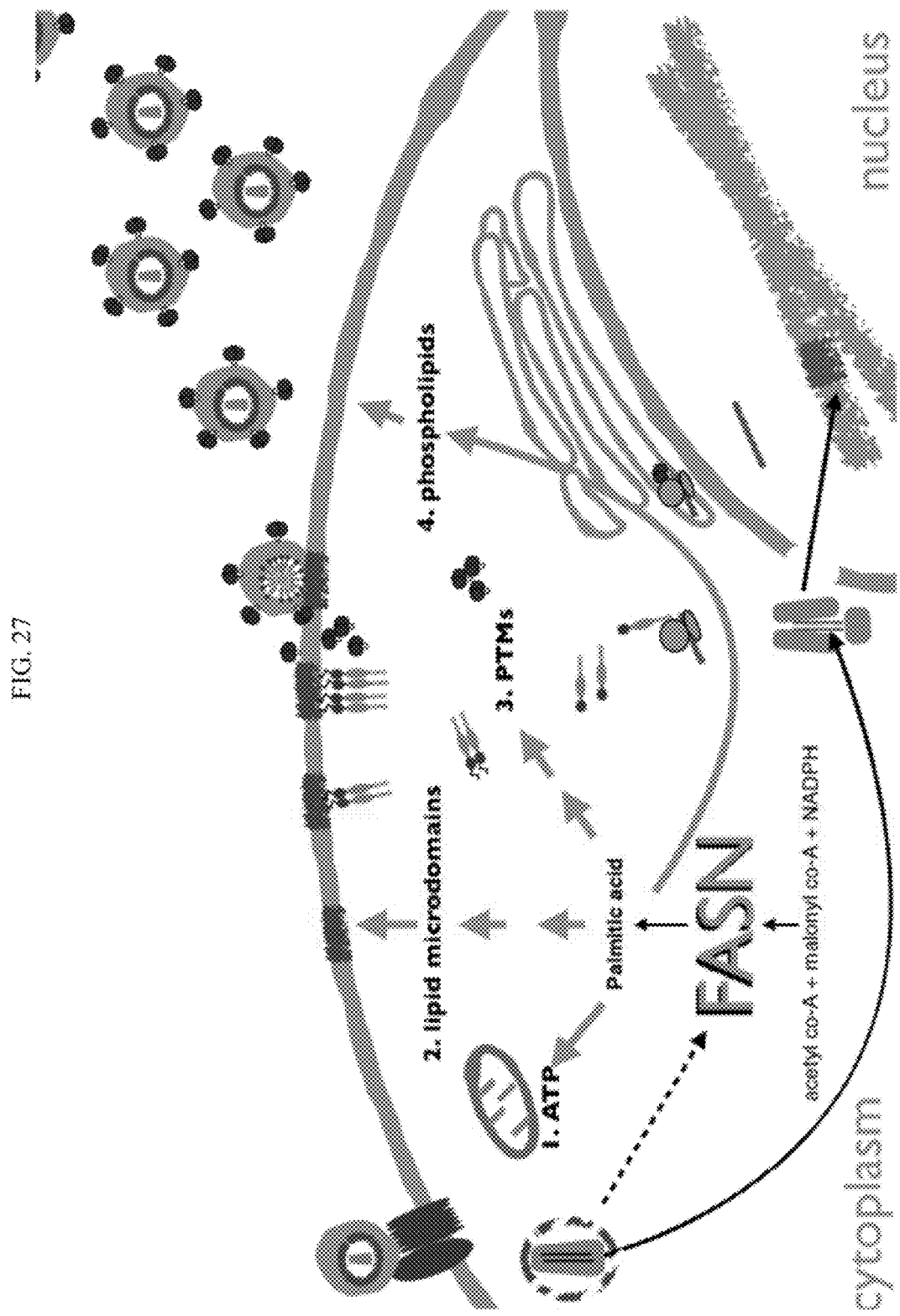
FIG. 27 is a graphical illustration of the potential mechanisms linking FASN activity to HIV-1 replication. 1) provision of fatty acids used for ATP production and energy homeostasis, 2) creation of lipid micro domains (rafts) favoring HIV-1 budding, 3) generation of fatty-acyl adducts (e.g. palmitate or myristate) for post-translational modification (PTM) of Env, Gag, Nef, or host proteins, 4) homeostatic replenishment of membrane lipids lost during viral budding.

The molecular mechanism by which increased FA biosynthesis promotes HIV replication is currently unknown, but plausible mechanisms include the following (FIG. 27): 1) provision of FA's used for ATP production and energy homeostasis, 2) replenishment of lipid bilayers lost during viral budding (Lorizate et al., 2013) or creation of lipid micro domains that favor viral budding (Ono et al., 2001), 3) generation of fatty-acyl adducts (e.g. palmitate or myristate) for post-translational modification (PTM) of Env, Gag, Nef, (Resh, 1999) or host proteins required for HIV-1 replication, 4) replenishment of phospholipids to regenerate the lipid bilayer lost during viral budding, increased mitochondrial capacity through activation of P oxidation (Smith, 1994), or any combination of these activities.

Figure 23:
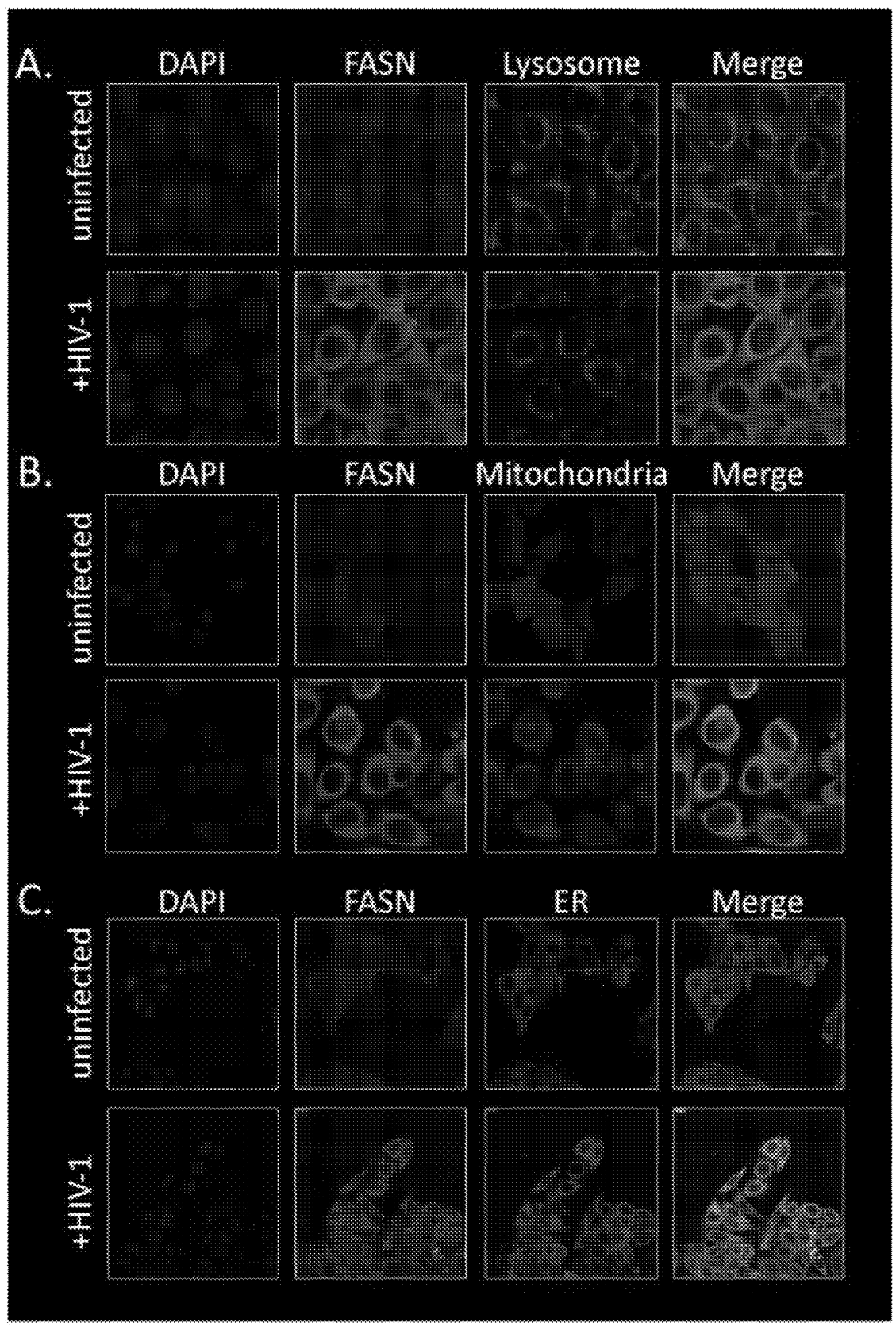

It has been shown that viral infections can change subcellular localization of FASN; for example, Dengue (Heaton et al., 2010) infection causes FASN to relocalize to a perinuclear space. Vaccinia virus infection has been shown to cause FASN to relocalize to mitochondria, likely for energy homeostasis (i.e., FIG. 27, mechanism 1; Greseth et al., 2014). FASN previously reported association with flavivirus replication (Heaton et al, 2010; Huang et al., 2013; Martin-Acebes et al., 2011). Flaviviruses such as HCV and Dengue virus likely use FASN/FA to rearrange intracellular membranes to replicate their genomes on membranous webs (Heaton et al., 2010; Huang et al., 2013). To determine if HIV-1 infection also causes FASN relocalization, an immunofluorescence assay was used to monitor FASN distribution in HIV-1 infected TZM-bl cells. Although the intensity of FASN staining increased following HIV-1 infection, redistribution of FASN to a perinuclear space, lysosomes (FIG. 23A), mitochondria (FIG. 23B), or the endoplasmic reticulum (FIG. 23C) was not observed. Thus, similar to HCV (Yang et al., 2008), HIV-1 infection does not cause intracellular FASN redistribution.

When FASN activity is inhibited in the context of HIV-1 infection, HIV-1 Gag is produced but viral particles are not released into the culture supernatant. Based on this observation, we expect hypothesized mechanisms 2 and 3 (above) offer the most plausible mechanism by which HIV-1 leverages FASN activity: to generate FA to create cholesterol-rich lipid micro domains that promote viral budding (Ono et al., 2001), or to generate fatty-acyl adducts required for viral protein function (Bryant et al., 1990; Li et al., 2007; Lindwasser et al., 2002; Pal et al., 1988). Despite the requirement of FASN for nascent virion production, FASN activity is not required for intracellular Gag protein production, indicating that FASN-dependent de novo fatty acid biosynthesis contributes to a late step of HIV-1 replication.

Figure 19:
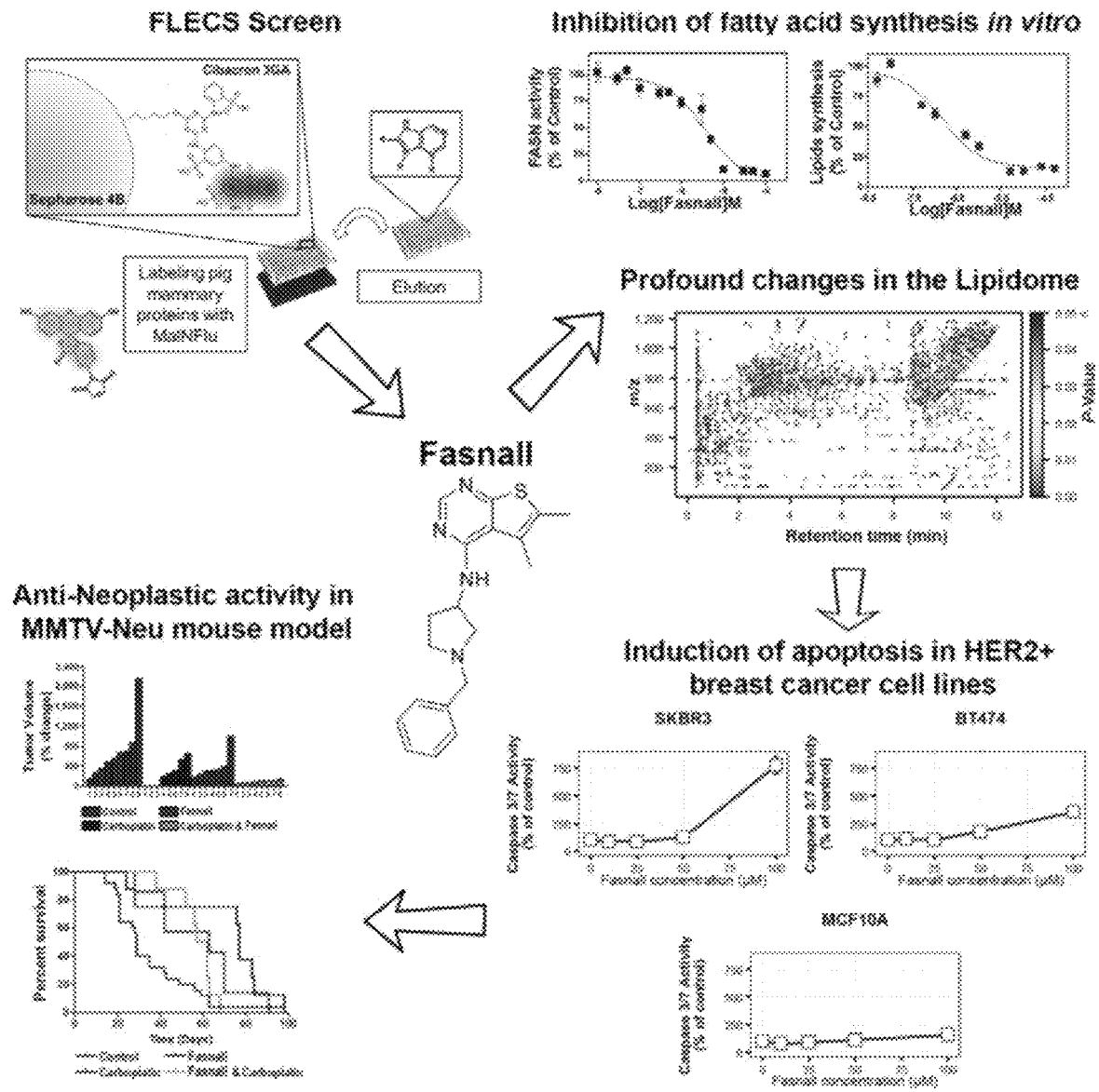
FIG. 19 is a graphical summary of the screening process, identification of HS-106 and in vitro and in vivo profiling activities.
Figure 20:
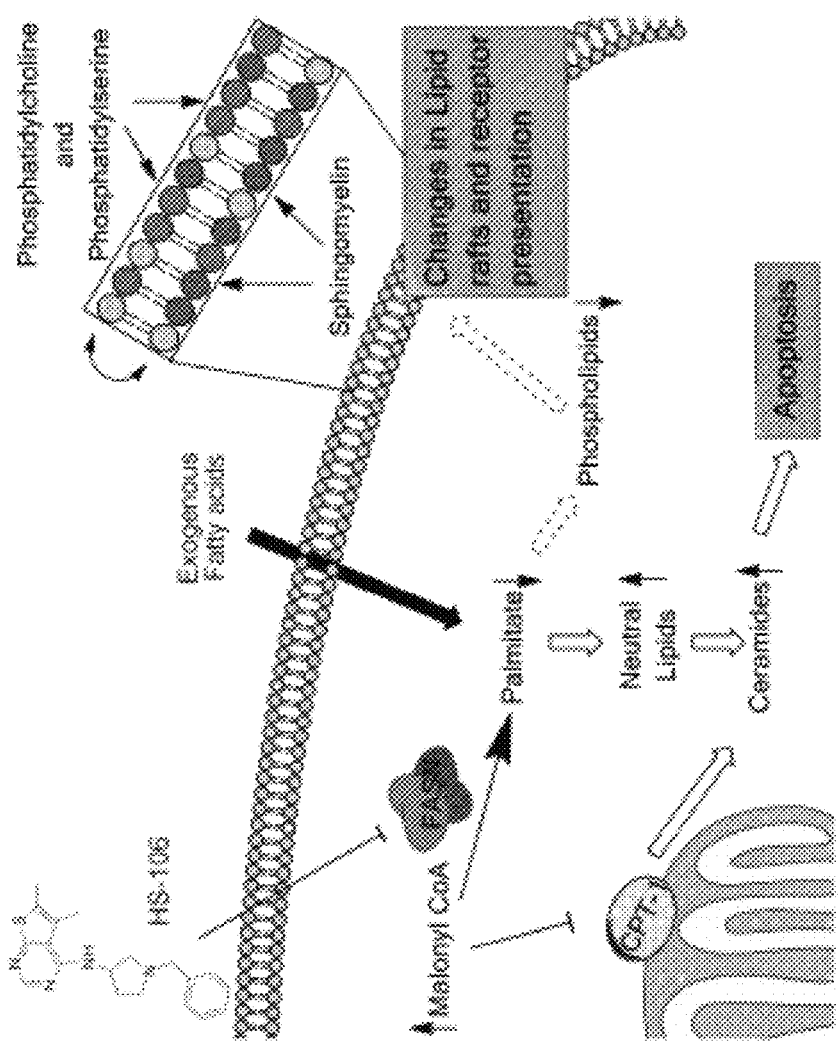
FIG. 20 is a cartoon illustration graphically depicting the activity of HS-106 in the FASN cascade.

Dependency of HIV replication on FASN activity is consistent with other studies of enveloped viruses, including hepatitis C (HCV), Dengue (DENY), Epstein-Barr, and West Nile virus, which also require host FASN activity (Huang et al., 2013; Heaton et al., 2010; Li et al., 2004; Wilsky et al., 2012; Martin-Acebes et al., 2011). The finding that HIV both regulates and requires FASN activity suggested efforts to identify a small molecule inhibitor targeting the FASN purine-binding pocket. Purinome mining to define the Hsp90 inhibitor SNX5422 has been previously reported (Fadden et al., 2010). SNX5422 targets the HSP90 purine-binding pocket. To simplify the identification of novel FASN inhibitors, a variation of proteome mining technology, called fluorescence linked enzymatic chemoproteomic strategy (FLECS) was employed. A 3,379-member small molecule library comprising compounds with structural similarity to any purine or known purine analog scaffold (Hughes et al, 2012) was assembled. Cibacron Blue Sepharose was used to capture native FASN from lactating pig mammary gland extract, then labeled bound proteins with thiol-reactive fluorescein, and screened for molecules that competitively release fluor-labeled proteins (Carlson et al, 2013) (FIG. 19). Cibacron blue resin has been used by others to enrich NAD and NADP binding proteins from tissues extracts and FASN is highly induced in lactating tissues (Miyaguchi et al., 2011; Muratsubaki et al., 1994). The screen identified several molecules that eluted FASN with varying degrees of selectivity and potency (FIGS. 1 and 3). Active molecules were subsequently categorized by their ability to block FASN activity in a HepG2-based FASN assay. HIS-106 (FIG. 9) was further evaluated due to its potent cellular blockade of both acetate and glucose incorporation into total lipids, with $EC_{50}$ values of 147 nM (95% C.I. 92-236 nM) and 213 nM (95% C.I. 144-316 nM), respectively (FIG. 2A,B,D) without affecting the cell viability (FIG. 22C). Because several pathways are represented in the glucose and acetate assays, purified FASN was used to confirm that HS-106 potently inhibits native, human FASN ($IC_{50}$=46 nM, 95% C.I. 30-70 nM, FIG. 2E). HS-106 was also discriminated from other screening hits based on its selectivity profile within the compound library. FIG. 3 shows the results of repeated FLECS screens of the library across multiple enzyme classes within the purinome, including several protein kinases, heat shock proteins and metabolic enzymes (Carlson et al., 2013). These data suggest that the HS-106 scaffold has unique specificity towards FASN.

HS-106 Anti-HIV Activity In Vitro and In Vivo

Figure 24:
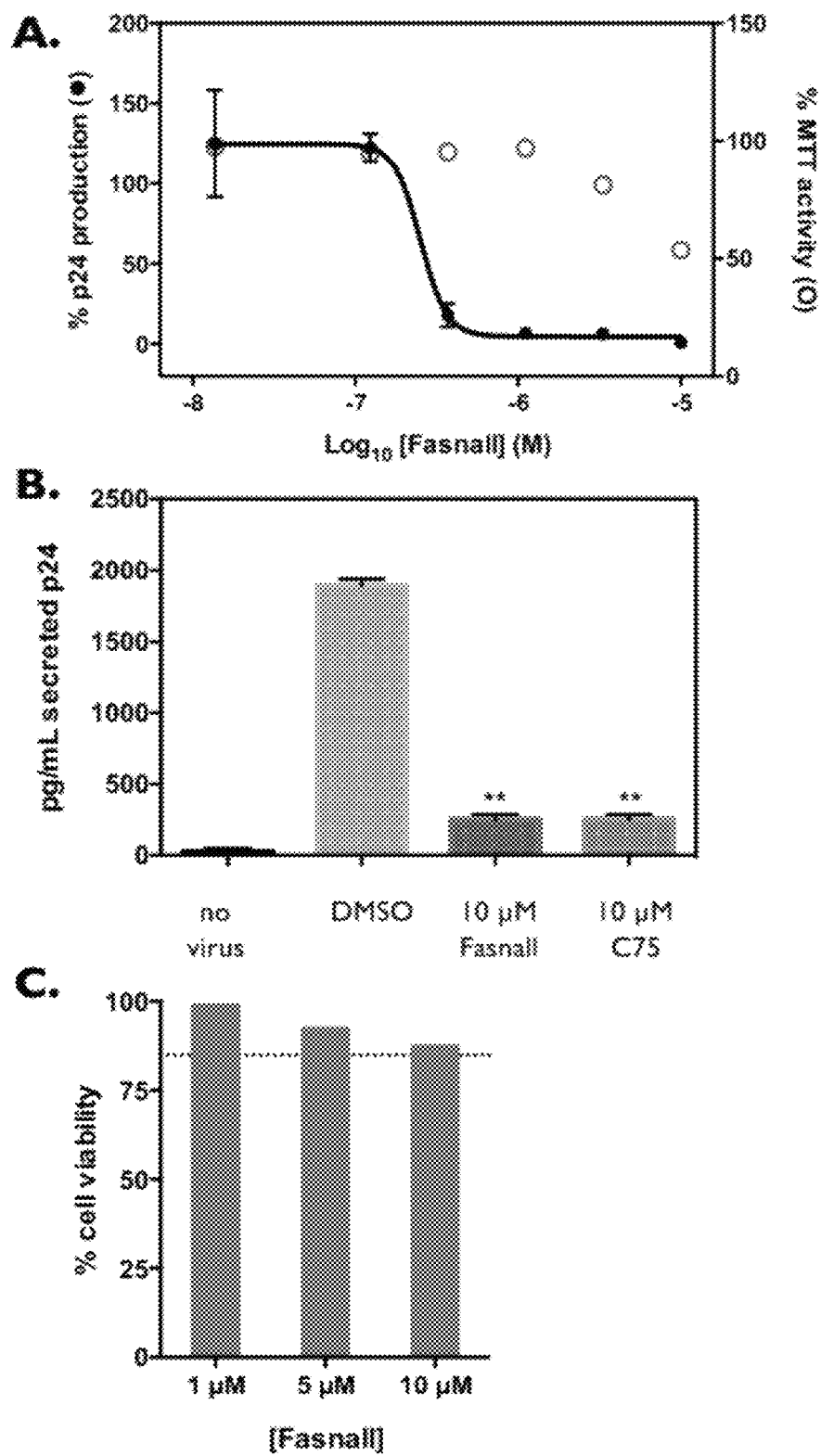
FIG. 24 illustrates Fasnall inhibition of HIV-1 replication. (A) Extracellular p24 levels in TZM-bl cells 48 h post infection (black dots±SD, n=3, black line), without significant effects on TZM-bl cell viability (i.e. mean MTTactivity; open circles, n=3) (B) Fasnall and C75 significantly reduce HIV-1 replication in primary PBMC, as measured by p24 production. The data presented are mean values (±SD) from three independent experiments. ** Indicates p<0.0001, treatment versus DMSO-treated control (Students t-test). (C) PBMC viability after treatment with Fasnall as measured by propidium iodide staining (dotted line drawn at 85%).

Because HS-106 is a potent FASN inhibitor, and the results disclosed indicate that HIV replication requires FASN activity, HS-106 was evaluated for anti-HIV activity. TZM-bl cells were infected with HIV-1 and 48 hours post infection, extracellular p24 levels were measured as a surrogate measure of HIV-1 replication. In this model, Fasnall potently inhibited HIV-1 p24 production with an $EC_{50}$ of 213 nM (95% C.I. 93-487 nM; FIG. 24A) and an estimated cellular toxicity ($TC_{50}$) of 10 µM (FIG. 24C), resulting in an antiviral index ($TC_{50}/EC_{50}$) of 47. To determine if Fasnall blocked HIV-1 in activated T-cells, p24 production from HIV-1 infected primary PBMCs was measured in the presence or absence of 10 µM Fasnall. In this physiological relevant model of HIV-1 replication, HS-106 reduced HIV-1 p24 production approximately 10-fold (FIG. 24B), demonstrating dose-dependent anti-HIV activity (reduced by 87% at 10 µM and 96% at 50 µM), with negligible effects on cell viability (FIG. 24C). Moreover, when PBMCs were treated with C75, a commercially available FASN inhibitor, similar reductions in extracellular p24 levels were observed (FIG. 24B).

Figure 26:
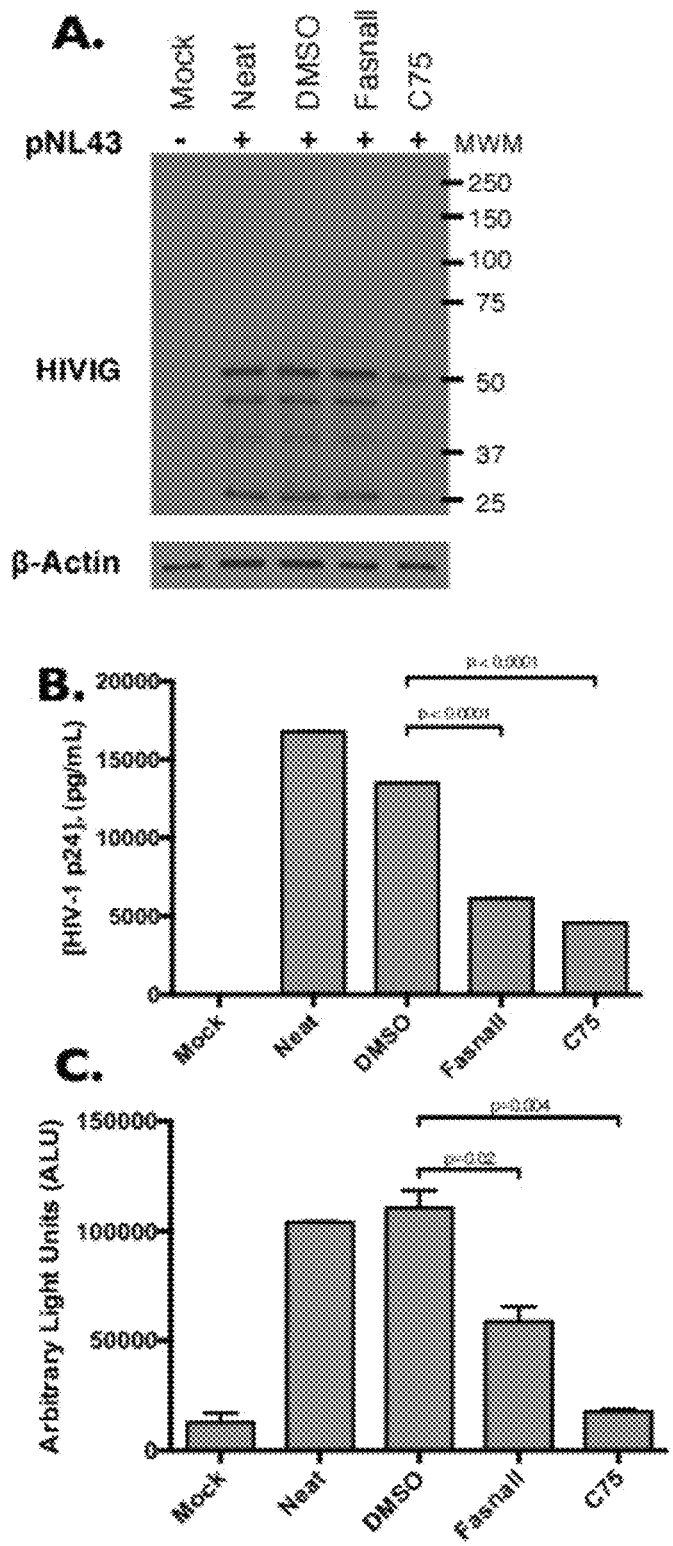
FIG. 26 demonstrates that FASN inhibition disrupts a late step in the HIV-1 replication cycle. (A) TZM-bl cells were transfected with pNL4-3 provirus plasmid for 48 h in the presence or absence of 10 µM Fasnall or C75 or DMSO (0.01%). Intracellular expression of HIV-1 proteins was monitored by HIVIG-western blot, and β-actin was used as loading control. (B) Supernatant associated virion production was monitored using a p24 ELISA. (C) 48 hours post-transfection, cell culture supernatants were removed and incubated with fresh TZM-bl (indicator) cells for an additional 48 hrs. Values expressed as the mean±standard deviation, and are representative of three independent experiments. p-values were generated with student's t-test. Molecular weight markers (kD) indicated in right margin.

To test further the hypothesis that HIV-1 replication requires FASN activity during the late stages of viral replication, TZM-bl or SupT1 (data not shown) cells were transfected with a HIV-1 provirus (pNL43) in the presence or absence of Fasnall or C75. Similar to siRNA-based FASN knockdown, Fasnall-based inhibition of FASN did not reduce intracellular Gag levels (FIGS. 25 and 26) but did significantly reduce HIV-1 p24 particle deposition into culture medium, as measured by p24 production (FIG. 26B). Fasnall and C75 similarly reduced the number of infectious HIV-1 particles (FIG. 26C). Thus, FASN inhibition reduces nascent HIV-1 virion production without reducing HIV-1 protein synthesis.

Figure 22:
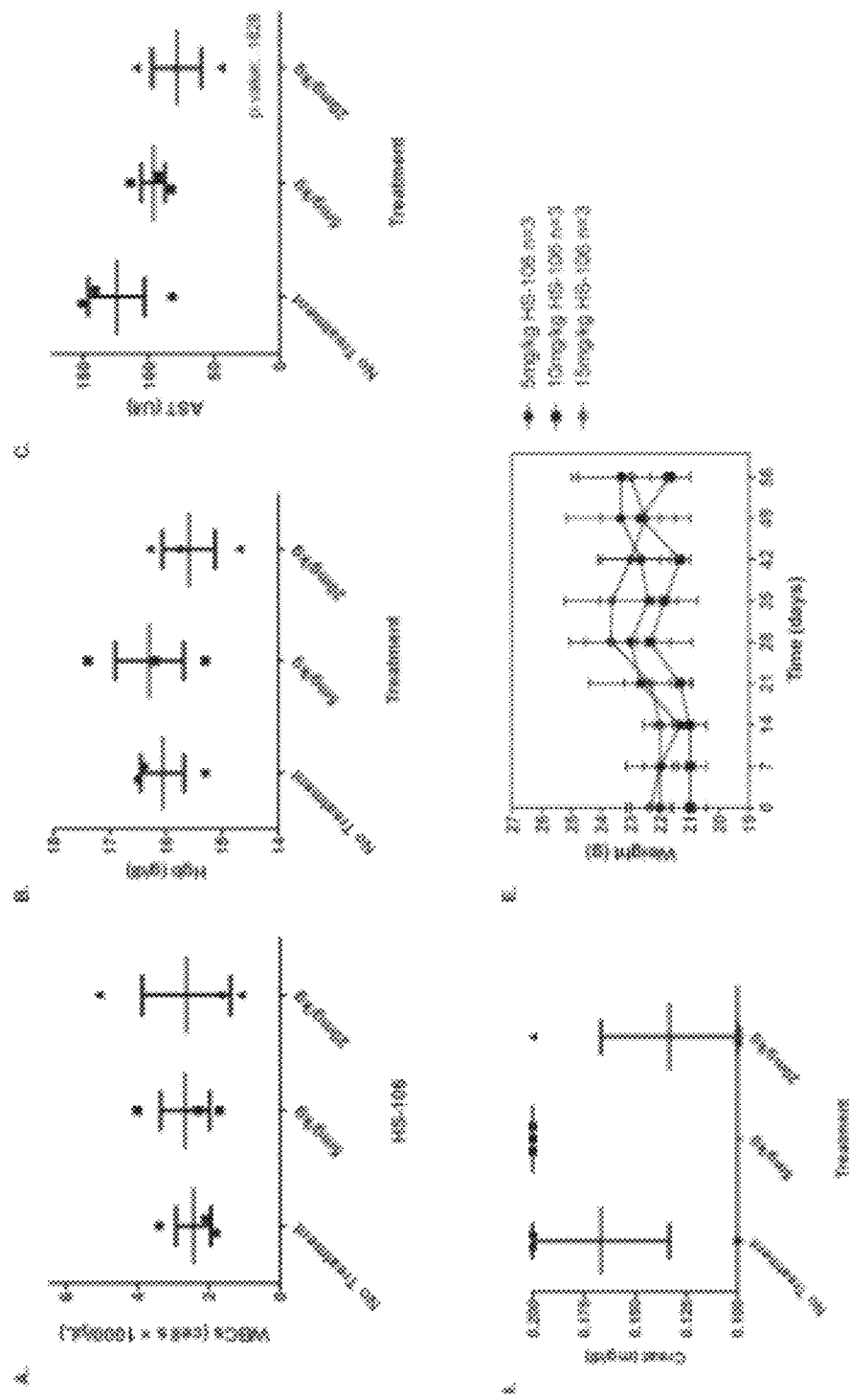
FIG. 22 illustrates the effect of HS-106 treatment on healthy mice. HS-106 treatment delivered IP at indicated doses on day 0 and 3. Blood drawn on day 4 indicates no change in (A) white blood cell counts. (B) hemoglobin levels, (C) aspartate aminotransferase (AST) levels, or (D) creatine levels. (E) Female FVB/J mice treated with HS-106 twice weekly did not show any signs of weight loss over a period of 60 days. During the daily assessment, the mice also did not show any symptoms of toxicity or stress such as guarded posture and labored breathing FIG. 23 demonstrates that incubation of TZM-bl cells with HIV-1 increases intensity of FASN staining but does not change FASN subcellular localization. In all panels, FASN is labeled green and the nucleus is colored blue (DAPI). Red color denotes (A) lysosome (CD63), (B) mitochondria (Mitotracker), (C) endoplasmic reticulum (calreticulin). Data are representative of two independent experiments.

To test if HS-106 is toxic to mice, two animal studies were initiated. In an acute toxicity study, mice received 80, 20, or 5 mg/kg HS-106 IP on day 1 and 3, and blood was collected on day 4. HS-106 was acutely toxic at 80 mg/kg but at 5 and 20 mg/kg, HS-106 did not affect white blood cell count, hemoglobin levels, kidney, or liver function (FIG. 22). In a chronic exposure study, mice received biweekly IP injections of 5, 10, or 15 mg/kg HS-106 and none of the doses showed signs of toxicity or stress (FIG. 22). Thus, HS-106 is a chemically tractable molecule, with potent ex vivo anti-HIV activity, which is well tolerated in mice.

Accordingly, in one aspect, the invention relates to a method of inhibiting Fatty Acid Synthase (FASN) with a FASN inhibitor that binds to the FASN purine-binding cofactor domain, the method comprising contacting cells that express FASN with an inhibitor that binds to the FASN purine-binding cofactor domain.

In one embodiment, the inhibitor does not bind to the substrate domain.

In one embodiment, the inhibitor inhibits both acetate and glucose incorporation into total lipids. In one embodiment, the inhibitor inhibits both acetate and glucose incorporation into lipids in the HepG2 cell line with an IC50 value below about 300 nM.

In one embodiment, the inhibitor possesses a thiophenopyrimidine scaffold. In one embodiment, the inhibitor possesses a thieno[2,3-d]pyrimidine scaffold. In one embodiment, the compound is (N-(1-benzylpyrrolidin-3-yl)-5,6-dimethylthieno[2,3-d]pyrimidin-4-amine, or a pharmaceutically acceptable salt thereof.

In another aspect, the invention relates to a method of promoting apoptosis in a cancer cell dependent on FASN activity, the method comprising contacting the cells with an inhibitor that binds to the FASN purine-binding cofactor domain.

In one embodiment, the inhibitor does not bind to the substrate domain. In one embodiment, the inhibitor possesses a thiophenopyrimidine scaffold. In one embodiment, the inhibitor possesses a thieno[2,3-d]pyrimidine scaffold. In one embodiment, the compound is (N-(1-benzylpyrrolidin-3-yl)-5,6-dimethylthieno[2,3-d]pyrimidin-4-amine, or a pharmaceutically acceptable salt thereof.

In another aspect, the invention relates to a method of treating cancer in a subject, the method comprising administering to the subject in need thereof, a therapeutically effective amount of a FASN inhibitor that binds to the FASN purine-binding cofactor domain.

In one embodiment, the inhibitor does not bind to the substrate domain.

In one embodiment, the cancer is selected from the group consisting of HER2-positive breast cancer, triple negative breast cancer, melanoma, hepatocellular carcinoma, and leukemia.

In one embodiment, the inhibitor possesses a thiophenopyrimidine scaffold. In one embodiment, the inhibitor possesses a thieno[2,3-d]pyrimidine scaffold. In one embodiment, the compound is (N-(1-benzylpyrrolidin-3-yl)-5,6-dimethylthieno[2,3-d]pyrimidin-4-amine, or a pharmaceutically acceptable salt thereof.

In one embodiment, the inhibitor is co-administered with a platinum-based antineoplastic compound. In one embodiment, the inhibitor is co-administered with carboplatin or cisplatin. In one embodiment, the inhibitor is co-administered with carboplatin. In one embodiment, the dosage of platinum-based antineoplastic compound is less than that required when administered in the absence of a FASN inhibitor.

In another aspect, the invention relates to a method of inhibiting viral replication in cells dependent on FASN expression, the method comprising contacting the cells with an inhibitor that binds to the FASN purine-binding cofactor domain.

In one embodiment, the inhibitor does not bind to the substrate domain.

In one embodiment, the inhibitor inhibits HIV viral replication in a TZM-bl model of HIV replication with an EC50 value below about 500 nM. In one embodiment, inhibition of FASN reduces HIV-1 particle production without affecting intracellular Gag production. In one embodiment, the inhibitor attenuates HIV replication during a late stage of its replication cycle. In one embodiment, nascent HIV-1 virion production is inhibited without reducing HIV-1 protein synthesis.

In one embodiment, the inhibitor possesses a thiophenopyrimidine scaffold. In one embodiment, the inhibitor possesses a thieno[2,3-d]pyrimidine scaffold. In one embodiment, the compound is (N-(1-benzylpyrrolidin-3-yl)-5,6-dimethylthieno[2,3-d]pyrimidin-4-amine, or a pharmaceutically acceptable salt thereof.

In another aspect, the invention relates to a method of treating a viral infection in a subject, the method comprising administering to the subject in need thereof, a therapeutically effective amount of a FASN inhibitor that binds to the FASN purine-binding cofactor domain.

In one embodiment, the viral load is reduced. In one embodiment, the viral infection is infection by an enveloped virus. In one embodiment, the viral infection is infection by a virus selected from the group consisting of human immunodeficiency virus, cytomegalovirus, Dengue, hepatitis B, hepatitis C, Epstein-Barr, influenza virus, respiratory syncytial virus and West Nile virus. In one embodiment, the virus is human immunodeficiency virus. In one embodiment, lipid dysregulation-based morbidities are reduced. In one embodiment, the inhibitor possesses a thiophenopyrimidine scaffold.

In one embodiment, the inhibitor possesses a thieno[2,3-d]pyrimidine scaffold. In one embodiment, the compound is (N-(1-benzylpyrrolidin-3-yl)-5,6-dimethylthieno[2,3-d]pyrimidin-4-amine, or a pharmaceutically acceptable salt thereof. In one embodiment, treating a viral infection further comprises co-administration of an additional anti-retroviral compound.

In another aspect, the invention relates to a pharmaceutical composition comprising (N-(1-benzylpyrrolidin-3-yl)-5,6-dimethylthieno[2,3-d]pyrimidin-4-amine, or a pharmaceutically acceptable salt thereof, and a pharmaceutically acceptable carrier.

In another aspect, the invention relates to the compound (R)—(N-(1-benzylpyrrolidin-3-yl)-5,6-dimethylthieno[2,3-d]pyrimidin-4-amine or a pharmaceutically acceptable salt thereof.

In another aspect, the invention relates to the compound (S)—(N-(1-benzylpyrrolidin-3-yl)-5,6-dimethylthieno[2,3-d]pyrimidin-4-amine or a pharmaceutically acceptable salt thereof.

EXAMPLES

The following examples are provided as illustration and not by way of limitation.

Materials and Methods

ATP, NAD, NADPH, acetyl CoA, malonyl CoA, Propidium iodide, Hoechst 33258, Rnase A, Cibacron blue sepharose and Resazurin were obtained from Sigma-Aldrich (St Louis, Mo., USA). [$^3$H] Acetate, 3-[3H] D-Glucose, 2-[$^{14}$C] malonyl CoA, and MicroScint-E were bought from PerkinElmer (Waltham, Mass., USA). Fluorescein-5-maleimide was bought from Invitrogen (Carlsbad, Calif., USA). Humulin R insulin was bought from Lilly (Indianapolis, Ind., USA). Sephacryl S-300 HR was bought from GE health care (Little Chalfont, Buckinghamshire, UK). Cells were obtained from ATCC (Manassas, Va., USA). Cell culture media were bought from Gibco life technologies (Carlsbad, Calif. USA). TZM-bl cells were obtained from the NIH AIDS Research and Reference Reagent Program maintained in DMEM supplemented with 10% fetal bovine serum (FBS).

FLECS Screen

Porcine mammary glands were collected from lactating pigs as previously described (Hughes et al., 2012). Tissues were homogenized in lysis buffer A (100 mM sodium fluoride, 5 mM EDTA, 1 mM DTT and 5% glycerol made in 10 mM sodium phosphate buffer pH 7.5) in a ratio of 3 ml of buffer per each gram of tissue. After removing cell debris by centrifuge at 142,000×g for 45 minutes and filtering through glass wool, the homogenate was applied to Cibacron blue sepharose pre-equilibrated with buffer B (100 mM sodium fluoride, 5 mM EDTA, 1 mM DTT and 50 mM sodium citrate made in 10 mM sodium phosphate buffer pH 7.5) in a ratio of 4.5 g of tissue to each ml of settled resin. To remove dehydrogenases and reduce the amount of ATP binding proteins bounded to resin, the resin was washed with 10 bed volumes of buffer B then with one bed volume of 5 mM NAD made in buffer B followed by one bed volume of buffer B. After that, the resin was washed with one bed volume of 10 mM ATP. To label the FASN attached to the resin, to each ml of resin, 1 ml of 10 mM sodium phosphate buffer (pH 7.5) containing 50 g of fluorescein-5-maleimide (pre-dissolved in DMF) was added to the resin and incubated overnight at 4° C. with slow rotation. The resin was then washed with 20 bed volumes of buffer B to remove any excess fluorescein. The resin was suspended in buffer B (1:1, v/v) and distributed in 96 well filter plates (50 μl/well). Fluorescein labeled proteins were eluted from the resin by an in-house library of 3,379 purine-based compounds. For each well, 50 μl of each compound was added (1 mM made in buffer B with 10% DMSO). Different concentrations of ATP were used as a control. The eluents were collected in 96 well black plates by centrifugation at 1,260×g for 5 minutes. Fluorescence in each well was measured at Ex/Em: 485/535 nm. Eluents with the highest fluorescent intensity were run on SDS PAGE. After silver staining, proteins in each band were identified by (MALDI-TOF/TOF) MS as described previously (Carlson et al., 2013).

[$^3$H] Glucose and Acetate Incorporation in HepG2 Cells

Incorporation of radiolabeled glucose or acetate in total lipids was measured according to published methods (Haystead and Hardie, 1986). HepG2 cells (80% confluent in 12 wells plates) were starved overnight in MEM Alpha, the medium was then changed with DMEM medium containing 0.1 g/L glucose 10% FBS and 51 μM insulin and 1 μCi 3-[$^3$H] D-glucose or 1 μCi [$^3$H]-acetate in addition to different concentrations of each compound. After incubation for 1 hour at 37° C., 5% $CO_2$, the cells were washed with ice cold PBS and detached by treating with 100 μl trypsin for 10 min then 1 ml of ice cold PBS was added. The cells suspension was then sonicated for 3 times in 30 seconds intervals and kept on ice. From each well 1 ml of cell lysate was added to a 4 ml scintillation vial and 2 ml of MicroScint-E was added. The vials were mixed thoroughly then centrifuged for 30 min at 3000 rpm and the $^3$H radioactivity was measured by liquid scintillation counting.

FASN Activity Assay

Human FASN activity was measured by monitoring the incorporation of 2-[$^{14}$C] malonyl CoA into fatty acids using liquid scintillation counting by a method similar to the one described by Richardson et al (Richardson and Smith, 2007). FASN (10 μg/ml of PBS containing 1 mM DTT and 1 mM EDTA) was pre-incubated with different concentrations of HS-106 (final DMSO concentration 1%) at 37° C. for 30 minutes, then substrates were added (20 μM acetyl CoA and 200 μM NADPH) in a total reaction volume of 100 μl. The reaction was initiated by adding 10 μl of 50 μM malonyl CoA spiked with 0.05 μCi of 2-[$^{14}$C] malonyl CoA. After incubation for 30 minutes at 37° C., lipids were extracted 3 times with 150 μl (2:1, v/v) chloroform:methanol. Then, to the pooled organic phases, 1 ml of toluene containing 25 g/L Butyl-PBD was added and radioactivity was measured by liquid scintillation counting.

Proliferation Assay

MCF10A (5,000 cells/well), MCF7 (7,500 cells/well), MDA-MB-468 (5,000 cells/well), BT474 (7,500 cells/well), and SKBR3 (5,000 cells/well) were seeded in 96 well plates with 10% FBS 4 g/L glucose DMEM media except for MCF10A which was DMEM/F12 media. After 24 hours, cells were treated with different concentration of HS-106 or C75. Every 24 hours for five days, media from one of the plates was removed and plate was frozen at −80° C. After collecting all the time points, to each well 100 μl $ddH_2O$ was add and the plates were frozen again. Then 100 μl of Hoechst 33258 solution made in TNE buffer (1 μl from Hoechst stock (1 mg/ml in 1:4 DMSO:H2O) in 1 ml of TNE (which contains 10 mM Tris, 2M NaCl and 1 mM $Na_2$EDTA) and fluorescence was measured at Ex/Em: 355/460.

Cell Cycle Analysis

After treating BT474 cells with different concentrations of HS-106 for 24 hours, cells were collected and fixed with 70% ethanol, washed with PBS then treated with 20 mg/ml Rnase A. Then cells were stained with 50 μg/ml Propidium iodide and DNA content for each cell was quantified using a BD Accuri C6 flow cytometer (BD), and data were analyzed using the CFlow Plus software (BD).

Western Blot Analysis

Cell lysate from cell treated for 24 hour with 10 μM of HS-106 or DMSO were loaded (28 μg/well) and run on Criterion XT Tris-HCl Gel (4-15% gradient) (Bio-Rad) according to manufacture instructions, then the proteins were transferred to PVDF membrane overnight using 25 volt at 4° C. After that, membranes were blocked and blotted for FASN (Cell signaling antibody number 3180) and GAPDH (Cell signaling antibody number 5174).

Caspase 3/7 Activity Assay

The assay was performed using a similar protocol to the one described by Fritz et al (Fritz et al., 2001). Cells were seeded at a density of 10,000 cells/well and treated with different concentrations of HS-106 or C75. After 24 hours, to each well, 50 μl of Caspase assay/lysis buffer (50 mM HEPES pH 7.5, 100 mM KCl, 5 mM EDTA, 10 mM $MgCl_2$, 10 mM CHAPS, 20% Sucrose, 10 mM DTT, 10 μM of (Z-DEVD)2-Rh110 (Santa Cruz Biotech) and complete protease inhibitor (Roche)) was added. After 6 hours of incubation at 37° C., fluorescence was measured at Ex/Em: 485/535 nm.

Lipidomics Sample Preparation

BT474 cell pellets (5 vehicle and 5 treated with 10 μM HS-106 for 2 hours) were separately thawed on ice, and 100 μL of ammonium bicarbonate, pH 8, was added to each. Pellets were then probe sonicated at power level 3 for 3 bursts of 5 seconds each burst, cooling on ice between bursts. Bradford assay was performed on each solubilized pellet using 10× diluted material. 1 mg from each was taken out and normalized to 137 µl total with AmBic in a 96-well plate. To each sample well, 200 µL of methanol was added followed by the addition of 600 µL of MTBE. The plate was capped and mixed at 800 rpm at room temperature for 1 hour. Plate was then centrifuged at 2000 rpm at room temperature for 10 min and 400 µL of the MTBE/MeOH layer was pipetted out and transferred to another plate. Then the extract was dried under nitrogen gas and samples were reconstituted in 100 µL of 2:1:1 IPA:ACN:H2O. A pool was made by taking an equal volume from all 10 samples.

Mass Spectrometry Lipid Profiling

Each sample was analyzed twice using Ultra Performance Liquid Chromatography/Electrospray Ionization/Tandem Mass Spectrometry (UPLC/ESI/MS/MS) in positive ion mode (3 µL) and negative ion mode (10 µL). UPLC separation was performed using a binary gradient separation on a Acquity UPLC (Waters Corporation, Milford, Mass.) using a Acquity 2.1 mm×10 mm 1.7 µm CSH C18 column. Mobile phase A contained 60/40/0.1 v/v/v MeCN/water/formic acid with 10 mM ammonium formate, and mobile phase B contained 90/10/0.1 v/v/v isopropanol/MeCN/formic acid. Lipid separation was performed at 0.6 mL/min and 60° C. column temperature, using a complex gradient program as follows: initial conditions 40% B, ramp to 43% B at 1.3 minutes, ramp to 50% B at 1.4 minutes, ramp to 54% B at 8 minutes, ramp to 70% B at 8.2 minutes, ramp to 99% B at 12.2 minutes, ramp to initial condition 40% B at 12.3 minutes, then hold at 40% B for re-equilibration until 14 minutes. Via electrospray ionization, the LC eluent was introduced into a G2 Synapt (Waters and data was collected between 50-1200 m/z in 0.3 seconds; MS/MS was collected at a scan rate of 0.2 sec for peaks above a threshold of 3000 intensity/sec for positive ion and 1000 intensity/sec for negative ion. Source parameters are as follows for positive/ negative ion respectively: capillary at 2.7 kV/2.3 kV, cone voltage of 30 V, 500 C desolvation temperature, 700 L/hr desolvation gas, 150 L/hr cone gas, and a source temperature of 100° C. Lockmass calibration was performed every thirty seconds using a solution of 500 fmol/µL Leucine-Enkephalin in positive (556.2771 m/z) or negative mode (554.2615). Quantitative data were analyzed in Progenesis QI (Nonlinear Dynamics, Ltd/Waters Corporation). Quantitative data including accurate mass, charge state, retention time and intensity were exported for additional statistical analysis (https://discovery.genome.duke.edu/express/resources/3745/3745_IDandStats_HvsD_Progenesis QI_062514.xlsx). Putative identifications were made by searching against compiled LipidMaps databases with theoretical fragmentation where available, using 10 ppm precursor ion tolerance. Putative identifications were confirmed based on accurate mass and retention time using standards for fatty acids myristic acid, palmitic acid, palmitoleic acid, stearic acid, oleic acid, and linoleic acid using endogenous standards purchased from TCI America, Sigma Aldrich, and Ultra Scientific.

Purinome Capture

ATP sepharose was synthesized as described (Haystead et al., 1993). TZM-bl cells were obtained from the NIH AIDS Reagent Program (submitted by Dr. John C. Kappes, Dr. Xiaoyun Wu and Tranzyme Inc.). HIV-1 pseudovirions consisting of pNLCH5.1 backbone and pJRFL envelope were produced in 293T cells according to standard protocols (Russell et al., 2011). 48 hours post infection, TZM-bl cells were lysed at 4° C. in lysis buffer (20 mM hepes pH 7.4, 1× complete protease inhibitors without EDTA (Roche), 120 mM NaCl, 20 mM MgCl$_2$, 1 mM DTT, 0.1% NP-40), centrifuges at 16,000×g for 10 minutes at 4° C., and the supernatant was loaded onto 100 µL ATP sepharose. ATP-sepharose was incubated with cell lysate for 1 hr. at 4° C., washed 3× with low salt buffer (50 mM hepes pH 7.4, 120 mM Nacl, 20 mM MgCl$_2$, 1 mM DTT), then washed 2× with high salt buffer (low salt buffer with 300 mM NaCl [final]), then washed 2× with low salt buffer. Proteins were competed off the resin with 25 mM ATP dissolved in low salt buffer. Eluents were dialyzed to remove ATP, mixed with Laemli Sample buffer, and visualized by 1-D SDS PAGE. Gels were fixed and silver stained according to published protocols (Graves et al., 2002). Individual proteins were excised from the gel manually and cut into 1 mm×1 mm pieces, washed alternately with 25 mM ammonium bicarbonate (×3), and acetonitrile (×3), then fully dehydrated in acetonitrile. Acetonitrile was removed, 30 µL of porcine trypsin (20 µg/mL, Promega) was added on ice, then incubated for 15 minutes. The gel pieces were then incubated at 37° C. for 12-16 hours, then the supernatant was transferred to a second tube, and acetonitrile was added to the gel pieces to complete the extraction of digested peptides. This extract was pooled, frozen and lyophilized. The peptides were resuspended in 5 µL of 1:1 acetonitrile:0.25% Trifluoroacetic acid and immediately spotted on the MALDI target. For MALDI analysis, the matrix solution consisted of alpha-cyano-4-hydroxycinnamic acid (Aldrich Chemical Co. Milwaukee, Wis.) saturating a solution of 1:1:0.02 acetonitrile: 25 mM ammonium citrate in water:trifuoroacetic acid. Approximately 0.15 µL of peptide solution was spotted on the MALDI target immediately followed by 0.15 µL of the matrix solution. This combined solution was allowed to dry at room temperature. MALDI MS and MS/MS data was then acquired using the AB Sciex 5800 TOFTOF Mass Spectrometer (AB Sciex, Framingham, Mass.). Resultant peptide mass fingerprint and peptide sequence data was submitted to the SPROT(UNIPROT) or NCBI database using the Mascot search engine to which relevance is calculated and scores are displayed.

FASN Visualization.

pNL4.3 was obtained through the NIH AIDS Reagent Program from Dr. Malcolm Martin (Adachi et al., 1986). NL4-3 was produced in 293T cells according to standard protocols (Russell et al., 2011) and quantified with a commercial p24 ELISA assay kit (Zeptometix). At various times post-pNL4-3 infection, TZM-bl cells were washed with PBS, and lysed (as above). Cleared supernatants were obtained by centrifugation at 14,000 g for 15 min at 4° C. Protein concentration was estimated with BCA assay and equal amounts of protein were boiled in IX SDS Laemmli buffer for 10 min. Proteins were subjected to 8% SDS-PAGE then transferred to nitrocellulose membranes. Membranes were blocked with 5% (WV) nonfat dry milk in TBST and incubated overnight with anti-FASN (Abcam, ab99258) at 4° C., washed in TBS-T, incubated with HRP-conjugated anti rabbit secondary antibody (Abcam, ab6721) in TBS-T for 1 hr., washed, then visualized with ECL detection reagent (GE Biosciences). Membrane was stripped and probed with anti-actin (Cell signaling, 4970) to verify protein loading. For immunofluorescence experiments, 1×10$^5$ TZM-bl cells were plated on sterilized coverslips, infected with 10 ng/ml NL43 virus for various times. Cells were washed twice with PBS, fixed with 4% paraformaldehyde for 30 min at 4° C., washed thrice with PBS, permeabilized with chilled methanol for 15 min at 4° C., washed thrice with PBS, blocked with PBS+1% BSA for 1 h, then incubated with anti-FASN primary antibody (Abcam: ab99358, 1:200) diluted in PBS+

1% BSA for 1 hr at RT. Cells were rinsed three times with PBS, incubated with Alexa fluor 488-anti rabbit IgG (Abcam 1:400), followed by three additional washes with PBS. Coverslips were mounted on slides using prolong gold DAPI mounting medium and observed on FLUOVIEW Olympus microscope using immersion oil.

SiRNA Knockdown of FASN

ON-TARGET plus SMART pool siRNA targeted against human FASN (FASN) (L-003954-00-0005) and ON-TARGET plus non-targeting (NT) control siRNA (D-001810-01-05) was purchased from Dharmacon. TZM-bl cells were transfected either with 200 nM FAS-targeting siRNA or 200 nM NT siRNA using Trans-IT transfection regent (Mirus Bio LLC) according to the manufacturer's protocol. After 48 hours, cells were infected with 10 ng/ml p24 NL4.3 and incubated for an additional 24 hours. Media was replenished with fresh media after 24 hours and incubated with fresh media for additional 24 hours. Supernatants were collected for HIV p24 ELISA and cells were washed with PBS and saved for Western blotting.

Primary Cell Infection

Primary cell experiments were approved by the Ohio State University Institutional Review Board, protocol #2014H0001. Peripheral blood mononuclear cells (PBMC) were isolated from healthy donor by Ficoll-Paque centrifugation, stimulated in complete RPMI 1640 medium (Gibco, Carlsbad, Calif.) containing 10% FBS, 100 µg/mL penicillin/streptomycin and supplemented with 5 µg/mL phytohemaglutinin (PHA; Gibco) for 48 h. and maintained thereafter in complete RPMI medium supplemented with 20 U/mL of interleukin-2 (Gibco). PBMCs were seeded in 24-well plate ($2 \times 10^5$ cells/well) and triplicate wells were treated with 10 or 50 µM C75, HS-106, or with DMSO and subsequently infected with 10 ng/mL p24 equivalents of HIV-1$_{LucR-T2A}$ virus, which is derived from NL4-3 (Edmonds et al., 2010). Cells were washed 24 h post infection. Supernatants were collected 4 days post infection and p24 content analyzed by quantitative ELISA (Zeptometrix).

Fatty Acid Analysis and Quantification

An equivalent number of TZM-bl cells were infected with NL4-3 virus at 0, 20, or 40 ng (p24)/mL. Cells were collected at 48 h and 72 h post infection. Total fatty acids were extracted using a modified version of the Bligh and Dyer protocol (Bligh and Dyer, 1959). This consisted of sequential extractions with (2:1) Chloroform:methanol, (1:1) chloroform:methanol, (1:2) chloroform:methanol, and (10:10:3) chloroform:methanol:water. Fatty acid methyl esters were generated by methanolysis with 3N methanolic HCl (85° C. overnight) followed by trimethylsilylation with Tri-Sil reagent (Thermo scientific). Heptadecanoic acid (17:0) was used as an internal standard. Samples were dissolved in hexane prior to injection on a Thermo scientific Trace GC ULTRA with a Rtx-SMS column (30 m×0.25 mm internal diameter, 0.25 µm film thickness, Restek Corporation, Bellefonte, Pa.), following of mass spectrometer, DSQII. Instrument settings included an internal temperature of 150° C. for 3 min, increasing to 200° C. at 2° C./min and to 250° C. at 40° C./min holding for 4 min.

HepG2 Cell Viability

HepG2 cells were seeded in 96 well plates and after reaching 80% confluency, the cells were treated with different concentrations of HS-106 for 4 hours. At the end of the treatment time, 10 µl of 700 µM Resazurin (prepared with PBS) were added to each well. After 3 hours, the Resorufin fluorescence was measured at Ex/Em: 540/590 nm.

Purification of Human FASN

Confluent BT474 cells grown in high glucose DMEM with 10% FBS, were scraped and washed two times with ice cold PBS. Then, the cells (2.26 g) were homogenized in potter homogenizer for 5 mins in 40 ml of buffer A. The homogenate was centrifuged at 35000 rpm for 45 min then filtered through glass wool resulting in a volume of 27 ml. To the 27 ml of homogenate, 6.37 ml of saturated ammonium sulfate (final saturation 20%) was added and mixed slowly for 20 min then incubated for 1 hour on ice. After spinning the lysate at 15000 rpm for 20 min, the pellet was discarded and to the supernatant (26 ml) 70 ml saturated ammonium sulfate was added (final saturation 35%). After repeating the same procedure in the previous step, the supernatant was discarded and the pellet was collected and dissolved in 20 ml of buffer A and added to 150K MWCO Pierce Protein Concentrators from Thermo Fisher Scientific (Waltham, Mass., USA) then centrifuged for 30 min at 3000 rpm. The resulting volume on the filter (1.5 ml) was added to a Sephacryl S-300 HR column (1×100 cm) pre-equilibrated with PBS. The column was eluted with PBS containing 1 mM DTT at a flow rate of 0.2 ml/min. 2 ml fractions were collected and peaks fractions were run on SDS-PAGE and the ones with FASN band (identified by (MALDI-TOF-TOF) mass spectrometry) were pooled and concentrated using Pierce Protein Concentrators.

FASN Activity Assay

Human FASN activity was measured by monitoring the incorporation of 2-[$^{14}$C] Malonyl CoA into fatty acids using liquid scintillation counting by a method similar to the one described by Richardson et al (Richardson et al., 2008). The enzyme (10 µg/ml of PBS containing 1 mM DTT and 1 mM EDTA) was incubated with different concentrations of HS-106 (final DMSO concentration 1%) at 37° C. for 30 min. After that, substrates was added (20 µM Acetyl CoA and 200 µM NADPH total reaction volume was 100 µl) the reaction was started by adding 100 of 70 µM Malonyl CoA spiked with 0.03 µ$C_i$ of 2-[$^{14}$C] Malonyl CoA. After incubation for 30 min at 37° C., lipids were extracted 3 times with 150 µl 2:1 Chloroform:Methanol using Folch method (Bligh and Dyer, 1959). Then, to the pooled organic phase, 1 ml of Toluene containing 2 g/L Butyl PBD was added and radioactivity was measured by scintillation counting.

Determination of HS-106 Efficacy In Vivo

Single-time parous female MMTV-NEU mice (Jackson Labs Strain 002376) were used to test the efficacy of HS106 (30 pmol/Kg, IP, BIW) alone and in combination with Carboplatin (143 pmol/Kg, IP, QW). Mice were monitored for tumor development by palpating them weekly as per UNC Lineberger Mouse Phase 1 Unit protocol. Once tumors were observed, the mice were placed on treatment. The tumor-bearing mice were injected weekly with HS-106 and/or Carboplatin. The solvent for HS-106 consists of 50% dimethyl sulfoxide (DMSO) and 50% saline (0.9% sodium chloride solution). Clinical grade Carboplatin was purchased from the UNC Hospital pharmacy. Tumor volume was measured at the time of injection by caliper and width (short diameter) and length (long diameter) in millimeters (mm) were recorded. The volume was calculated using the formula: length×width 2×0.5. At the time of injection, body composition was assessed and weight measurements (in grams) were recorded and used to determine toxicity. After three weeks, tumor progression was calculated using the formula: (21 day volume−initial volume)/initial volume× 100. This percent change in tumor volume, at 21 days, was used to assess the objective response rate of the therapies. Mice were treated and monitored until euthanized due predetermined humane endpoints per UNC IACUC protocol 13-190. Overall survival was calculated by date of necropsy–initial treatment date. The same protocol was used for the assessment of HS-106 and HS-106 Carboplatin combo in the Triple-negative breast cancer GEMM, C3Tag mouse model.

HIV/TZM-bl Assays

HS-106 or C75 were dissolved in DMSO to achieve 10 mM stock concentration. The stock solution of each drug was serially diluted 3-fold with DMSO and 2 μL of each dilution was added to each well to achieve final concentration range from 10 μM to 4.6 nM fixing final [DMSO] at 1%. $HIV_{NL4.3}$ was added to $3 \times 10^4$ TZM-bl cells at 10 ng/ml p24 equivalents in the presence of 15 μg/mL DEAE dextran. HIV-infected cells were incubated at 37° C. in 5% $CO_2$ for 24 hours, washed with PBS, fresh media was added, and cell were incubated for another 24 hours. Supernatants were collected and stored at −80° C. until P24 ELISA assay. HIV-1 replication was assessed by quantitative p24 ELISA. Nevirapine (positive control) was obtained from the AIDS Reagent Repository and was used at 0.3 mM ($EC_{50}$) and 0.04 mM ($EC_{90}$).

Real Time Polymerase Chain Reaction (RT-PCR).

TZM-bl cells infected with HIV-$1_{NL4-3}$ at 10 ng (p24)/mL were collected at intervals over 48 h of infection and total RNA was isolated using Qiagen RNeasy kit. Synthesis of cDNA was performed using oligo dT primer and Superscript III Reverse Transcriptase (Invitrogen, Carlsbad, Calif.). Real time PCR using SYBR green kit was performed according to manufacturer's instructions (BioRad, Hercules, Calif.). The FASN primers (sense, 5'-CCCACC-TACGTACTGGCCTA-3' (SEQ ID NO.: 1); antisense, 5'-CTTGGCCTTGGGTGTGTACT-3' ((SEQ ID NO.: 2)) were used to synthesize the PCR products. The 18s ribosomal RNA subunit primers (sense, 5'-CAGC-CACCCGAGATTGAGCA-3' ((SEQ ID NO.: 3)); antisense, 5'-TAGTAGCGACGGGCGGTGTG-3' (SEQ ID NO.: 4)) were used as controls to normalize FASN samples. PCR was run for 40 cycles, with 1 cycle consisting of 30 s at 95° C., 30 s at 55° C., and 30 s at 72° C.

PBMC Viability

PBMCs were isolated by Ficoll-Paque centrifugation, stimulated in complete RPMI-1640 medium (Gibco, Carlsbad, Calif.) containing 10% FBS, 100 μg/mL penicillin/streptomycin and supplemented with 5 μg/mL phytohaemagglutinin (PHA; Gibco) for 48 h, and maintained thereafter in complete RPMI-1640 medium supplemented with 20 U/mL of interleukin-2 (Gibco). PBMCs were seeded in 24-well plate ($2 \times 10^5$ cells/well) and triplicate wells were treated with indicated concentrations of C75, HS-106, or with DMSO, and subsequently infected with 10 ng (p24)/mL equivalents of HIV-$1_{NL4-3}$. Cells were washed 24 h post infection, and supernatants were collected and p24 content analyzed by quantitative ELISA (Zeptometrix, Buffalo, N.Y.). Unfixed PBMCs were exposed to drug for 48 hours, and PBMC viability was assessed by flow cytometry using propidium iodine (PI) exclusion (BD Pharmingen) and Annexin V staining (BD Pharmingen). Viable cells are defined as cells that both exclude PI and are Annexin V negative.

Example 1. HS-106 Inhibits Proliferation in Breast Cancer Cell Lines

Figure 4:
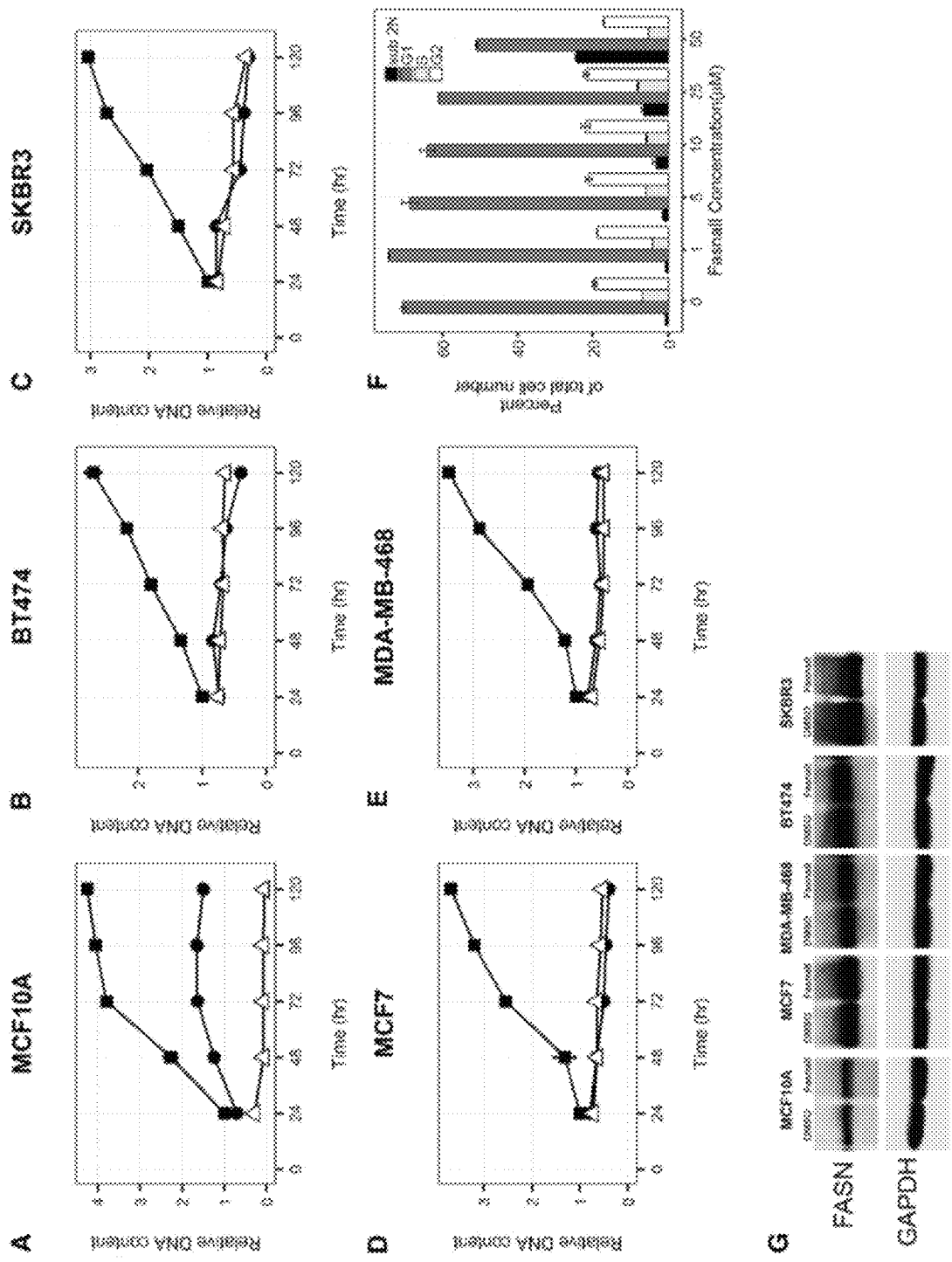
FIG. 4 graphically illustrates the anti-proliferative activity of HS-106 (A-E). Based on the DNA content measured by staining with Hoechst, treating various types of breast cancer cell lines with one dose of 50 nmol/ml of HS-106 (green circle) was able to inhibit cells proliferation with similar potency of 50 nmol/ml C75 (red triangle) except for the non-tumorigenic cell line MCF10A when compared to control (blue squares) (F). Cell cycle analysis for BT474 cells treated with different concentrations of HS-106 for 24 hours shows an increase in the Sub 2N population. (G). Treating breast cancer cell lines with 10 nmol/ml of HS-106 for 24 hours did not have any effect on the expression of FASN.

To evaluate the potential of HS-106 in breast cancer, we first tested its effects on proliferation across a panel of non-tumorigenic (MCF10A) and aggressive tumor forming breast cancer cell lines including ER+ (MCF7), triple negative (MDA-MB-468) and HER2+ (BT474 and SKBR3). HS-106 inhibited the proliferation of aggressive cell lines with similar potency to C75, but showed lower activity in the non-tumorigenic cell line MCF10A (FIG. 4A-E). The weaker effects of HS-106 in MCF10A cells correlated with low expression of FASN in this cell line relative to the more aggressive lines, suggesting the former cells are less dependent on FASN for growth (FIG. 4G). HS-106 treatment of BT474 cells did not induce cell cycle arrest except for an increase in the Sub 2N cell population (FIG. 4F).

Figure 5:
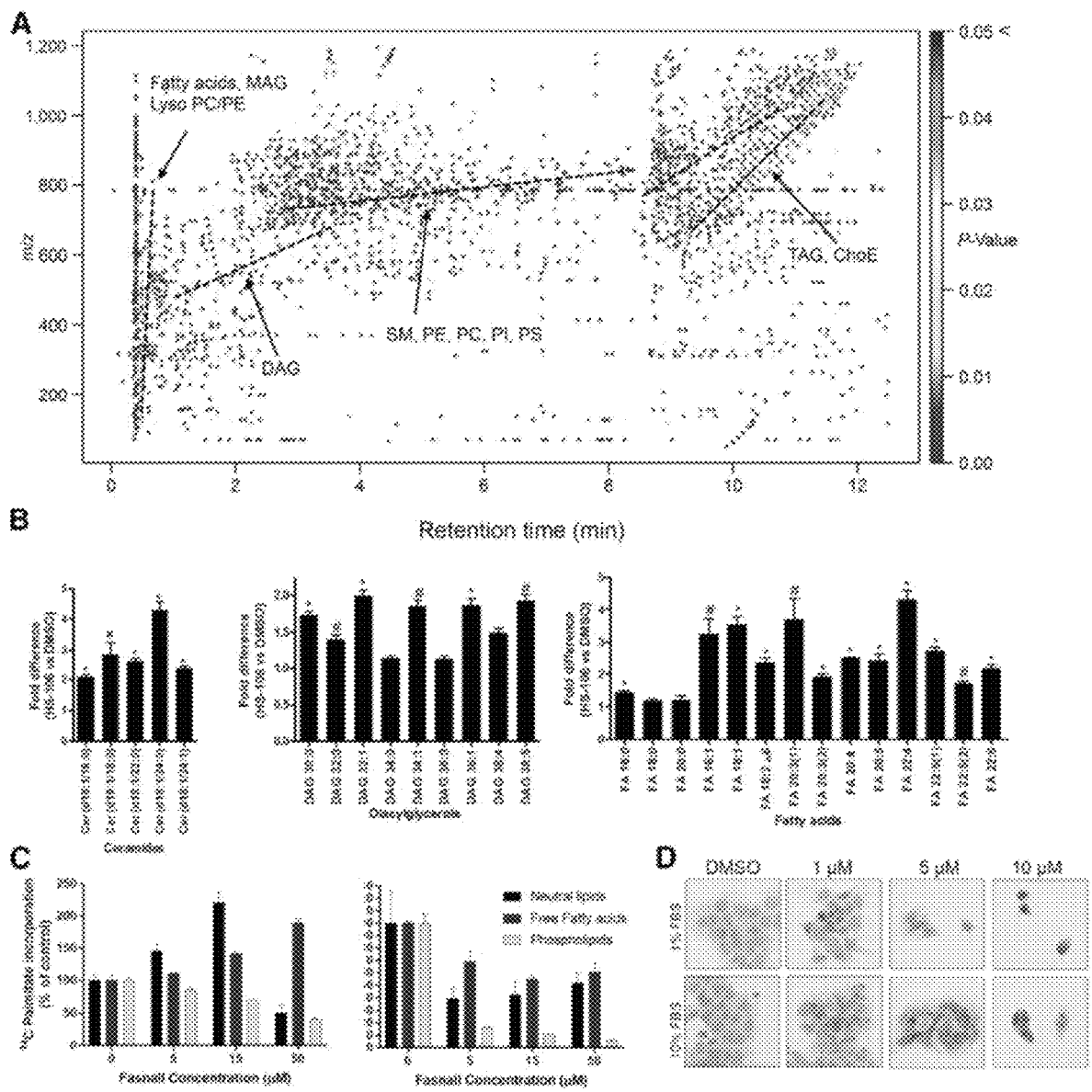
FIG. 5 graphically illustrates the effects of HS-106 on the Lipidome. BT474 cells were treated with 10 nmol/ml of HS-106 for two hours and then lipids were extracted and subjected to LC/MS. More than 3000 lipid features were quantified using both ESI+ and ESI− analyses. (A). Each point represents one of the lipid molecules that were quantified, aggregated for ESI+ and ESI−. The color of each dot represents how significant is the difference in the abundance between the control and treatment (B). The quantified lipids with more than two fold change and p-value <0.01 were examined and identified with endogenous standards or given putative identifications based on retention time, accurate mass, and fragmentation where available (e.g. diacylglycerols, Ceramides, and glycerophospholipids). Of the lipids that were identified, many were diacylglycerols. Ceramides and fatty acids were found to increase over the control (*p<0.01, #p<0.05, n=5) (mean±SEM). (C). BT474 cells were treated with different concentrations of Fasnall for 1 hr and lipids were separated by aminopropyl cartridges after incubating the cells with [3H]acetate for 2 hr. Fasnall was able to inhibit the incorporation of acetate into the different types of lipids, especially the more abundant phospholipids. A similar experiment was done with [14C]palmitate, which showed a dose-dependent increase in palmitate sequestering into free fatty acids and reduction in its incorporation into phospholipids. Similar to free fatty acids, neutral lipids increased except for at 50 mM Fasnall, when they decreased (mean±SEM). (D). Treatment of BT474 cells with different concentrations of Fasnall under 10% FBS conditions induce the formation of lipid droplets as shown by oil red 0 staining, indicating an increase in neutral lipids formation when compared with 1% FBS.
Figure 6:
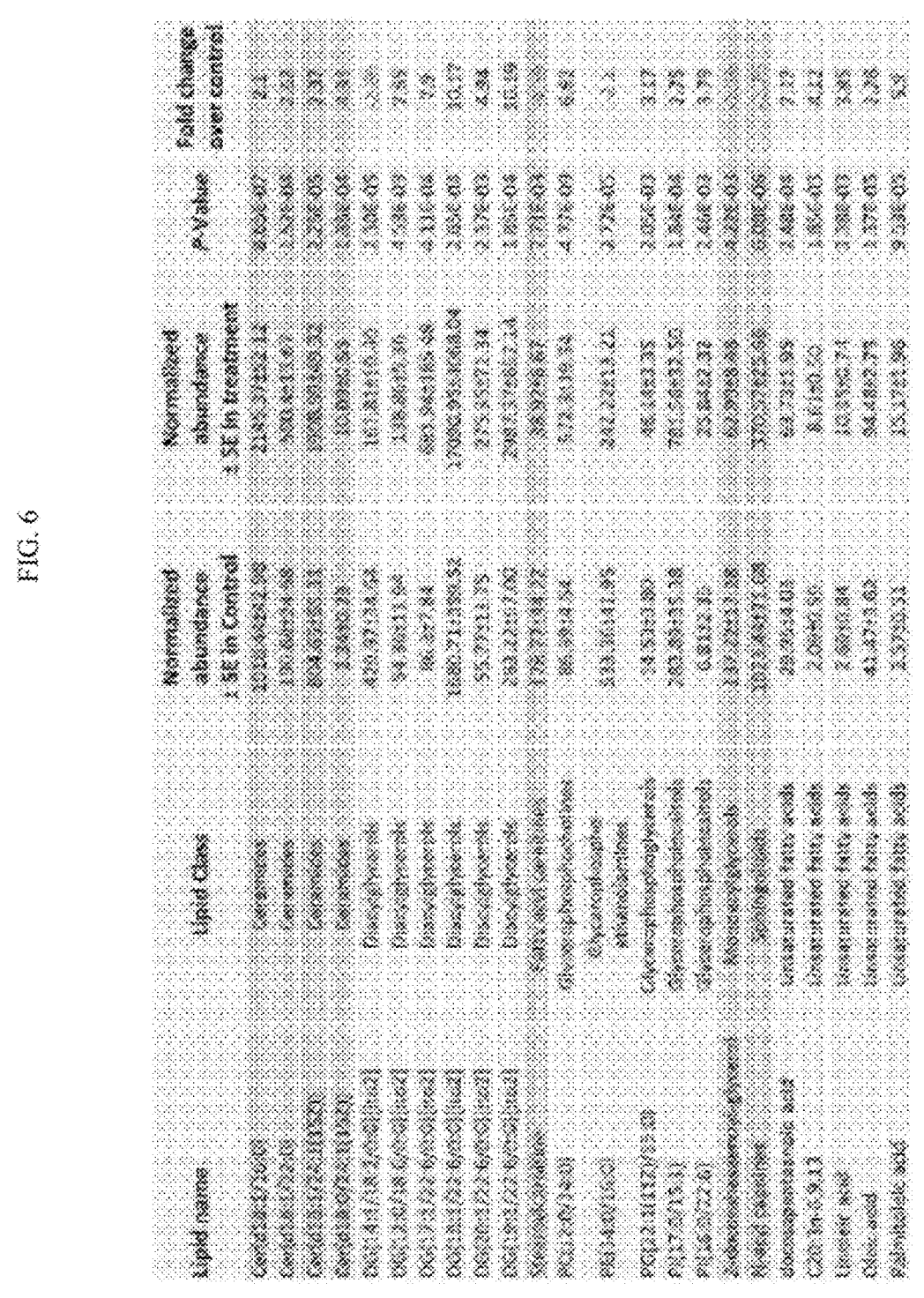
Figure 11:
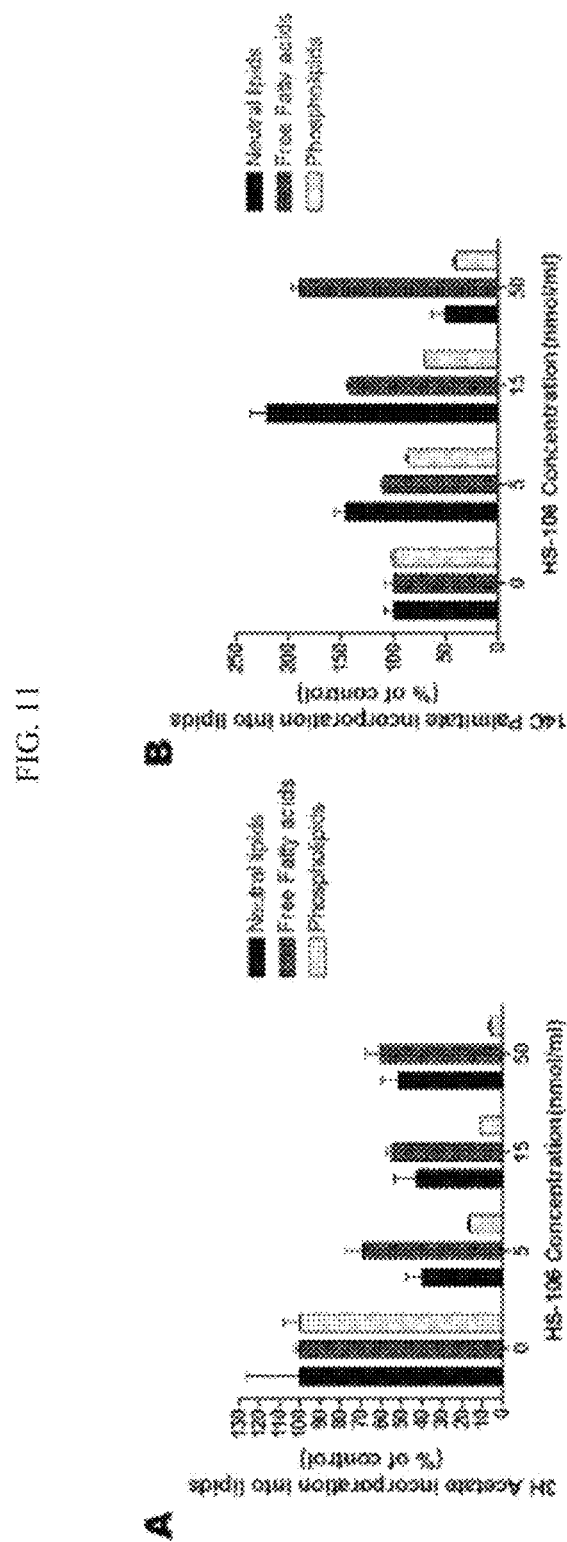
FIG. 11 illustrates the effect of HS-106 on the incorporation of Acetate and Palmitate into the different groups of lipids. (A). BT474 cells were treated with different concentrations of HS-106 for 1 hour then lipids were separated by aminopropyl cartridges after incubating the cells with $^3$H acetate for two hours. HS-106 was able to inhibit the incorporation of acetate into the different types of lipids, especially the more abundant phospholipids. (B). A similar experiment was done with $^{14}C$ palmitate which showed a dose dependent increase in palmitate sequestering into free fatty acids and reduction in its incorporation into phospholipids. Similar to free fatty acids neutral lipids increase except for at >50 µM HS-106 where they decrease.
Figure 12:
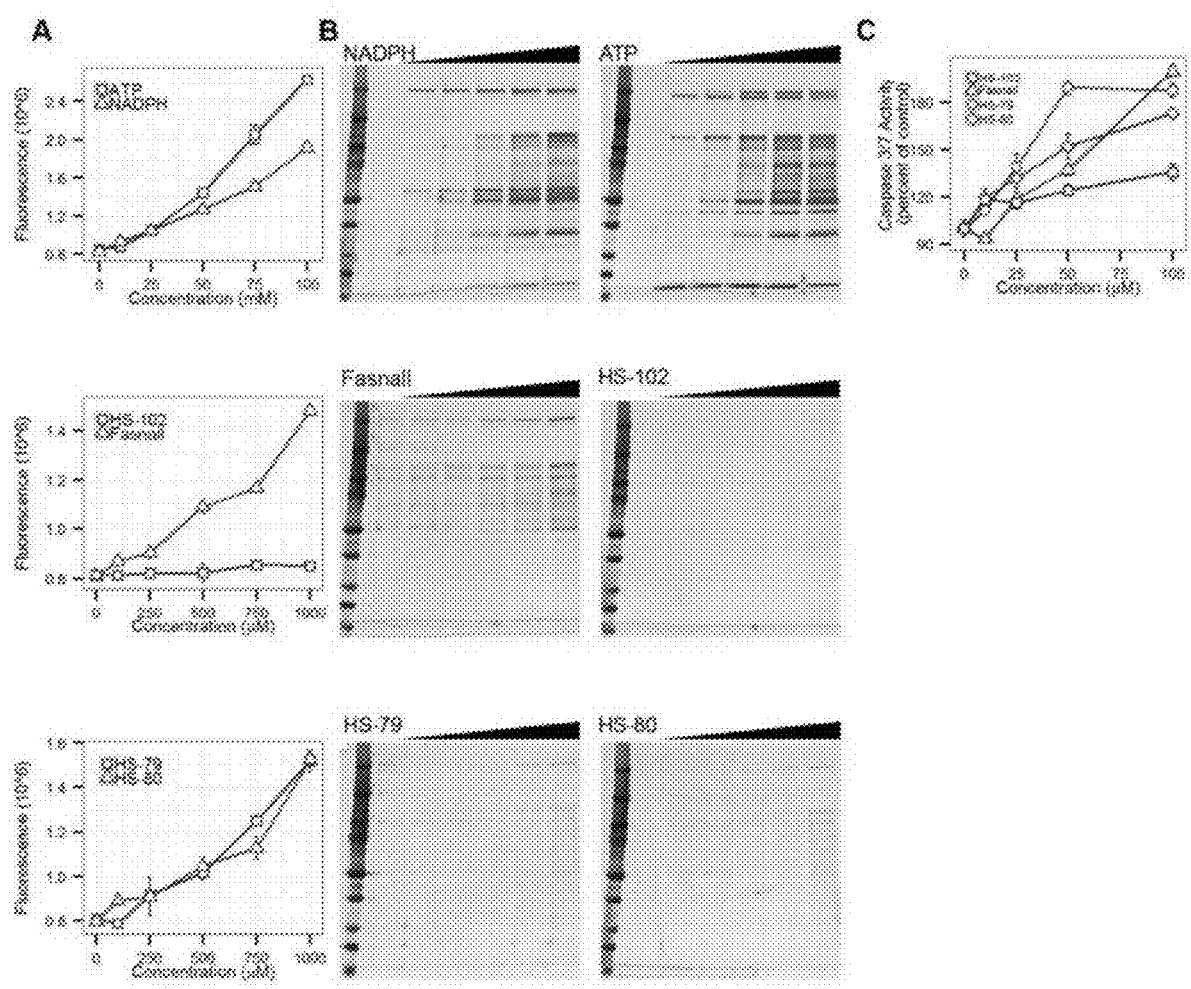
FIG. 12 graphically illustrates the blue Sepharose elution profile of HS-106 enantiomers and their caspase 3/7 activity. (A) Cibacron blue Sepharose was incubated with porcine lactating mammary gland extracts and bound proteins were labeled with fluorescein, the labeled proteins were eluted with different concentrations of Fasnall enantiomers and different concentrations of NADPH and ATP were used as controls, the eluted proteins fluorescence were measured. (B) the eluted proteins were separated by SDS-PAGE and proteins were identified by MS (*FASN). (C) The ability of Fasnall enantiomers to induce apoptosis was assessed by performing caspase 3/7 assay.
Figure 13:
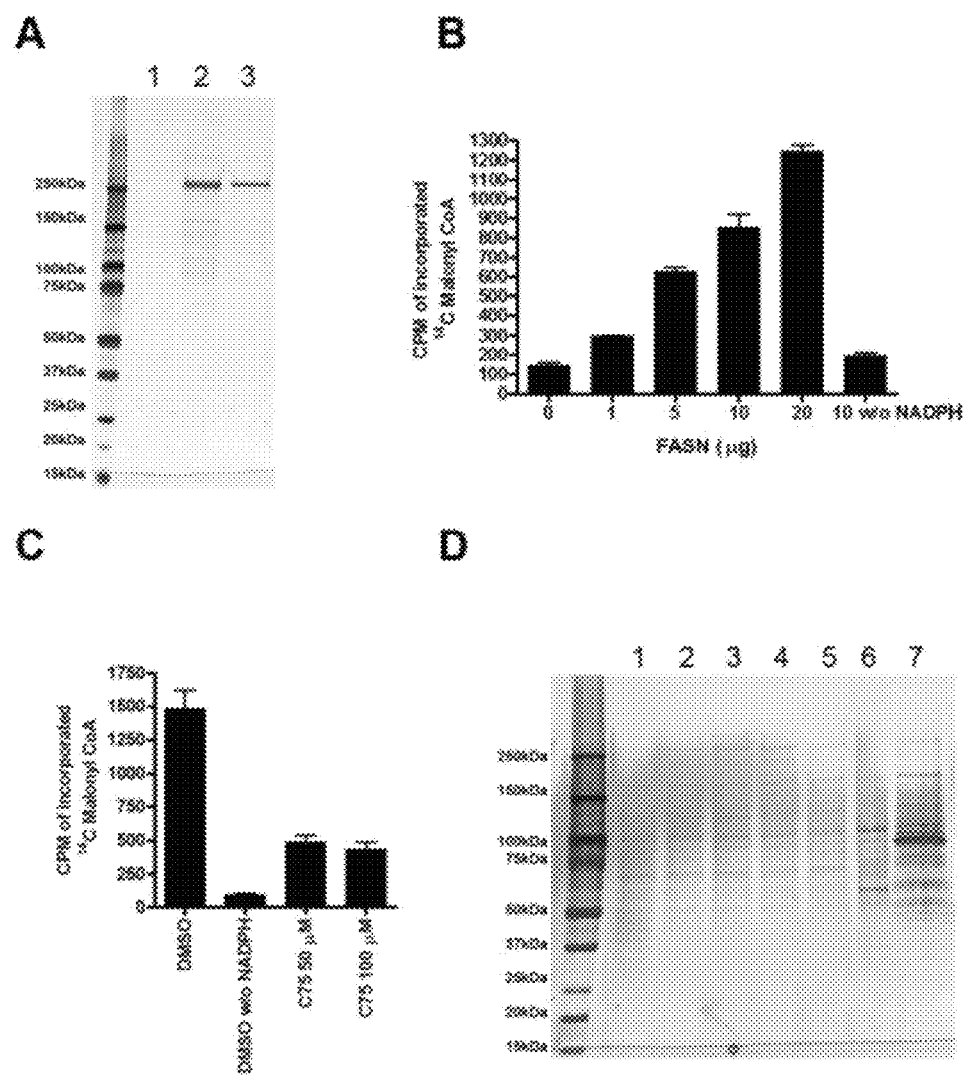
FIG. 13 illustrates the characterization of purified FASN and Fasnall elution of ATP Sepharose. (A) Purity of FASN from BT474 cells was assessed by SDS-PAGE, lane 1 and 2 is 10 µg and 20 µg of loaded protein respectively, estimating the purity to be around 85%. (B) Purified FASN shows a dose response increase in the activity of [$^{14}C$]-Malonyl CoA incorporation into lipids. (C) Inhibitory activity of C75 in the same assay. (D) Increased concentrations of Fasnall (DMSO, 1, 2.5, 5 and 10 mM lane 1-5 respectively) does not elute any proteins more than DMSO of ATP Sepharose loaded with BT474 cells lysate. Lane 6 and 7 are 10 mM Staurosporine and 50 mM ATP, respectively, as positive controls.
Figure 14:
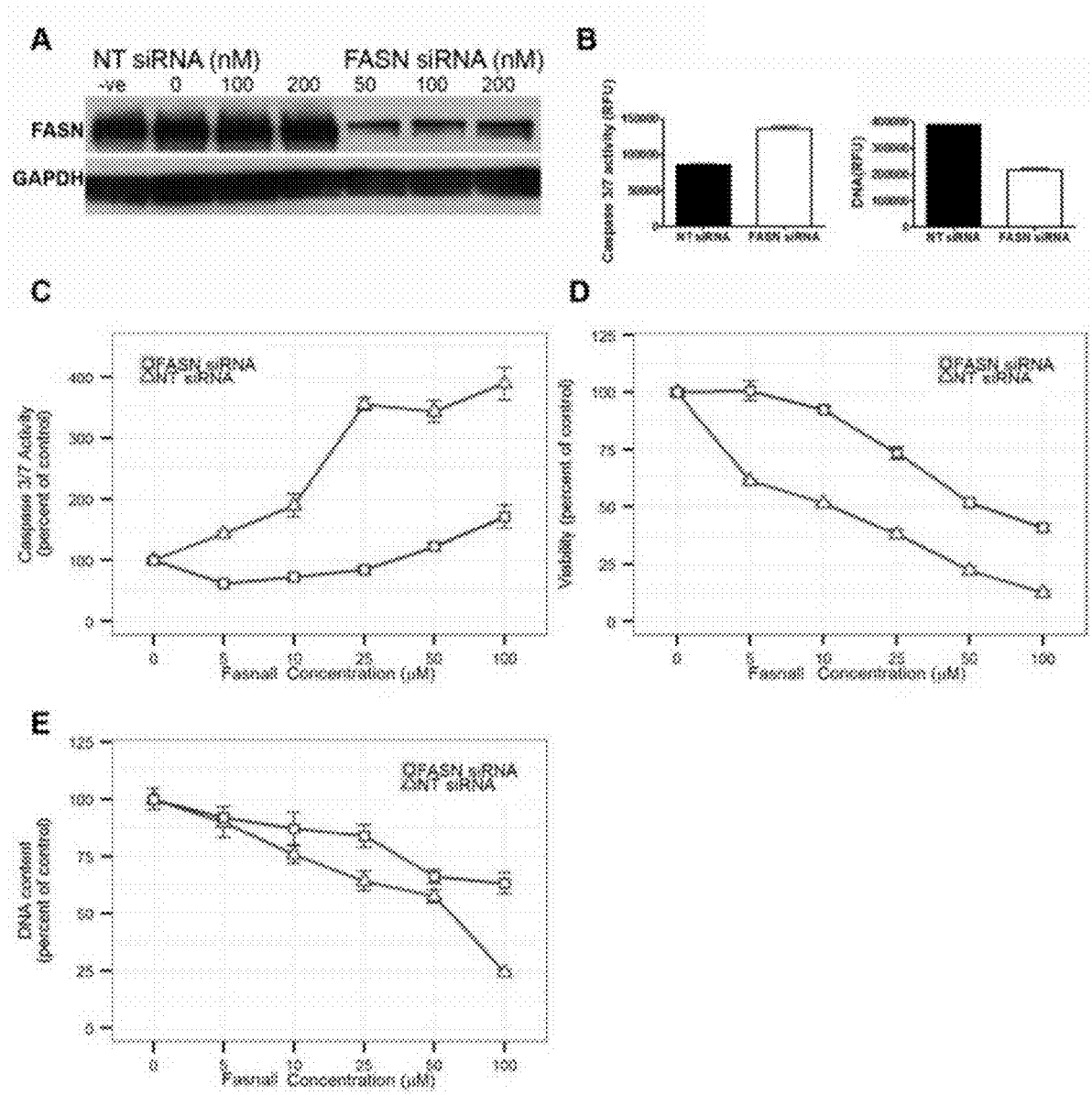
FIG. 14 illustrates the effect of FASN knockdown on Fasnall induced toxicity. (A) BT474 cells were treated with different concentrations of FASN smartpool siRNA, 85% of reduction in FASN expression was observed. (B) FASN siRNA were found to induce apoptosis and inhibit cell proliferation in BT474 cells. BT474 cells were treated with different Fasnall concentrations after FASN siRNA transfection FASN siRNA transfection was able to reduce Fasnall ability to (C) induce Caspase 3/7 activity, (D) inhibit cells proliferation and (E) viability.

Example 2. HS-106 Alters the Global Cellular Lipid Profile of BT474 Cells Consistent with Selective FASN Inhibition To determine the effects of HS-106 on the whole cell lipid profile, we carried out lipidomic analysis by LC-MS-MS following 2 hours of exposure to 10 μM HS-106 in BT474 cells (FIG. 5). Using ESI+ and ESI− profiling, more than 3000 lipids features can be simultaneously quantified and our analysis showed that HS-106 induced more than two fold change in abundance of 167 specific molecules (p<0.01 relative to vehicle). Most of the fatty acids identified to change were essential fatty acids (FIG. 6). Notably HS-106 also induced a compensatory effect on oleic and palmitoleic acid uptake from the cell culture media. This was confirmed by a $^{14}C$ palmitate uptake assay where HS-106 treatment increased $^{14}C$ labeling of free fatty acids (FIG. 11). Other lipids of particular note that increased many fold with HS-106 are ceramides, which are considered as pro-apoptotic lipids. The increase of ceramides would be expected due to malony-CoA (the direct substrate of FASN) accumulation and its effects on CPT-1 inhibition (Bandyopadhyay et al., 2006). As a consequence, any free fatty acids (derived primarily from the extracellular media) are likely to be condensed to 3-keto dihydrosphingosine and on through a series of reduction and acylation steps to various ceramides such as dihydroceramide and ceramide. Diacylglycerols were also found to increase significantly except for DG (14:1/18:2), which can indicate an overall increase in the lipolysis of Phosphatidylinositol 4,5-bisphosphate (PIP2) or an increase in de novo synthesis of diacylglycerols. Increase in diacylglycerol accumulation would be expected as a consequence of FASN inhibition, since this would be predicted to promote accumulation of glycerol, a precursor of triglyceride and diacylglycerols. This is because flux of carbons normally supplied by glycolysis for de novo fatty acid is now blocked at the level of FASN itself causing accumulation of all upstream intermediates (Haystead et al., 1989).

Figure 7:
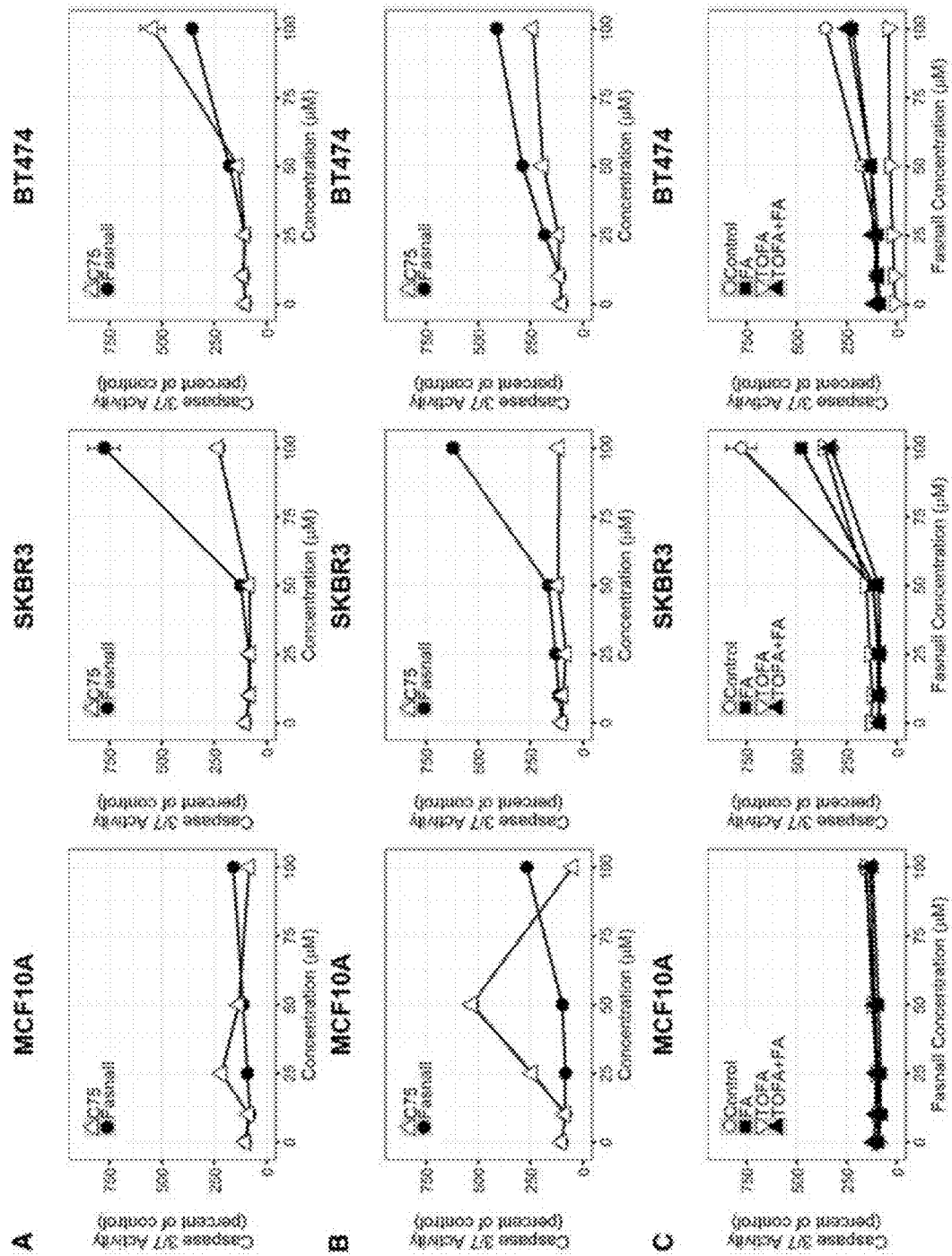
FIG. 7 graphically illustrates that HS-106 induces apoptosis in HER2+ breast cancer cells. (A) The indicated cells were treated with different concentrations of HS-106 or C75 for 24 hours then the Caspase 3/7 activity was assayed using the fluorogenic substrate (DEVD)$_2$-r1110. (B) Cells were pretreated for one hour with 100 μM palmitate (PA) made as a part of mixture of 1:2 palmitate/oleate in complex with 0.1% BSA or 15 μM TOFA or both (TOFA+PA). All the treatments contained the exact amount of BSA and DMSO. Then, cells were treated with different concentrations of HS-106 or C75 for 24 hours and Caspase 3/7 activity was assayed.
Figure 15:
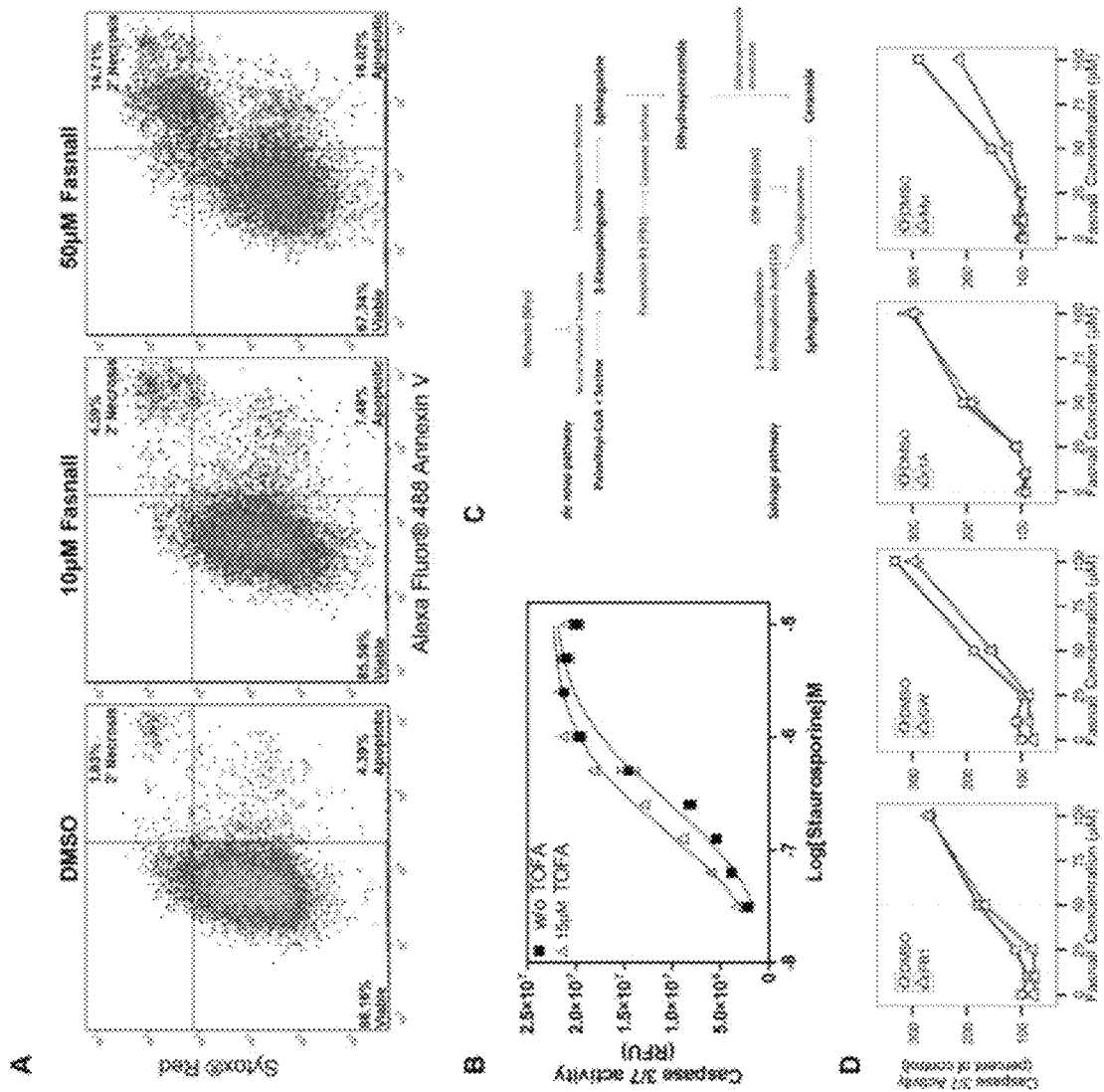
FIG. 15 illustrates that Fasnall induces apoptosis in BT474 cells that can be partially reversed by the SPT-1 inhibitor Myriocin. (A) BT474 cells were treated with Fasnall for 24 hours and apoptotic cells quantified by flow cytometry through quantifying Annexin V and Sytox Red stained cells. (B) BT474 cells were treated with different concentrations of the pan PKC inhibitor Staurosporine with or without TOFA. Staurosporine induction of apoptosis was not reversible by TOFA. (C) Several ceramide synthesis inhibitors were used to rescue BT474 cells from apoptosis, the schematic shows the positions of the enzymes targeted by these inhibitors in the de now and salvage pathways. (D) BT474 cells were pretreated with 10 µM of each ceramide synthesis inhibitor then with increasing concentrations of Fasnall, caspase 3/7 assay was performed after 24 hours and only Myriocin was able to modestly rescue the cells.

Example 3. Anti-Proliferative Activity of HS-106 is Due to the Induction of Apoptosis Inhibition of FASN in rapidly proliferating tumorigenic cells would be predicted to have two major effects; first, limit the oxidative capacity of the mitochondria through increasing malonyl CoA levels; second, trigger program cell death pathways via accumulation of ceramide. To investigate the latter mechanism, we examined Caspase 3 and 7 activation in response to HS-106 and C75 (FIG. 7A). Consistent with their tumorigenic capacities, SKBR3 and BT474 cells had 2 to 10 fold (respectively) higher caspase activity than MCF10A cells in response to HS-106 or C75 treatment. The ability of HS-106 to induce apoptosis was also confirmed by detecting the presence of phosphatidylserine and phosphatidylcholine on the outer leaflet of the plasma membrane using fluorescently labeled Annexin V and flow cytometry (FIG. 15A). To further confirm that HS-106 induction of apoptosis is directly related to the inhibition of FASN, we tried to rescue the cells by pretreating them with different combinations of palmitate (the end product of FASN) and the (Acetyl CoA Carboxylase) ACC inhibitor TOFA to prevent malonyl CoA accumulation (FIG. 7C). However, in our hands, only TOFA treatment was able to completely reverse the effect of HS-106 in BT474 cells which was not due to a general anti-apoptotic activity of TOFA (FIG. 15B), while palmitate, or the combination of both palmitate and TOFA, did not fully reverse the effect of the inhibitor. In SKBR3 cells, TOFA, palmitate and the combination of both, was able to partially reverse the effect of HS-106.

Example 4. Toxicity and Pharmacokinetic Studies in Mice

Figure 16:
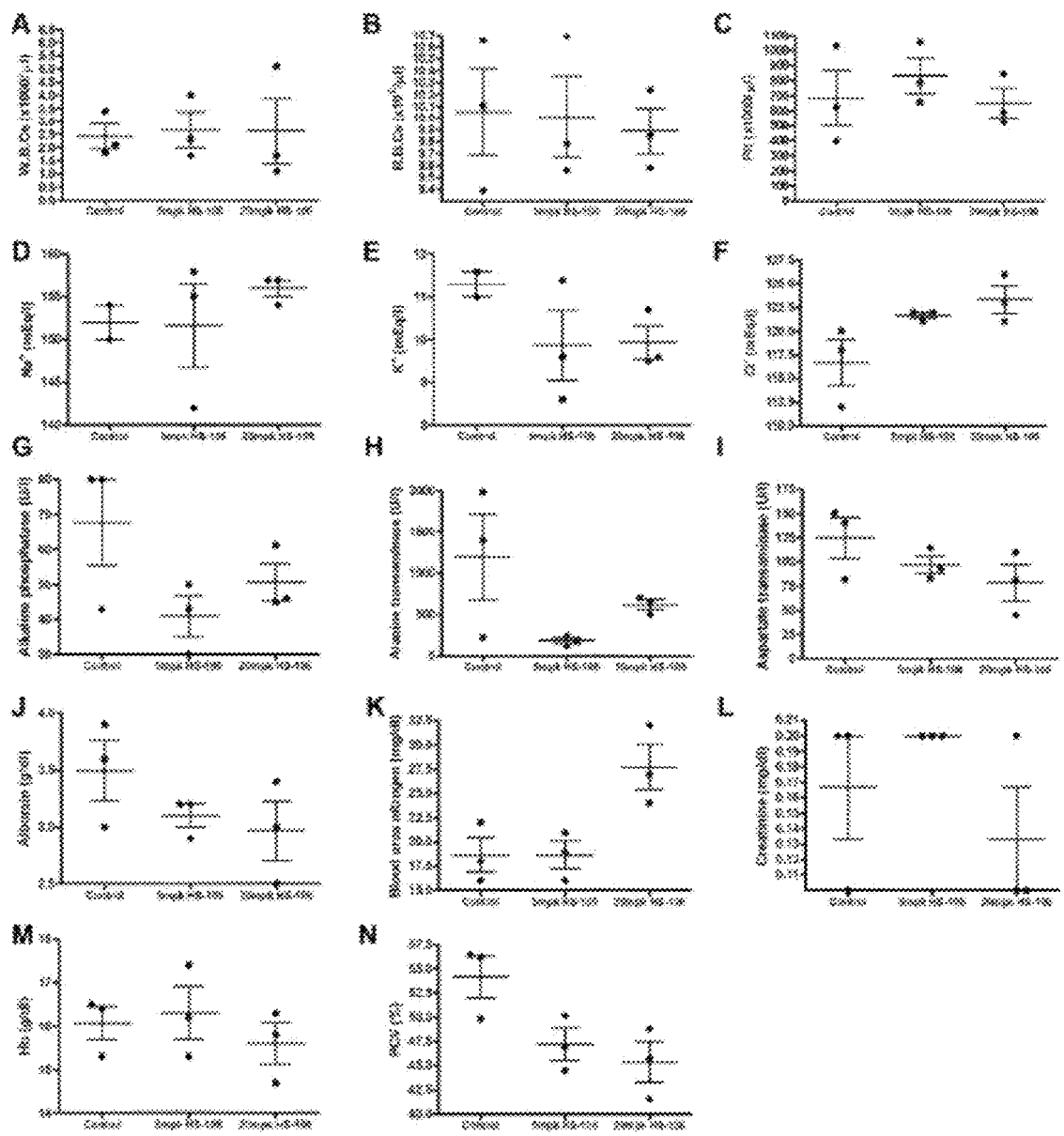
FIG. 16 illustrates the effects of HS-106 on mice liver and kidney functions. FVB/J mice were treated with two doses of HS-106 for a week. After that, the mice were sacrificed and blood was collected. The samples were assayed for blood cell count (A, B and C), electrolytes (D, E and F), liver functions (G, H and I), kidney functions (J, K and L) and hemoglobin (M) and packed cell volume (N).
Figure 17:
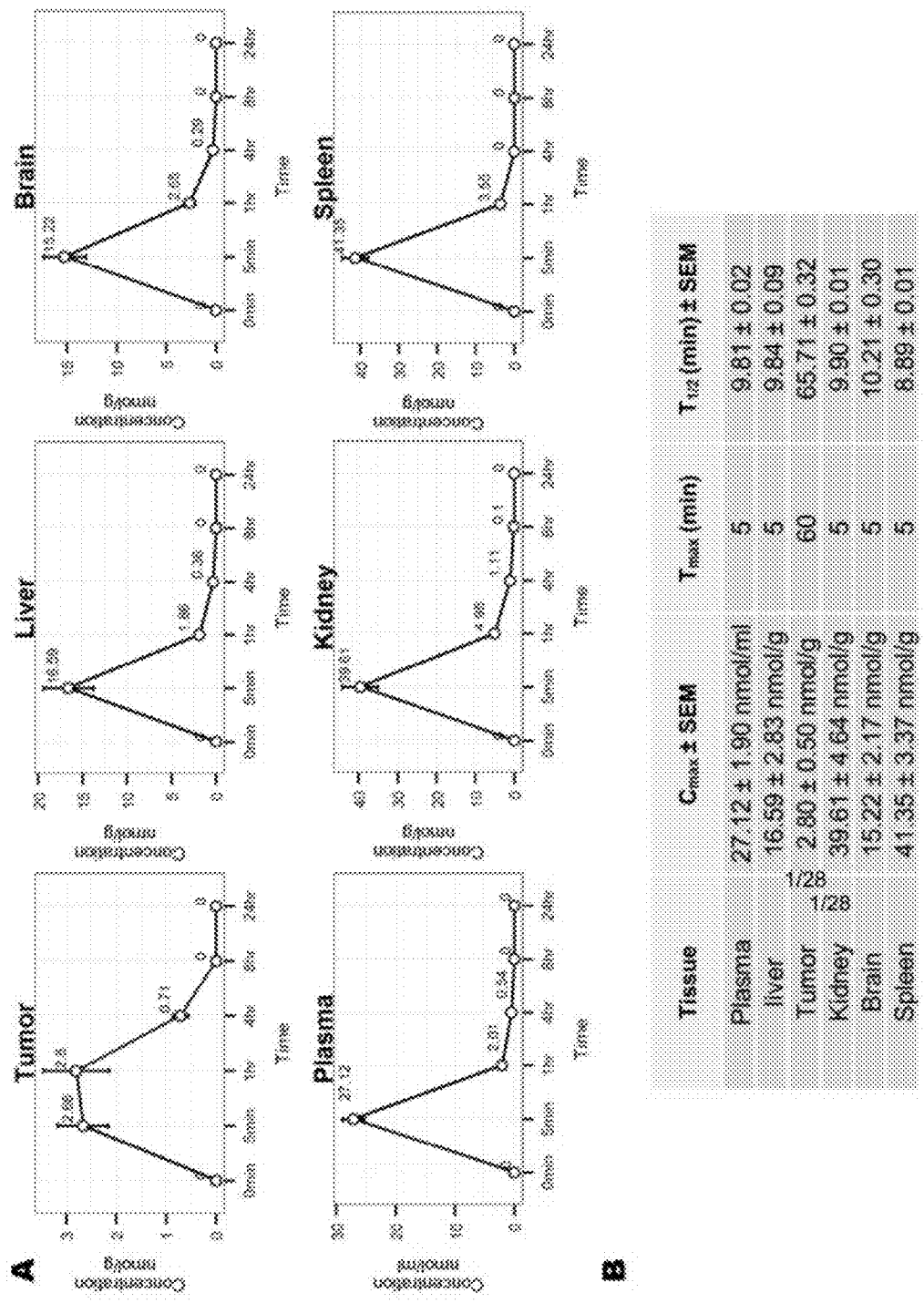
FIG. 17 illustrates the pharmacokinetics of Fasnall. (A). After one IP dose of 15 mg/kg (30 pmol/kg) of HS-106, FVB/J Neu mice were sacrificed at different time points and tissues were collected and assayed for Fasnall concentration by LC/MS. (B). T1/2 was calculated for each one of the tissues.

In an acute toxicity study, FVB/J mice received 10, 40, or 160 pmol/kg HS-106 via intraperitoneal injection (IP) on days 1 and 3, and blood was collected on day 4. HS-106 was toxic at 160 pmol/kg, but at 10 and 40 pmol/kg, HS-106 was well tolerated with no adverse effects on white blood cell counts, hemoglobin levels, kidney, or liver functions (FIG. 16). To test for the long term effects of HS-106, mice received biweekly IP injections of 10, 20, or 30 pmol/kg HS-106 for eight weeks. None of these doses induced any signs of toxicity, stress or any significant change in mice weight (FIG. 16). Next, we carried out pharmacokinetic (PK) studies to determine the uptake and bio-distribution of HS-106 in MMTV-Neu mice by LC-MS (FIG. 17). These studies showed HS-106 appears rapidly in the plasma within 5 minutes of the IP injection and is cleared rapidly ($T_{1/2}$=9.81±0.02 min n=3). Similar uptake and clearance was also observed in liver and kidney (liver $T_{1/2}$=9.8410.09 min, n=3; kidney $T_{1/2}$=9.90±0.01 min, n=3). Although the MS analysis focused primarily on the parent compound (amu 339 Da), preliminary examination of the entire liquid chromatography profile following drug extraction of the tissues did not reveal any obvious HS-106 metabolites (data not shown). These findings suggest that HS-106 is rapidly cleared through the kidney and liver in its parent ion state.

Example 5. MMTV-Neu Mice Survival Increases Upon Treatment with HS-106

Figure 8:
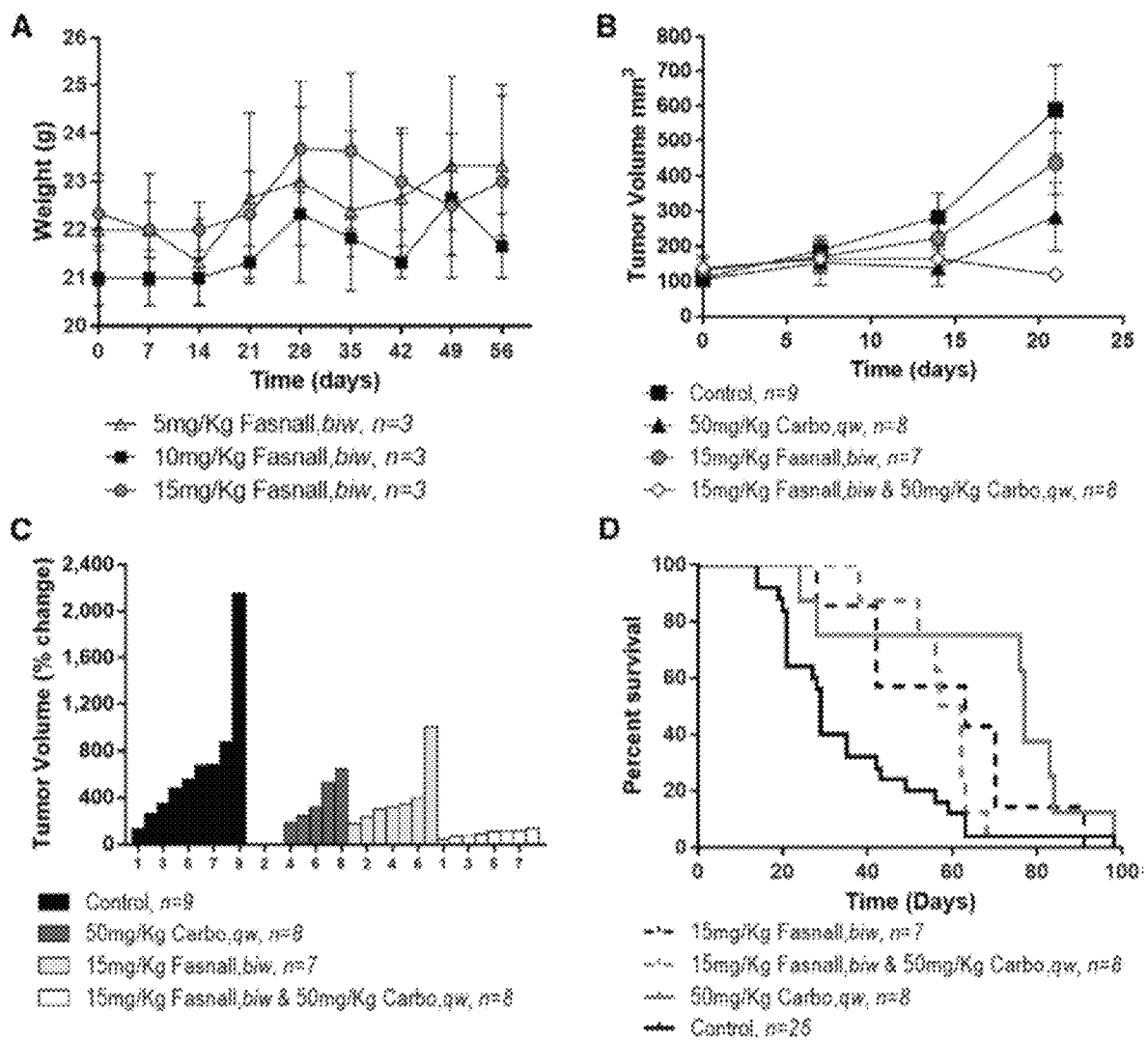
FIG. 8 graphically illustrates HS-106 activity in MMTV-Neu mice. (A) HS-106 does not induce weight change. Mice were assessed weekly, treated BIW with an IP injection of different concentrations of HS-106 made in 1:1 DMSO/saline. (B,C) combination of HS-106 and Carboplatin significantly reduce tumor volume (t-test, P value=0.014). (D) HS-106 increases the median survival of the mice from 29 to 63 days with a log-rank P value of 0.049.

Having determined that HS-106 was well tolerated in mice, it was next tested for efficacy on tumor progression in the Mouse Mammary Tumor Virus (MMTV)-Neu model of HER2+ breast cancer (Muller et al., 1988) (Jackson Labs Strain 002376). Cohorts of MMTV Neu mice were treated with a biweekly IP injection of 30 pmol/kg HS-106 (FIGS. 8B and C). When given alone, HS-106 reduced tumor volume compared with vehicle treated animals (day 21 HS-106 treatment volume 436±218 mm n=7 SDM, control volume 628±381 mm n=9, p=0.85). Significantly, HS-106 also increased the median survival of the MMTV Neu mice to 63 days (p=0.049) compared with vehicle alone treated animals (FIG. 8D). Importantly, MS analysis of tumor tissue verified HS-106 uptake and also showed a significantly longer elimination time ($T_{1/2}$=65.71±0.32 min n=3) than all other tissues tested. The long duration of treatment in our studies suggest the dosing frequency of HS-106 can be greatly increased to achieve greater effects on survival and tumor volume. These findings are consistent with effects of HS-106 as an anti-proliferative agent in tumors.

Figure 18:
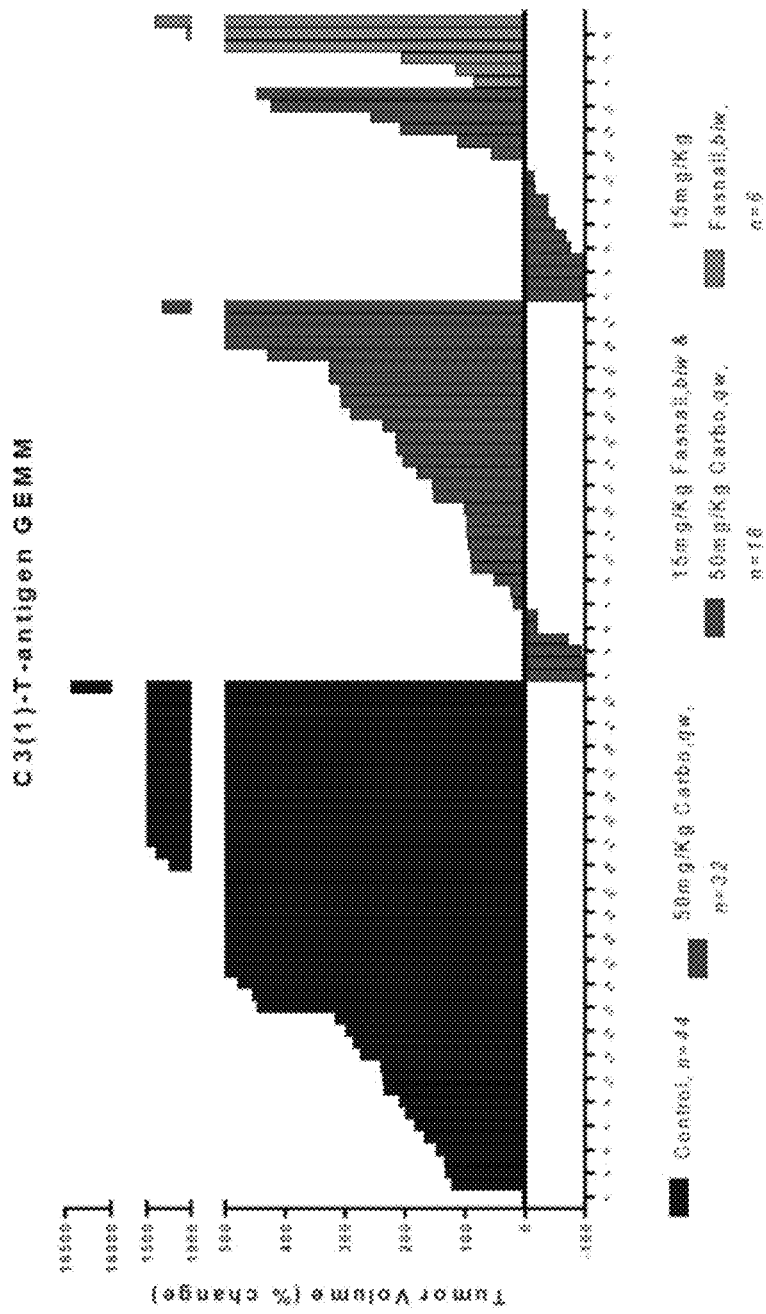
FIG. 18 illustrates the effects of Fasnall on tumor volume in TNBC C3Tag mice. IP treatment of C3Tag mice with a combination of Carboplatin and Fasnall significantly reduce tumor volume after 21 days.

More dramatic acute tumor responses were observed when HS-106 was combined with 143 pmol/kg of the platinum-based chemotherapeutic agent Carboplatin administered weekly. Here, 88% of tumors achieved an objective response rate of stable disease or better compared to Carboplatin only at 25%, fisher's exact, p-value 0.01. This response was not durable however as there was no long term benefit of the combination therapy at this dosing regimen (FIG. 8D). As often seen in the clinic, tumors that are responsive initially will develop resistance which is likely the case here. These findings are consistent with the actions of two compounds acting independently of one another; in which, one anti-neoplastic develops resistance while the other may be unaffected. Importantly, carboplatin is a front line chemotherapeutic agent for the treatment of breast cancer. Similar in action to cisplatin (Knox et al., 1986), carboplatin stops tumor progression by binding to DNA and inducing a DNA damage response that leads to halt proliferation and activation of apoptosis (Chu, 1994). Although Carboplatin is less toxic than the Cisplatin (Harland et al., 1984), toxicity is still a major issue where the drug dose is determined based on the target area under the curve (AUC) and evaluated drug clearance (Etienne et al., 2003), and in most cases is administered once every 4 weeks (Martin et al., 1992). Due to the efficacy of HS-106 when combined with Carboplatin in the MMTV-Neu model, we tested a similar combination in the C3Tag mouse model of triple negative breast cancer (TNBC). Unlike HER2+ or ER+ breast cancers, TNBC does not have any molecularly targeted drugs and platinum-based compounds are the most used chemotherapeutics for treatment. The combination of HS-106 and carboplatin was able to significantly reduce tumors volume in the C3Tag model (FIG. 18). These data, combined with the studies in the Neu model, indicates a strong, well-tolerated synergism between a fatty acid synthase inhibitor and a front line chemotherapeutic agent that is extensively used for breast cancer therapy.

Example 6. Determination of HS-106 Maximal Tolerated Dose

Female FVB/J mice aged to 10-12 weeks (Jackson Labs, Maine) were intraperitonealy injected with HS-106 at the described doses twice weekly. Mice were monitored for signs of toxicity by standard Mouse Phase 1 Unit (MPIU; https://www.med.unc.edu/mousephase1) protocols and approved by UNC-CH IACUC. Prior to end of the study 150 µl of whole blood was drawn via submandibular bleed and used to determine hematology values, liver, and kidney functions. To determine the long term effects of HS-106 on mice weight, female FVB/J mice aged 12-16 weeks were treated with the indicated concentrations of HS-106 twice weekly by intraperitoneal injection for 60 days. Mice body mass was assessed weekly and were observed every day for signs of toxicity such as labored breathing and hunched posture.

Example 7. Purification of Human FASN

Confluent BT474 cells grown in high glucose DMEM with 10% FBS, were scraped and washed twice with ice cold PBS. Then, the cells (2.26 g) were homogenized using potter homogenizer for 5 minutes in 40 ml of buffer A. The homogenate was centrifuged at 142,000×g for 45 minutes then filtered through glass wool resulting in a volume of 27 ml. To the 27 ml of homogenate, 6.37 ml of saturated ammonium sulfate (final saturation 20%) was added and mixed slowly for 20 min then incubated for 1 hour on ice. After centrifuging the lysate at 26,000×g for 20 minutes, the pellet was discarded and to the supernatant (26 ml) 7 ml saturated ammonium sulfate was added (final saturation 35%). After repeating the same procedure in the previous step, the supernatant was discarded and the pellet was collected and dissolved in 20 ml of buffer A and added to 150 KDa molecular mass cut off concentrator (Thermo Fisher Scientific, Waltham, Mass.) then centrifuged for 30 minutes at 1,600×g. The resulting volume on the filter (1.5 ml) was added to a Sephacryl S-300 HR column (1×100 cm) pre-equilibrated with PBS. The column was eluted with PBS containing 1 mM DTT at a flow rate of 0.2 ml/min. Fractions (2 ml) were collected and peak fractions were run on SDS-PAGE. Fractions with FASN (identified by (MALDI-TOF/TOF MS) were pooled and concentrated using 150 KDa cutoff concentrator.

Example 8. Determination of Acetate and Palmitate Incorporation into the Main Lipids Classes T474 cells were seeded in 6 well plates in 10% FBS 4.5 g/L glucose DMEM at a density of 400,000 cells/well. After 24 hours the media was changed with 0.1 g/L glucose DMEM containing different concentrations of HS-106. After 1 hour, to each well, 10 µCi of $^3$H acetate or 0.5 µCi of $^{14}$C palmitate (in complex with BSA) was added and incubated for 1 hour. Then, cells were treated with 500 µl trypsin/well for 5 min and subsequently 500 µl of ice cold PBS was added to each well. Lipids were separated as previously described (Kaluzny et al., 1985). Briefly, lipids were extracted three times with 700 µl of Chloroform and injected into Sep-PaK. Aminopropyl cartridges contains 360 mg of resin (Waters) Pre-equilibrated with 10 ml chloroform. The cartridges were then injected with 5 ml 2:1 chloroform:isopropanol, 2% acetic acid in ether and methanol to elute neutral lipids, free fatty acids and phospholipids respectively. To each fraction, 1 ml of 25 g/L Butyl PBD dissolved in Toluene was added and radioactivity was measured by scintillation counting.

Example 9. Annexin V Apoptosis Assay

After treating BT474 cells with different concentrations of HS-106 for 24 hours, the annexin V assay was executed as previously described (Safi et al., 2014). Briefly, cells were collected and stained with Alexa Fluor 488 Annexin V and Sytox Red according to the manufacturer's protocol. Annexin V-positive cells were considered apoptotic, and their percentage of the total number of cells was calculated. Ten thousand events were collected for each sample using a BD Accuri C6 flow cytometer (BD), and data were analyzed using the CFlow Plus program software (BD) and FCS express (De Novo Software).

Example 10. Determination of HS-106 Maximal Tolerated Dose

Female FVB/J mice aged to 10-12 weeks (Jackson Labs, Maine) were intraperitonealy (IP) injected twice weekly with HS-106 at the described doses. Mice were monitored for signs of toxicity by standard Mouse Phase 1 Unit (M1P1U; https://www.med.unc.edu/mousephase1) protocols and approved by UNC-CH IACUC. Prior to end of the study 150 µl of whole blood was drawn via submandibular bleed and used to determine hematology values, liver, and kidney functions by HemaTrue Hematology Analyzer (HESKA, Loveland, Colo., USA) and VITROS® 350 Chemistry System (J&J, New Brunswick, N.J.) according to manufacturer protocols. To determine the long term effects of HS-106 on mice weight, female FVB/J mice aged 12-16 weeks were treated with the indicated concentrations of HS-106 twice weekly by IP injection for 60 days. Mice body mass was assessed weekly, and mice were observed daily for signs of toxicity (e.g. labored breathing and hunched posture).

Example 11. HS-106 Pharmacokinetics

HS-106 pharmacokinetics was done as previously described (Howe et al., 2014). Briefly, MMTV-NEU mice were IP injected with 15 mg/kg of HS-106. After different time points (0, 5 min, 1 hr, 4 hr, 8 hr and 24 hr), tissues were collected, homogenized and assayed for HS-106 concentration by LC/MS using a standard curve for HS-106 and an internal standard.

Example 12. Synthesis of (N-(1-benzylpyrrolidin-3-yl)-5,6-dimethylthieno[2,3-d]pyrimidin-4-amine toluenesulfonate) HS-106

HS-106 was originally obtained from Enamine Ltd. (www.enamine.com, T5790201) but is no longer available from them. 4-Chloro-5,6-dimethylthieno[2,3-d]pyrimidine (1.02 g, 5.13 mmol) and 1-benzyl-3-aminopyrrolidine (1.09 g, 6.16 mmol) were combined and treated with Hunig's base (1.33 g, 10.3 mmol) and ethanol (4 mL). The mixture was heated to 100° C. for 2 h. The mixture was concentrated to an oil and chromatographed (silica gel 3.5×25 cm, ethyl acetate (250 mL), then 9/1 ethyl acetate/MeOH (400 mL). The product was dissolved in ethyl acetate and treated with toluenesulfonic acid (1 g) in ethyl acetate and stirred vigorously. The crystalline solid was filtered off and aid dried to give N-(1-benzylpyrrolidin-3-yl)-5,6-dimethylthieno[2,3-d]pyrimidin-4-amine toluenesulfonate (HS-106, 1.8 g, 70%) as a white powder. TLC $R_f$=0.21 in ethyl acetate, $R_f$=0.39 in 9/1 $CH_2Cl_2$/MeOH; LC/MS m/z=339.2; $^1$H NMR ($CD_3OD$) δ 8.29 (s, 1H), 7.68 (d, J=7.8 Hz, 2H, TsOH), 7.53 (br m, 2H), 7.42 (m, 4H), 7.15 (d, J=7.8 Hz, 2H, TsOH), 4.99 (m, 1H), 4.50 (d, J=13 Hz, 1H), 4.30 (d, J=13 Hz, 1H), 3.89 (m, 1H), 3.55 (m, 1H), 3.48 (dd, J=4.3, 12 Hz, 1H), 3.27 (M, 1H), 2.68 (m, 1H), 2.41 (s, 3H), 2.40 (s, 3H), 2.3-2.5 (m, 2H), 2.35 (s, 3H, TsOH).

Synthesis of HS-106 enantiomers: (R)—N-(1-benzylpyrrolidin-3-yl)-5,6-dimethylthieno[2,3-d]pyrimidin-4-amine HS-79

4-Chloro-5,6-dimethylthieno[2,3-d]pyrimidine (100 mg, 503 µmol) and (R)-(−)-1-benzyl-3-aminopyrrolidine (Aldrich, 89 mg, 503 µpmol) were combined, treated with Hunig's base (130 mg, 1 mmol) and ethanol (700 µL) and heated to 100° C. for 2 h. The reaction mixture was allowed to cool, diluted with DMSO (500 µL) and purified by prep HPLC (5 to 100% methanol with 0.2% formic acid, 20 mL/m, Agilent C-18, 21.1×25 cm) to give the product, a formate salt (190 mg, 98%) as a clear glass. LC/MS showed pure product (m/z=339.3, [M+1]$^+$) to be identical to the racemic commercial sample.

Synthesis of HS-106 Enantiomers: (S)—N-(1-benzylpyrrolidin-3-yl)-5,6-dimethylthieno[2,3-d]pyrimidin-4-amine HS-80

4-Chloro-5,6-dimethylthieno[2,3-d]pyrimidine (100 mg, 503 µmol) and (S)-(−)-1-benzyl-3-aminopyrrolidine (Aldrich, 89 mg, 503 µmol) were combined, treated with Hunig's base (130 mg, 1 mmol) and ethanol (700 µL) and heated to 100° C. for 2 h. The reaction mixture was allowed to cool, diluted with DMSO (500 µL) and purified by prep HPLC (5 to 100% methanol with 0.2% formic acid, 20 mL/m, Agilent C-18, 21.1×25 cm) to give the product, a formate salt (150 mg, 78%) as a clear glass. LC/MS showed pure product (m/z=339.3, [M+1]$^+$) to be identical to the racemic commercial sample.

Synthesis of HS-102

4-Chloro-5,6-dimethylthieno[2,3-d]pyrimidine (100 mg, 503 µmol) and 1-BOC-3-aminopyrrolidine (103 mg, 554 µmol) were combined and treated with Hunig's base (130 mg, 1 mmol) and ethanol (700 µL) and heated to 70° C. for 18 h. The reaction mixture was concentrated to an oil and chromatographed (silica gel, 9/1 CH$_2$Cl$_2$/MeOH) to give the intermediate as a glass. The glass was dissolved in methylene chloride (~4 mL) and treated with TFA (~1 mL). After about 1 h, the reaction mixture was concentrated, dissolved in DMSO (~1 mL) and purified by prep HPLC (0 to 100%/o methanol, 20 mL/m, Agilent C-18, 21.1×25 cm) to give the product (~136 mg) as an oil. The oil was dissolved in ethanol and treated with 60 µL of 12 N HCl, which caused a lot of solid formation. The mixture was heated to reflux, allowed to cool, and filtered off and air dried to give product (90 mg, 63%) as a white powder. LC/MS showed a pure product with an m/z=249.1, [M+1]$^+$.

REFERENCES

Adachi, A. et al., *J. Virol.* 59, 284 (1986).

Alo, P. et al. (1996). Expression of fatty acid synthase (FAS) as a predictor of recurrence in stage I breast carcinoma patients. Cancer 77, 474-482.

Ameer, F. et al. (2014). De novo lipogenesis in health and disease. Metabolism: clinical and experimental 63, 895-902.

Aragones, G. et al., *BMC Gastroenterol* 10, 92 (2010).

Bandyopadhyay, S. et al. (2006). Mechanism of apoptosis induced by the inhibition of fatty acid synthase in breast cancer cells. Cancer Res 66, 5934-5940.

Bligh, E.; Dyer, W. *J. Can J Biochem Physiol* 37, 911 (1959).

Brusselmans, K. et al. (2009). The Lipogenic Switch in Cancer. In Mitochondria and Cancer (Springer New York), pp. 39-59.

Bryant M, Ratner L. Myristoylation-dependent replication and assembly of human immunodeficiency virus 1. Proc Natl Acad Sci USA. 1990; 87:523-527.

Bushman. F. et al., *PLoS Pathog.* 5, e1000437 (2009).

Carlson, D. et al. (2013). Fluorescence linked enzyme chemoproteomic strategy for discovery of a potent and selective DAPK1 and ZIPK inhibitor. ACS chemical biology 8, 2715-2723.

Chakravarthy, M. et al. "New" hepatic fat activates PPARalpha to maintain glucose, lipid, and cholesterol homeostasis. Cell Metab. 2005; 1:309-322.

Chirala, S. et al. Fatty acid synthesis is essential in embryonic development: fatty acid synthase null mutants and most of the heterozygotes die in utero. *Proc Natl Acad Sci USA.* 2003; 100:6358-6363.

Chu, G. (1994). Cellular responses to cisplatin. The roles of DNA-binding proteins and DNA repair. The Journal of biological chemistry 269, 787-790.

Dorr, P. et al., *Antimicroh. Agents Chemother.* 49, 4721 (2005).

Edmonds, T. et al., *Virology* 408, 1 (2010).

Etienne, M. et al. (2003). Pharmacokinetics of low-dose carboplatin and applicability of a method of calculation for estimating individual drug clearance. Annals of oncology: official journal of the European Society for Medical Oncology/ESMO 14, 643-647.

Fadden, P. et al., *Chem Biol* 17, 686 (2010).

Felder, E. et al. (2012). The generation of purinome-targeted libraries as a means to diversify ATP-mimetic chemical classes for lead finding. Molecular diversity 16, 27-51.

Fritz, L. et al. (2001). Rapid methods for identifying modifiers of cellular apoptosis activity (Google patents).

Funabashi, H. et al., *J. Biochem.* 105, 751 (1989).

Graves, P. et al., *Mol. Pharmacol.* 62, 1364 (2002).

Greseth M D, Traktman P. De novo fatty acid biosynthesis contributes significantly to establishment of a bioenergetically favorable environment for vaccinia virus infection. PLoS Pathog. 2014; 10:e1004021.

Hardwicke, M. et al. (2014). A human fatty acid synthase inhibitor binds beta-ketoacyl reductase in the keto-substrate site. Nature chemical biology 10, 774-779.

Harland, S. et al. (1984). Pharmacokinetics of cis-diammine-1,1-cyclobutane dicarboxylate platinum(II) in patients with normal and impaired renal function. Cancer Res 44, 1693-1697. Haystead, C. et al., *Eur. J. Biochem.* 214, 459 (1993).

Haystead, T. (2006). The purinome, a complex mix of drug and toxicity targets. Current topics in medicinal chemistry 6, 1117-1127.

Haystead, T. et al. (1986). Both insulin and epidermal growth factor stimulate lipogenesis and acetyl-CoA carboxylase activity in isolated adipocytes. Importance of homogenization procedure in avoiding artefacts in acetyl-CoA carboxylase assay. The Biochemical journal 234, 279-284.

Haystead, T. et al. (1989). Effects of the tumour promoter okadaic acid on intracellular protein phosphorylation and metabolism. Nature 337, 78-81.

Heaton, N. et al., *Proc. Natl. Acad. Sci. USA* 107, 17345 (2010).

Howe, M. et al. (2014). Identification of an allosteric small-molecule inhibitor selective for the inducible form of heat shock protein 70. Chemistry & biology 21, 1648-1659. Huang, J. et al., *J. Virol.* 87, 4994 (2013).

Huang J T, Tseng C P, Liao M H, Lu S C, Yeh W Z, Sakamoto N et al. Hepatitis C virus replication is modulated by the interaction of nonstructural protein NS5B and fatty acid synthase. J. Virol. 2013; 87:4994-5004.

Hughes, P. et al. (2012). A highly selective Hsp90 affinity chromatography resin with a cleavable linker. Bioorganic & medicinal chemistry 20, 3298-3305.

Iwanaga, T. et al. (2009). Dynamic protein palmitoylation in cellular signaling. Progress in lipid research 48, 117-127.

Kaluzny, M. et al. (1985). Rapid separation of lipid classes in high yield and purity using bonded phase columns. Journal of lipid research 26, 135-140.

Knapp, M. et al. (2006). Targeting cancer: the challenges and successes of structure-based drug design against the human purinome. Current topics in medicinal chemistry 6, 1129-1159.

Knox, R. et al. (1986). Mechanism of cytotoxicity of anti-cancer platinum drugs: evidence that cis-diaminedichloroplatinum(II) and cis-diammine-(1,1-cyclobutanedicarboxylato)platinum(II) differ only in the kinetics of their interaction with DNA. Cancer Res 46, 1972-1979. Kridel, S. et al., *Cancer Res.* 64, 2070 (2004).

Kuhajda, F. et al. (2000). Synthesis and antitumor activity of an inhibitor of fatty acid synthase. Proceedings of the National Academy of Sciences of the United States of America 97, 3450-3454.

Kuhajda, F., *Nutrition* 16, 202 (2000).

Landis-Piwowar, K. et al. (2007). A novel prodrug of the green tea polyphenol (−)-epigallocatechin-3-gallate as a potential anticancer agent. Cancer Res 67, 4303-4310.

Li, H., Dou J, Ding L, Spearman P. Myristoylation is required for human immunodeficiency virus type 1 Gag-Gag multimerization in mammalian cells. J Virol. 2007; 81:12899-12910.

Li, Y. et al., *J. Virol.* 78, 4197 (2004).

Lindwasser O W, Resh M D. Myristoylation as a target for inhibiting HIV assembly: unsaturated fatty acids block viral budding. Proc Natl Acad Sci USA. 2002; 99:13037-13042.

Liu, H. et al., *Int J Biochem Mol Biol* 1, 69 (2010).

Lorizate, M. et al., *Cell Microbiol* 15, 292 (2013).

Maier, T. et al. (2008). The crystal structure of a mammalian fatty acid synthase. Science 321, 1315-1322.

Martin, M. et al. (1992). Carboplatin: an active drug in metastatic breast cancer. Journal of clinical oncology: official journal of the American Society of Clinical Oncology 10, 433-437.

Martin-Acebes, M. et al., *PLoS ONE* 6, e24970 (2011).

Menendez, J. et al., *Nat. Rev. Cancer* 7, 763 (2007).

Miyaguchi, Y. et al. (2011). Simple method for isolation of glyceraldehyde 3-phosphate dehydrogenase and the improvement of myofibril gel properties. Animal science journal=Nihon chikusan Galdcaiho 82, 136-143.

Muller, W. et al. (1988). Single-step induction of mammary adenocarcinoma in transgenic mice bearing the activated c-neu oncogene. Cell 54, 105-115.

Muratsubaki, H. et al. (1994). Rapid purification of yeast cytoplasmic fumarate reductase by affinity chromatography on blue sepharose CL-6B. Prep Biochem 24, 289-296.

Murray, J. et al. (2009). Targeting the purinome. Methods Mol Biol 575, 47-92.

Oliveras, G. et al. (2010). Novel anti-fatty acid synthase compounds with anti-cancer activity in HER2+ breast cancer. Annals of the New York Academy of Sciences 1210, 86-92.

Ono, A. et al., *Proc. Natl. Acad. Sci. USA* 98, 13925 (2001).

Oslob, J. et al. (2013). Imidazopyridine-Based Fatty Acid Synthase Inhibitors That Show Anti-HCV Activity and in Vivo Target Modulation. ACS medicinal chemistry letters 4, 113-117.

Pal R, Gallo R C, Sarngadharan M G. Processing of the structural proteins of human immunodeficiency virus type 1 in the presence of monensin and cerulenin. Proc Natl Acad Sci USA. 1988; 85:9283-9286.

Pizer, E. et al. (2000). Malonyl-coenzyme-A is a potential mediator of cytotoxicity induced by fatty-acid synthase inhibition in human breast cancer cells and xenografts. Cancer Res 60, 213-218.

Puig, T. et al. (2009). Novel Inhibitors of Fatty Acid Synthase with Anticancer Activity. Clinical cancer research: an official journal of the American Association for Cancer Research 15, 7608-7615.

Puig, T. et al. (2011). A novel inhibitor of fatty acid synthase shows activity against HER2+ breast cancer xenografts and is active in anti-HER2 drug-resistant cell lines. Breast cancer research: BCR 13, R131.

Resh, M., *Biochim. Biophys. Acta* 1451, 1 (1999).

Richardson, R. et al. (2007). Novel antagonists of the thioesterase domain of human fatty acid synthase. Molecular cancer therapeutics 6, 2120-2126.

Richardson, R. et al., *J. Med Chem.* 51, 5285 (2008).

Russell, E. et al., *J. Virol.* 85, 8253 (2011).

Safi, R. et al. (2014). Copper signaling axis as a target for prostate cancer therapeutics. Cancer Res 74, 5819-5831.

Schneider, J. et al. Macrophage fatty-acid synthase deficiency decreases diet-induced atherosclerosis. *J Biol Chem.* 2010; 285:23398-23409

Smith, S., *FASEB J.* 8, 1248 (1994).

Sul, H. et al., *Annu. Rev. Nutr.* 18, 331 (1998).

Swinnen, J. et al. (2006). Increased lipogenesis in cancer cells: new players, novel targets. Current opinion in clinical nutrition and metabolic care 9, 358-365.

Thupari, J. et al. (2002). C75 increases peripheral energy utilization and fatty acid oxidation in diet-induced obesity. Proceedings of the National Academy of Sciences of the United States of America 99, 9498-9502.

Turrado, C. et al. (2012). New synthetic inhibitors of fatty acid synthase with anticancer activity. Journal of medicinal chemistry 55, 5013-5023.

Vazquez, M. et al. (2008). Discovery of GSK837149A, an inhibitor of human fatty acid synthase targeting the beta-ketoacyl reductase reaction. The FEBS journal 275, 1556-1567.

Wakil, S., *Biochemistry* 28, 4523 (1989).

Wakil, S. Fatty acid synthase, a proficient multifunctional enzyme. Biochemistry. 1989; 28:4523-4530

Wilsky, S. et al., *Arch Virol* 157, 259 (2012).

Yang, Y. et al. (2002). Activation of fatty acid synthesis during neoplastic transformation: role of mitogen-activated protein kinase and phosphatidylinositol 3-kinase. Experimental cell research 279, 80-90.

Yang W, Hood B L, Chadwick S L, Liu S, Watkins S C, Luo G et al. Fatty acid synthase is upregulated during hepatitis C virus infection and regulates hepatitis C virus entry and production. Hepatology. 2008; 48:1396-1403.

Yoshii, Y. et al., *PLoS ONE* 8, e64570 (2013).

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of the claimed embodiments. All of the various embodiments, aspects, and options disclosed herein can be combined in all variations. The scope of the compositions, formulations, methods, and processes described herein include all actual or potential combinations of embodiments, aspects, options, examples, and preferences herein. All patents and publications cited herein are incorporated by reference herein for the specific teachings thereof as noted, unless other statements of incorporation are specifically provided.

What is claimed is:

1. A method of inhibiting Fatty Acid Synthase (FASN) with a FASN inhibitor that binds to the FASN purine-binding cofactor domain, the method comprising contacting cells that express FASN with an inhibitor that binds to the FASN purine-binding cofactor domain.

2. The method of claim 1, wherein the inhibitor does not bind to the substrate domain.

3. The method of claim 1, wherein the inhibitor inhibits both acetate and glucose incorporation into total lipids.

4. The method of claim 3, wherein the inhibitor inhibits both acetate and glucose incorporation into lipids in the HepG2 cell line with an $IC_{50}$ value below about 300 nM.

5. The method of claim 1, wherein the inhibitor possesses a thiophenopyrimidine scaffold.

6. The method of claim 1, wherein the inhibitor possesses a thieno[2,3-d]pyrimidine scaffold.

7. The method of claim 1, wherein the compound is (N-(1-benzylpyrrolidin-3-yl)-5,6-dimethylthieno[2,3-d]pyrimidin-4-amine, or a pharmaceutically acceptable salt thereof.

8. A method of inhibiting viral replication in cells expressing FASN, the method comprising contacting the cells with an inhibitor that binds to the FASN purine-binding cofactor domain.

9. The method of claim 8, wherein the inhibitor does not bind to the substrate domain.

10. The method of claim 8, wherein the inhibitor inhibits HIV viral replication in a TZM-bl model of HIV replication with an $EC_{50}$ value below about 500 nM.

11. The method of claim 8, wherein inhibition of FASN reduces HV-1 particle production without affecting intracellular Gag production.

12. The method of claim 8, wherein the inhibitor attenuates HIV replication during a late stage of its replication cycle.

13. The method of claim 8, wherein nascent HIV-1 virion production is inhibited without reducing HIV-1 protein synthesis.

14. The method of claim 8, wherein the inhibitor possesses a thiophenopyrimidine scaffold.

15. The method of claim 8, wherein the inhibitor possesses a thieno[2,3-d]pyrimidine scaffold.

16. The method of claim 8, wherein the compound is (N-(1-benzylpyrrolidin-3-yl)-5,6-dimethylthieno[2,3-d]pyrimidin-4-amine, or a pharmaceutically acceptable salt thereof.

17. A method of treating a viral infection in a subject, the method comprising administering to the subject in need thereof, a therapeutically effective amount of a FASN inhibitor that binds to the FASN purine-binding cofactor domain.

18. The method of claim 17, wherein the viral load is reduced.

19. The method of claim 17, wherein the viral infection is infection by an enveloped virus.

20. The method of claim 17, wherein the viral infection is infection by a virus selected from the group consisting of human immunodeficiency virus, cytomegalovirus, Dengue, hepatitis B, hepatitis C, Epstein-Barr, influenza virus, respiratory syncytial virus and West Nile virus.

21. The method of claim 17, wherein the virus is human immunodeficiency virus.

22. The method of claim 17, wherein lipid dysregulation-based morbidities are reduced.

23. The method of claim 17, wherein the inhibitor possesses a thiophenopyrimidine scaffold.

24. The method of claim 17, wherein the inhibitor possesses a thieno[2,3-d]pyrimidine scaffold.

25. The method of claim 17, wherein the compound is (N-(1-benzylpyrrolidin-3-yl)-5,6-dimethylthieno[2,3-d]pyrimidin-4-amine, or a pharmaceutically acceptable salt thereof.

26. The method of claim 17, further comprising co-administration of an additional anti-retroviral compound.

* * * * *

UNITED STATES PATENT AND TRADEMARK OFFICE
CERTIFICATE OF CORRECTION

PATENT NO. : 10,966,981 B2  
APPLICATION NO. : 16/094872  
DATED : April 6, 2021  
INVENTOR(S) : Jesse Kwiek et al.

Page 1 of 1

It is certified that error appears in the above-identified patent and that said Letters Patent is hereby corrected as shown below:

In the Claims

Claim 11, Column 34, Line 56, the text "reduces HV-1 particle production without affecting intrac-" should be changed to --reduces HIV-1 particle production without affecting intrac- --

Claim 16, Column 35, Line 1, the text "16. The method of claim 8, wherein the compound is" should be changed to --16. The method of claim 8, wherein the inhibitor is--

Claim 25, Column 35, Line 26, the text "25. The method of claim 17, wherein the compound is" should be changed to --25. The method of claim 17, wherein the inhibitor is--

Signed and Sealed this  
Twenty-third Day of November, 2021

Drew Hirshfeld  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: FASN Primers

<400> SEQUENCE: 1
cccacctacg tactggccta                                                    20

<210> SEQ ID NO 2
<211> LENGTH: 20
<212> TYPE: DNA
<213> ORGANISM: Artificial Sequence
<220> FEATURE:
<223> OTHER INFORMATION: FASN Primers

<400> SEQUENCE: 2
cttggccttg ggtgtgtact                                                    20

<210> SEQ ID NO 3
<211> LENGTH: 20
<212> TYPE: DNA
<213> ORGANISM: Artificial Sequence
<220> FEATURE:
<223> OTHER INFORMATION: FASN Primers

<400> SEQUENCE: 3
cagccacccg agattgagca                                                    20

<210> SEQ ID NO 4
<211> LENGTH: 20
<212> TYPE: DNA
<213> ORGANISM: Artificial Sequence
<220> FEATURE:
<223> OTHER INFORMATION: FASN Primers

<400> SEQUENCE: 4
tagtagcgac gggcggtgtg                                                    20
```